US008735558B2

(12) United States Patent
Chan et al.

(10) Patent No.: US 8,735,558 B2
(45) Date of Patent: May 27, 2014

(54) BLOCKING THE MIGRATION OR METASTASIS OF CANCER CELLS BY AFFECTING ADHESION PROTEINS AND THE USES OF NEW COMPOUNDS THEREOF

(75) Inventors: Pui-Kwong Chan, Sugarland, TX (US); May Sung Mak, Hong Kong (CN)

(73) Assignee: Pacific Arrow Limited (CN)

( * ) Notice: Subject to any disclaimer, the term of this patent is extended or adjusted under 35 U.S.C. 154(b) by 787 days.

(21) Appl. No.: 12/541,713

(22) Filed: Aug. 14, 2009

(65) Prior Publication Data
US 2010/0004190 A1    Jan. 7, 2010

Related U.S. Application Data

(63) Continuation-in-part of application No. PCT/US2008/002086, filed on Feb. 15, 2008, which is a continuation-in-part of application No. PCT/US2007/077273, filed on Aug. 30, 2007, and a continuation-in-part of application No. PCT/US2006/016158, filed on Apr. 27, 2006, which is a continuation-in-part of application No. PCT/US2005/031900, filed on Sep. 7, 2005, and a continuation-in-part of application No. 11/117,760, filed on Apr. 27, 2005, now Pat. No. 7,727,561, and a continuation-in-part of application No. 11/131,551, filed on May 17, 2005, now Pat. No. 7,262,285, which is a continuation-in-part of application No. 11/117,745, filed on Apr. 27, 2005, now Pat. No. 7,514,412, application No. 12/541,713, which is a continuation-in-part of application No. 12/392,795, filed on Feb. 25, 2009, now Pat. No. 8,334,269, which is a continuation of application No. 10/906,303, filed on Feb. 14, 2005, now Pat. No. 7,524,824, application No. 12/541,713, which is a continuation-in-part of application No. PCT/US2009/034115, filed on Feb. 13, 2009, and a continuation-in-part of application No. 12/344,682, filed on Dec. 29, 2008, which is a continuation of application No. 11/289,142, filed on Nov. 28, 2005, now Pat. No. 7,488,753, and a continuation of application No. 11/267,523, filed on Nov. 4, 2005, now abandoned, application No. 12/541,713, which is a continuation-in-part of application No. 12/195,112, filed on Aug. 20, 2008, now abandoned, and a continuation-in-part of application No. 11/117,760, filed on Apr. 27, 2005, now Pat. No. 7,727,561.

(60) Provisional application No. 60/617,379, filed on Oct. 8, 2004, provisional application No. 60/613,811, filed on Sep. 27, 2004, provisional application No. 60/607,858, filed on Sep. 7, 2004, provisional application No. 60/890,380, filed on Feb. 16, 2007, provisional application No. 60/947,705, filed on Jul. 3, 2007.

(51) Int. Cl.
| | |
|---|---|
| A61K 31/7032 | (2006.01) |
| A61K 31/7034 | (2006.01) |
| C07H 15/256 | (2006.01) |
| C07C 69/753 | (2006.01) |
| C07C 69/757 | (2006.01) |

(52) U.S. Cl.
CPC .......... *C07H 15/256* (2013.01); *C07C 2103/54* (2013.01)
USPC .............. 536/18.1; 514/33; 514/35; 514/548; 514/549; 560/220

(58) Field of Classification Search
None
See application file for complete search history.

(56) References Cited

U.S. PATENT DOCUMENTS

| | | | |
|---|---|---|---|
| 6,197,306 | B1 | 3/2001 | Murali et al. |
| 6,231,859 | B1 | 5/2001 | Kensil |
| 6,444,233 | B1 | 9/2002 | Arntzen et al. |
| 6,616,943 | B2 * | 9/2003 | Wang ............................ 424/451 |
| 6,689,398 | B2 | 2/2004 | Haridas et al. |
| 6,746,696 | B2 | 6/2004 | Arntzen et al. |
| 6,962,720 | B2 | 11/2005 | Haridas et al. |
| 7,105,186 | B2 | 9/2006 | Arntzen et al. |
| 7,189,420 | B2 | 3/2007 | Wang et al. |
| 7,262,285 | B2 * | 8/2007 | Chan et al. ................... 536/18.1 |
| 7,488,753 | B2 * | 2/2009 | Chan et al. ..................... 514/510 |
| 7,514,412 | B2 * | 4/2009 | Chan et al. ....................... 514/33 |
| 7,524,824 | B2 * | 4/2009 | Chan et al. ....................... 514/33 |

(Continued)

FOREIGN PATENT DOCUMENTS

| | | |
|---|---|---|
| AU | 2002348988 | 11/2007 |
| AU | 2004281707 | 9/2011 |

(Continued)

OTHER PUBLICATIONS

Voutquenne et al., "Structure-Activity Relationships of Haemolytic Saponins" Pharmaceutical Biology (2002) vol. 40 No. 4 pp. 253-262.*

(Continued)

*Primary Examiner* — Eric S Olson
(74) *Attorney, Agent, or Firm* — Law Offices of Albert Wai-Kit Chan, PLLC

(57) ABSTRACT

This invention provides methods, processes, compounds and compositions for modulating the gene expression and modulating the secretion, expression, or synthesis of adhesion proteins or their receptors to cure disease, wherein the modulating comprises positive and negative regulating; wherein comprises inhibiting cancer growth, wherein the adhesion proteins or receptors comprise fibronectin, integrins family, Myosin, vitronectin, collagen, laminin, Glycosylation cell surface proteins, polyglycans, cadherin, heparin, tenascin, CD 54, CAM, elastin and FAK; wherein the methods, processes, compounds and compositions are also for anti-angiogenesis; wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer.

18 Claims, 6 Drawing Sheets

(56) References Cited

U.S. PATENT DOCUMENTS

Figure 1:
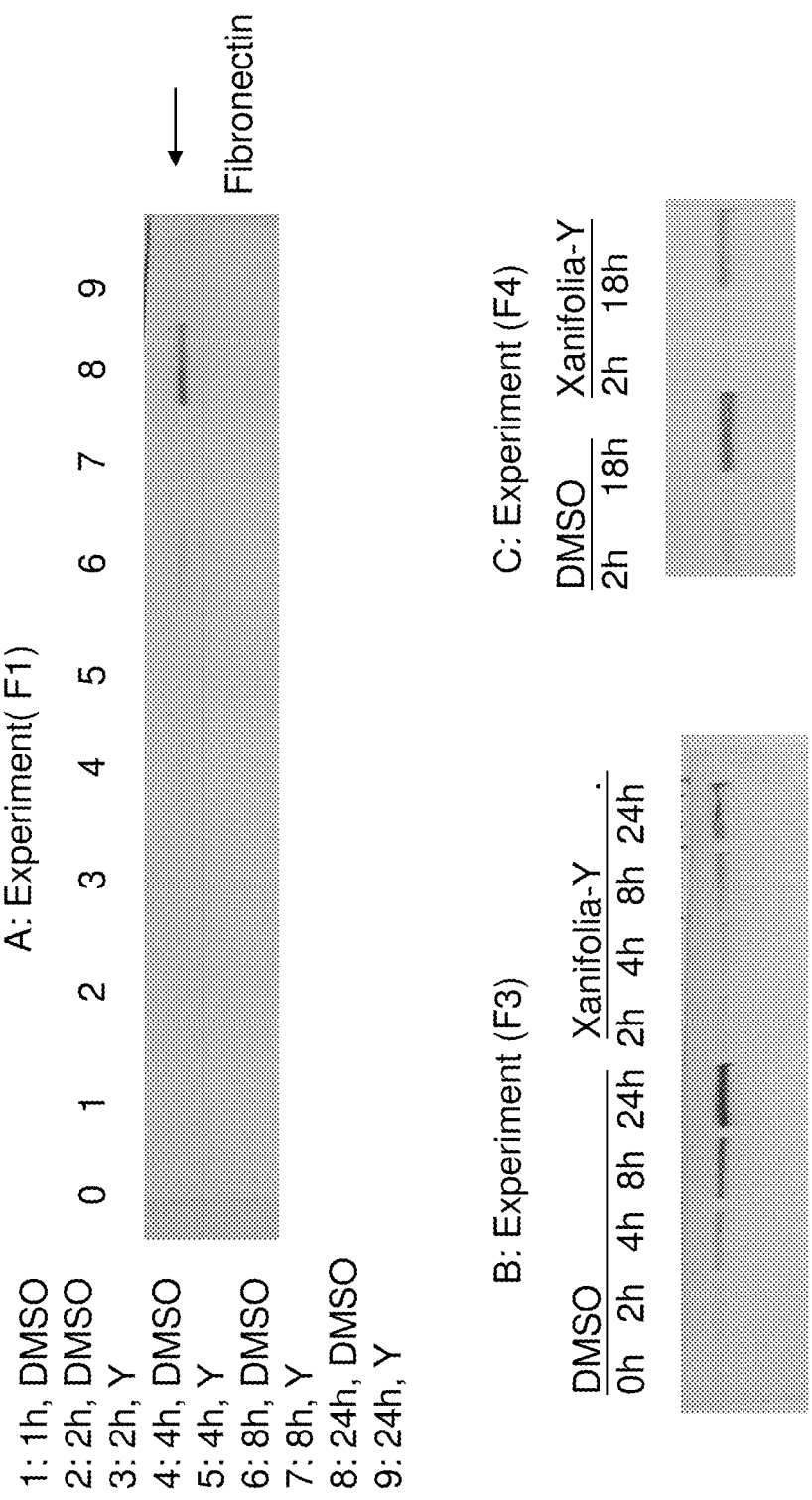

| | | | |
|---|---|---|---|
| 7,670,632 B2 | 3/2010 | Arntzen et al. | |
| 7,727,561 B2* | 6/2010 | Chan et al. | 424/725 |
| 7,780,974 B2 | 8/2010 | Gutterman et al. | |
| 2003/0082293 A1 | 5/2003 | Wang et al. | |
| 2003/0096030 A1 | 5/2003 | Wang et al. | |
| 2004/0138151 A1 | 7/2004 | Maes et al. | |
| 2005/0209445 A1 | 9/2005 | Gokaraju et al. | |
| 2005/0245470 A1* | 11/2005 | Chan et al. | 514/33 |
| 2005/0276872 A1* | 12/2005 | Chan et al. | 424/767 |
| 2006/0111310 A1* | 5/2006 | Chan et al. | 514/33 |
| 2006/0122129 A1* | 6/2006 | Chan et al. | 514/33 |
| 2006/0183687 A1 | 8/2006 | Cory | |
| 2006/0263458 A1 | 11/2006 | Mak et al. | |
| 2007/0161580 A1* | 7/2007 | Chan et al. | 514/33 |
| 2007/0196517 A1 | 8/2007 | San Martin | |
| 2007/0212329 A1 | 9/2007 | Bruck et al. | |
| 2007/0243269 A1 | 10/2007 | Mcneff et al. | |
| 2007/0249711 A1 | 10/2007 | Choi et al. | |
| 2007/0254847 A1 | 11/2007 | Liu et al. | |
| 2008/0058273 A1 | 3/2008 | Yang et al. | |
| 2008/0064762 A1 | 3/2008 | Fuchs et al. | |
| 2008/0096938 A1 | 4/2008 | Evindar et al. | |
| 2008/0112925 A1 | 5/2008 | Hancock | |
| 2008/0119420 A1 | 5/2008 | Liu et al. | |
| 2009/0041877 A1 | 2/2009 | Mak et al. | |
| 2009/0156515 A1* | 6/2009 | Chan et al. | 514/33 |
| 2009/0263512 A1* | 10/2009 | Chan et al. | 424/725 |
| 2010/0204169 A1* | 8/2010 | Chan et al. | 514/33 |
| 2010/0317606 A1* | 12/2010 | Chan et al. | 514/33 |

FOREIGN PATENT DOCUMENTS

| | | |
|---|---|---|
| CA | 2451740 | 12/2003 |
| CN | 93111010.6 | 5/1994 |
| CN | 1092991 A | 10/1994 |
| CN | 1092992 A | 10/1994 |
| CN | 02142258.3 | 8/2002 |
| CN | 1236792 C | 1/2006 |
| EP | 02781502.6 | 2/2004 |
| HK | 05102536.2 | 3/2005 |
| JP | 61-007285 | 1/1986 |
| JP | 61-130232 | 6/1986 |
| JP | 02-247196 | 10/1990 |
| JP | 2002-515430 A | 5/2002 |
| JP | 2003522442 | 2/2004 |
| JP | 2006-070018 | 3/2006 |
| JP | 4815558 | 9/2011 |
| JP | 4880479 B2 | 2/2012 |
| JP | 5087400 | 9/2012 |
| KR | 1020047002889 | 2/2004 |
| KR | 10-1135824 | 4/2012 |
| NZ | 530449 | 10/2007 |
| NZ | 546138 | 4/2010 |
| NZ | 554037 | 8/2011 |
| SG | 102310 | 3/2006 |
| SG | 120666 | 10/2008 |
| SG | 130542 | 1/2010 |
| TW | 091119471 | 8/2002 |
| TW | 93140030 | 12/2004 |
| TW | 94130519 | 9/2005 |
| WO | 0038700 A1 | 7/2000 |
| WO | 03017919 | 3/2003 |
| WO | WO2005/037200 * | 4/2005 |
| WO | WO2005/063273 * | 7/2005 |
| WO | 2006029221 | 3/2006 |
| WO | 2006116656 | 11/2006 |
| WO | 2008028060 A2 | 3/2008 |
| WO | 2011009032 | 1/2011 |

OTHER PUBLICATIONS

Sirtori, C., "Aescin: Pharmacology, Pharmacokinetics, and Therapeutic Profile" Pharmacological Research (2001) vol. 44 No. 3 pp. 183-193.*

PCT Written Opinion of the International Searching Authority for PCT/US04/33359, filed Oct. 8, 2004 for Pacific Arrow Limited et al., dated Apr. 12, 2005.

PCT International Search Report for PCT/US04/33359, filed Oct. 8, 2004 for Pacific Arrow Limited et al., dated Apr. 12, 2005.

PCT Written Opinion of the International Searching Authority for PCT/US04/43465, filed Dec. 23, 2004 for Pacific Arrow Limited et al., dated May 17, 2005.

PCT International Search Report for PCT/US04/43465, filed Dec. 23, 2004 for Pacific Arrow Limited et al., dated May 17, 2005.

PCT International Search Report issued on Feb. 6, 2007 for Pacific Arrow Limited, International App'l No. PCT/US2005/031900.

PCT Written Opinion of the International Searching Authority issued on Feb. 6, 2007 for Pacific Arrow Limited, International App'l No. PCT/US2005/031900.

PCT International Preliminary Report on Patentability issued on Mar. 22, 2007 for Pacific Arrow Limited, International App'l No. PCT/US2005/031900.

PCT International Preliminary Report on Patentability issued on Apr. 11, 2006 for Pacific Arrow Limited, International App'l No. PCT/US2004/033359.

PCT International Search Report issued on Nov. 13, 2006 for Pacific Arrow Limited, International App'l No. PCT/US2006/016158.

PCT Written Opinion of the International Searching Authority issued on Nov. 13, 2006 for Pacific Arrow Limited, International App'l No. PCT/US2006/016158.

U.S. Office Action for Mak, et al., U.S. Appl. No. 11/412,659, filed Apr. 27, 2006, Dated Mar. 8, 2007.

U.S. Final Office Action for Mak, et al., U.S. Appl. No. 11/412,659, filed Apr. 27, 2006, Dated Sep. 5, 2007.

U.S. Office Action for Chan, et al., U.S. Appl. No. 11/131,551, filed May 17, 2005, Dated Jan. 22, 2007.

U.S. Notice of Allowability for Chan, et al., U.S. Appl. No. 11/131,551, filed May 17, 2005, Dated May 11, 2007.

U.S. Office Action for Chan, et al., U.S. Appl. No. 11/289,142, filed Nov. 28, 2005, Dated Sep. 27, 2007.

U.S. Office Action for Chan, et al., U.S. Appl. No. 11/267,523, filed Nov. 4, 2005, Dated Sep. 27, 2007.

U.S. Office Action for Chan, et al., U.S. Appl. No. 10/906,303, filed Feb. 14, 2005, Dated Feb. 12, 2007.

U.S. Office Action for Chan, et al., U.S. Appl. No. 10/906,303, filed Feb. 14, 2005, Dated Jul. 27, 2007.

U.S. Office Action for Chan, et al., U.S. Appl. No. 11/117,760, filed Apr. 27, 2005, Dated Jun. 29, 2007.

U.S. Office Action for Chan, et al., U.S. Appl. No. 11/117,760, filed Apr. 27, 2005, Dated Aug. 20, 2007.

PCT International Preliminary Report on Patentability for Pacific Arrow Limited, et al., International Application No. PCT/US2006/016158, filed Apr. 27, 2006, Dated Oct. 30, 2007.

U.S. Office Action for Chan, et al., U.S. Appl. No. 11/117,745, filed Apr. 27, 2005, Dated Jan. 25, 2008.

U.S. Office Communication for Chan, et al., U.S. Appl. No. 11/117,760, filed Apr. 27, 2005, Dated Feb. 8, 2008.

U.S. Office Action for Mak, et al., U.S. Appl. No. 11/412,659, filed Apr. 27, 2006, Dated Feb. 20, 2008.

U.S. Office Action for Chan, et al., U.S. Appl. No. 11/289,142, filed Nov. 28, 2005, Dated Apr. 14, 2008.

U.S. Office Action for Chan, et al., U.S. Appl. No. 11/117,745, filed Apr. 27, 2005, Dated Mar. 12, 2007.

U.S. Office Action for Chan, et al., U.S. Appl. No. 11/117,745, filed Apr. 27, 2005, Dated Aug. 22, 2007.

PCT International Preliminary Report on Patentability issued on Feb. 7, 2006 for Pacific Arrow Limited, International App'l No. PCT/US2004/043465.

U.S. Office Action for Chan, et al., U.S. Appl. No. 10/906,303, filed Feb. 14, 2005, Dated Jan. 4, 2008.

PCT International Search Report issued on Jul. 7, 2008 for Pacific Arrow Limited, International App'l No. PCT/US08/02086.

PCT Written Opinion of the International Searching Authority issued on Jul. 7, 2008 for Pacific Arrow Limited, International App'l No. PCT/US US08/02086.

(56) References Cited

OTHER PUBLICATIONS

PCT International Search Report for Pacific Arrow Limited et al., International App'l No. PCT/US07/77273, filed Aug. 30, 2007, Dated Aug. 4, 2008.
PCT Written Opinion of the International Searching Authority for Pacific Arrow Limited et al., International App'l No. PCT/US07/77273, filed Aug. 30, 2007, Dated Aug. 4, 2008.
U.S. Advisory Action for Chan, et al., U.S. Appl. No. 11/289,142, filed Nov. 28, 2005, Dated Jul. 28, 2008.
Notice of Allowability for Chan et al., U.S. Appl. No. 10/906,303, filed Feb. 14, 2005, dated Nov. 26, 2008.
Notice of Allowability for Chan et al., U.S. Appl. No. 11/117,745, filed Apr. 27, 2005, dated Dec. 2, 2008.
Notice of Allowability for Chan et al., U.S. Appl. No. 11/289,142, filed Nov. 28, 2005, dated Oct. 1, 2008.
U.S. Office Action for Chan, et al., U.S. Appl. No. 11/117,760, filed Apr. 27, 2005, Dated Mar. 18, 2009.
U.S. Office Action for Chan, et al., U.S. Appl. No. 11/683,198, filed Mar. 7, 2007, Dated May 1, 2009.
U.S. Office Action for Mak, et al., U.S. Appl. No. 12/195,112, filed Aug. 20, 2008, Dated May 19, 2009.
PCT Written Opinion of the International Searching Authority for PCT/US09/34115, filed Feb. 13, 2009 for Pacific Arrow Limited et al., dated Jun. 2, 2009.
PCT Written Opinion of the International Searching Authority for PCT/US07/77273, filed Aug. 30, 2007 for Pacific Arrow Limited et al., dated Aug. 4, 2008.
PCT Written Opinion of the International Searching Authority, for PCT/US09/34115, filed Feb. 13, 2009 for Pacific Arrow Limited et al., dated Jun. 2, 2009.
PCT Preliminary Report on Patentability for PCT/US2007/077273, filed Aug. 30, 2007 for Pacific Arrow Limited et al., dated Mar. 12, 2009.
PCT Notification of Transmittal of International Preliminary Examination Report for PCT/IB02/04750, filed Aug. 28, 2002 for Fountain Silver Limited et al., dated Jun. 3, 2003.
U.S. Office Action for Chan, et al., U.S. Appl. No. 11/683,198, filed Mar. 7, 2007, Dated Feb. 18, 2010.
U.S. Office Action for Mak, et al., U.S. Appl. No. 12/195,112, filed Aug. 20, 2008, Dated Feb. 18, 2010.
PCT International Search Report for PCT/US2009/034115, filed Feb. 13, 2009 for Pacific Arrow Limited et al., dated Jun. 2, 2009.
PCT Preliminary Report on Patentability for PCT/US2009/034115, filed Feb. 13, 2009 for Pacific Arrow Limited et al., dated Aug. 26, 2010.
PCT Written Opinion of the International Searching Authority for PCT/US09/34115, filed Februaty 13, 2009 for Pacific Arrow Limited et al., dated Jun. 2, 2009.
PCT Written Opinion of the International Searching Authority for PCT/US10/42220, filed Jul. 16, 2010 for Pacific Arrow Limited et al., dated Sep. 2, 2010.
PCT International Search Report for PCT/US10/42240, filed Jul. 16, 2010 for Pacific Arrow Limited et al., dated Sep. 2, 2010.
U.S. Office Action for Chan, et al., U.S. Appl. No. 11/683,198, filed Mar. 7, 2007, Dated Sep. 10, 2008.
U.S. Office Action, Jan. 19, 2011, for Chan et al., U.S. Appl. No. 12/344,682, filed Dec. 29, 2008.
U.S. Office Action, May 20, 2011, for Chan et al., U.S. Appl. No. 12/392,795, filed Feb. 25, 2009.
Notice of Allowability for Chan et al., U.S. Appl. No. 11/683,198, filed Mar. 7, 2007, Dated May 5, 2011.
US Office Action, May 12, 2011, for Chan et al., U.S. Appl. No. 12/714,598, filed Mar. 1, 2010.
U.S. Office Action, Oct. 27, 2011, for Chan et al., U.S. Appl. No. 12/344,682, filed Dec. 29, 2008.
PCT Written Opinion of the International Searching Authority, Dec. 6, 2011, for Pacific Arrow Limited, Int'l App'l No. PCT/US2011/044233, filed Jul. 15, 2011.
PCT International Search Report Dec. 6, 2011, for Pacific Arrow Limited, Int'l App'l No. PCT/US2011/044233, filed Jul. 15, 2011.
U.S. Office Action, Dec. 28, 2011, for Chan et al., U.S. Appl. No. 12/714,598, filed Mar. 1, 2010.
U.S. Notice of Allowance, Jan. 30, 2012, for Chan et al., U.S. Appl. No. 11/683,198, filed Mar. 7, 2007.
U.S. Office Action, Mar. 20, 2012, for Chan et al., U.S. Appl. No. 12/344,682, filed Dec. 29, 2008.
U.S. Office Action, Apr. 17, 2012, for Chan et al., U.S. Appl. No. 12/392,795, filed Feb. 25, 2009.
Notice of Allowability for Chan et al., U.S. Appl. No. 12/392,795, filed Feb. 25, 2009, Dated Aug. 15, 2012.
PCT Written Opinion of the International Searching Authority, Oct. 2, 2012, for Pacific Arrow Limited, Int'l App'l No. PCT/US12/46716, filed Jul. 13, 2012.
PCT International Search Report, Oct. 2, 2012, for Pacific Arrow Limited, Int'l App'l No. PCT/US12/46716, filed Jul. 13, 2012.
U.S. Office Action, Oct. 15, 2012, for Chan et al., U.S. Appl. No. 13/259,480, filed Sep. 23, 2011.
Supplementary European Search Report issued on Jul. 6, 2005 for Fountain Silver Limited et al., European Patent Application No. 02781502.46.
European Office Communication for Wang, Yun, European App'l No. EP 02781502.6, filed Feb. 25, 2004, Dated Jul. 20, 2007.
European Office Communication for Wang, Yun, European App'l No, EP 02781502.6, filed Feb. 25, 2004, Dated Oct. 12, 2005.
Supplementary European Search Report issued on Oct 13, 2009 for Pacific Arrow Limited et al., European Patent Application No. 04815530.3, PCT/US2004043465.
Supplementary European Search Report issued on Oct 13, 2009 for Pacific Arrow Limited et al., European Patent Application No. 04809909.7, PCT/US2004033359.
Supplementary European Search Report issued on Oct 22, 2009 for Mak et al., European Patent Application No. 05810263.3, PCT/US2005031900.
European Office Communication for Pacific Arrow Limited, et al., European App'l No. EP 06751723.5-2123, Dated Jan. 15, 2010.
European Office Communication for Mak May Sung, et al., European App'l No. EP 0581026.3-2123, Dated Dec. 29, 2009.
European Communication for Pacific Arrow Limited, et al., European App'l No. EP 04809909.7-2123, Dated Apr. 19, 2010.
European Office Communication for Pacific Arrow Limited, et al., European App'l No. EP 04815530.3-2123, Dated Apr. 19, 2010.
European Office Communication for Mak May Sung, et al., European App'l No. EP 05810263.3-2123, Dated Apr. 19, 2010.
European Office Communication for Pacific Arrow Limited, et al., European App'l No. EP 07841638.5-2123, Dated Apr. 19, 2010.
European Office Communication, Feb. 13, 2012, for Pacific Arrow Limited, European App'l No. EP 07841638.5-2123, filed Mar. 27, 2009.
European Office Communication, Feb. 13, 2012 for Pacific Arrow Limited, European App'l No. E 05810263.3-2123, filed Mar. 30, 2007.
European Office Communication, Feb. 13, 2012, for Pacific Arrow Limited, European App'l No. EP 04815530.3-2123, filed Jul. 19, 2006.
European Office Communication, Mar. 3, 2012 for Pacific Arrow Limited, European App'l No. EP 04809909.7-2123, filed Mar. 27, 2006.
European Office Communication, Apr. 26, 2012 for Pacific Arrow Limited, European App'l No. EP 09721583.4-2123, filed Sep. 7, 2010.
European Office Communication, Jun. 4, 2012 for Pacific Arrow Limited, European App'l No. EP 02781502.6-2112, filed Feb. 25, 2004.
Notice of Acceptance for Wang, Yun, Australia Patent App'l No. 2002348988, filed Jan. 21, 2004, Dated Jul. 26, 2007.
Australian Office Action for Australian Patent No. 2004281707, Feb. 19, 2010, Pacific Arrow Limited.
Australian Office Action, Mar. 18, 2011 for Pacific Arrow Limited, Australian Patent Application No. 2004281707, filed Oct. 8, 2004.
Notice of Acceptance for Pacific Arrow Limited, Australian Patent App'l No. 2004281707, filed Mar. 23, 2006, Dated May 26, 2011.
Australian Office Action, Feb. 6, 2012 for Pacific Arrow Limited, Australian App'l No. 2009208069, filed Aug. 7, 2009.

(56) References Cited

OTHER PUBLICATIONS

Australian Office Action, Feb. 6, 2012 for Pacific Arrow Limited, Australian App'l No. 2005282437, filed Mar. 19, 2007.
Australian Office Action, Feb. 6, 2012 for Pacific Arrow Limited, Australian App'l No. 2009200988, filed Mar. 10, 2009.
Australian Office Action, Jun. 21, 2012 for Pacific Arrow Limited, Australian App'l No. 2008244648, filed Aug. 21, 2009.
Notice of Acceptance for Wang, Yun, New Zealand Patent No. App'l No. 530449, filed Jan. 6, 2004, Dated Jun. 29, 2007.
New Zealand Examination Report for Wang, Yun, New Zealand Patent No. App'l No. 530449, filed Jan. 6, 2004, Dated Feb. 15, 2006.
New Zealand Examination Report for Wang, Yun, New Zealand Patent No. App'l No. 530449, filed Jan. 6, 2004, Dated Apr. 10, 2007.
New Zealand Office Action, Aug. 12, 2009, New Zealand Application No. 546138, filed Mar. 22, 2007.
New Zealand Office Action, Sep. 22, 2009, New Zealand Application No. 546138, filed Mar. 27, 2006.
New Zealand Office Action, Mar. 7, 2011 for Pacific Arrow Limited, New Zealand App'l No. 587973, filed Sep. 14, 2010.
New Zealand Office Action, Apr. 12, 2011 for Pacific Arrow Limited, New Zealand App'l No. 554037, filed Mar. 19, 2007.
New Zealand Office Action, Sep. 24, 2010, for Pacific Arrow Limited, New Zealand App'l No. 579194, filed Aug. 21, 2009.
New Zealand Office Action, Jan. 11, 2012, for Pacific Arrow Limited, New Zealand App'l No. 579194, filed Aug. 21, 2009.
New Zealand Office Action, Mar. 26, 2012, for Pacific Arrow Limited, New Zealand App'l No. 598934, filed Mar. 21, 2012.
Japan Office Action, Nov. 4, 2008 for Fountain Silver Limited, Japan Patent Application No. 2003-522442, filed Aug. 28, 2002.
Japan Final Office Action, Feb. 23, 2009, for Fountain Silver Limited, Japan App'l No. 2003-522442, filed Feb. 5, 2004.
Japan Office Action, Jan. 14, 2011, for Pacific Arrow Limited, Japan App'l No. 2006-534419, filed Mar. 22, 2006.
Japan Office Action, Feb. 2, 2011, for Pacific Arrow Limited, Japan app'l No. 2006-534419, filed Mar. 22, 2006.
Japan Office Action, Mar. 18, 2011, for Pacific Arrow Limited, Japan app'l No. 2006-547422, filed Jun. 16, 2006.
Japan Office Action, Jun. 3, 2011 for Pacific Arrow Limited, Japan App'l No. 2006-534419, filed Mar. 22, 2006.
Japanese Notice of Allowance, Nov. 15, 2011, for Pacific Arrow Limited, Japanese app'l No. 2006-547422, filed Jun. 16, 2006.
Japanese Office Action, Nov. 21, 2011, for Pacific Arrow Limited, Japanese app'l No. 2007-530484, filed Mar. 2, 2007.
Japanese Office Action, May 8, 2012, for Pacific Arrow Limited, Japanese app'l No. 2007-530484, filed Mar. 2, 2007.
Korean Office Action, Nov. 21, 2008 for Fountain Silver Limited, Korean Application No. 10-2004-7002889, filed Aug. 28, 2002.
Korean Office Action, Jun. 3, 2011 for Pacific Arrow Limited, Korean App'l No. 10-2006-7008896, filed May 8, 2006.
Korean Office Action, Jun. 22, 2012 for Pacific Arrow Limited, Korean App'l No. 10-2007-7007902, filed Apr. 6, 2007.
Canadian Office Action, Nov. 7, 2008 for Fountain Silver Limited, Canadian Application No. 2,451,740, filed Dec. 18, 2003.
Canadian Office Action, May 26, 2010 for Fountain Silver Limited, Canadian Application No. 2,451,740, filed Dec. 18, 2003.
Canadian Office Action, Sep. 8, 2011, for Fountain Silver Limited et al., Canadian App'l No. 2,451,740, filed Dec. 18, 2003.
Canadian Notice of Allowance, Oct. 5, 2011, for Pacific Arrow Limited et al, Canadian App'l No. 2541425, filed Oct. 8, 2004.
Canadian Office Action, Jan. 31, 2012, for Pacific Arrow Limited, Canadian Application No. 2,579,231, filed Mar. 6, 2007.
Canadian Office Action, Jul. 5, 2012, for Fountain Silver Limited et al., Canadian App'l No. 2,451,740, filed Dec. 18, 2003.
Taiwan Office Action, Sep. 14, 2004 for Wang Yun, Taiwan Application No. 091119471, filed Aug. 28, 2002.
Taiwan Office Action, Apr. 26, 2005 for Wang Yun, Taiwan Application No. 091119471, filed Aug. 28, 2002.
Taiwan Office Action, Mar. 12, 2010 for Pacific Arrow Limited, Taiwan App'l No. 093140030, filed Dec. 22, 2004.
Taiwan Office Action, Mar. 3, 2011 for Pacific Arrow Limited, Taiwan App'l No. 093140030, filed Dec. 22, 2004.
Taiwan Office Action, Jan. 18, 2012 for Pacific Arrow Limited, Taiwan App'l No. 094130519, filed Sep. 6, 2005.
Chinese Office Action, Aug. 27, 2004 for Wang Yun, Chinese Publication No. CN 1236792C, filed Aug. 28, 2002.
Chinese Office Action, May 27, 2005 for Wang Yun, Chinese Publication No. CN 1236792C, filed Aug. 28, 2002.
Chinese Office Action, Jan. 15, 2010 for Pacific Arrow Limited, et al., Chinese App'l No. 200480036761.7, filed Jun. 8, 2006.
Chinese Office Action, Mar. 27, 2009 for Pacific Arrow Limited, Chinese application No. 2005800375247, filed Jul. 26, 2007.
Chinese Office Action, Apr. 21, 2010 for Pacific Arrow Limited, Chinese application No. 2005800375247, filed Jul. 26, 2007.
Chinese Office Action, Jun. 3, 2011 for Pacific Arrow Limited, Chinese application No. 200880012065.0, filed Oct. 14, 2009.
Chinese Office Action, Jun. 14, 2011, for Pacific Arrow Limited, Chinese App'l No. 200480036761.7, filed Jun. 8, 2006.
Chinese Office Action, Oct. 28, 2011, for Pacific Arrow Limited, Chinese App'l No. 200480038698.0, filed Jun. 23, 2006.
Chinese Office Action, Sep. 28, 2011, for Pacific Arrow Limited, Chinese App'l No. 200480036761.7, filed Jun. 8, 2006.
Chinese Office Action, Mar. 23, 2011, for Pacific Arrow Limited, Chinese App'l No. 200780040744.4, filed Apr. 30, 2009.
Chinese Notice of Allowance, Feb. 1, 2011, for Pacific Arrow Limited, Chinese app'l No. 200580037524.7, filed Apr. 30, 2007.
Chinese Office Action, Apr. 9, 2012, for Pacific Arrow Limited, Chinese App'l No. 200780040744.4, filed Apr. 30, 2009.
Arda, et al. "Saniculoside N from Sanicula europaea L." Journal of Natural Products (1997), 60(11), 1170-1173.
Azam, et al. "A triterpenoidal sapogenin from the seeds of Dodonaea viscose Linn." Indian Journal of Chemistry, Section B: Organic Chemistry Including Medicinal Chemistry (1993), 32B(4), 513-14.
Barre, et al. "A bioactive triterpene from Lantana camara." Phytochemistry (1997), 45(2), 321-324.
Barua, et al. "Triterpenoids. XXIX. Structure of barringtogenol B-a new triterpenoid sapogenin from Barringtonia acutangula." Tetrahedron (1968), 24(3), 1113-17.
Beeby, et al. "Angeloyl chloride: synthesis and utilization in the partial synthesis of lantadene A (rehmannic acid)." Tetrahedron Letters (1977), (38), 3379-82.
Brown, et al. "The relation of chemical structure to the icterogenic and photosensitizing action of some naturally occurring and synthetic triterpene acids." South African Journal of Laboratory and Clinical Medicine (1963), 9 262-72.
Brown, et al. "Biliary excretion in the rabbit. II. The relation between the chemical structure of certain natural or synthetic pentacyclic triterpenes and their icterogenic activity. 2. The substituents on carbon atoms 17, 29, 20, and 22." Proc. Roy. Soc. (London) Ser. B (1964), 160(979), 246-57.
Chen, et al. "Studies on the constituents of Xanthoceras sorbifolia Bunge. (I)."Shoyakugaku Zasshi (1984), 38(2), 203-6.
Chen, et al. Studies on the constituents of Xanthoceras sorbifolia Bunge. II. Major sapogenol and a prosapogenin from the fruits of Xanthoceras sorbifolia Bunge. Chemical & pharmaceutical bulletin (Sep. 1984), 32(9), 3378-83.
Chen, et al. "Studies on the constituents of Xanthoceras sorbifolia Bunge. III. Minor prosapogenins from the fruits of Xanthoceras sorbifolia Bunge." Chemical & Pharmaceutical Bulletin (1985), 33(1), 127-34.
Chen, et al. "Studies on the constituents of Xanthoceras sorbifolia Bunge. IV. Structures of the minor prosapogenins." Chemical & Pharmaceutical Bulletin (1985), 33(3), 1043-8.
Chen, et al. "Studies on the constituents of Xanthoceras sorbifolia Bunge. V. Major saponins from the fruits of Xanthoceras sorbifolia Bunge." Chemical & Pharmaceutical Bulletin (1985), 33(4), 1387-94.
Cheng, et al. "Two new sterols in husk of Xanthoceras sorbifolia." Zhongcaoyao (2001), 32(3), 199-201.
Chakravarty, et al. "Triterpenoid prosaponins from leaves of Maesa chisia var. angustifolia." Phytochemistry (1987), 26(8), 2345-9.

(56) References Cited

OTHER PUBLICATIONS

Cui, et al. "2D NMR structure determination of five flavonoids from the wood of Xanthoceras sorbifolia Bunge." Shenyang Yaoxueyuan Xuebao (1991), 8(1), 36-8, 57.

Cui, et al. "Blood-activating constituents of Wenguanmu (Xanthoceras sorbifolia)." Zhongcaoyao (1987), 18(7), 297-8, 296.

Cui, et al. "The application of the microcomputer in the study of Chinese herb and natural drugs. 1. The BASIC program used for the design of liquid-liquid extraction and forecasting the results of extraction and separation." Shenyang Yaoxueyuan Xuebao (1986), 3(2), 79-84.

Eakins, et al. "The effect of three triterpene acids and sporidesmin on the enzyme activities of rat liver plasma membranes." Chemico-Biological Interactions (1978), 21(1), 117-24.

Eakins, et al. "Studies on bile secretion with the aid of the isolated perfused rat liver. II. The effect of two further pentacyclic triterpenes, asiatic acid and 22-angeloyloxyoleanolicacid." Chemico-Biological Interactions (1978), 21(1), 79-87.

Hart, et al. "New triterpenes of Lantana camara. A comparative study of the constituents of several taxa." Australian Journal of Chemistry (1976), 29(3), 655-71.

Hopkins, et al. "Eicosenoic acid and other fatty acids of Sapindaceae seed oils." Lipids (1967), 2(3), 258-60.

Hu, et al. "Preparation of high-heating value synthetic liquid fuels." Faming Zhuanli Shenqing Gongkai Shuomingshu (1999), 4 pp.

Hu, et al. "Preparation of liquid fuels having high caloric value." Faming Zhuanli Shenqing Gongkai Shuomingshu (1994), 5 pp.

Huang, et al. "Chemical constituents of Wenguanmu (Xanthoceras sorbifolia) (I)."Zhongcaoyao (1987), 18(5), 199-202.

Huang, et al. "Preliminary studies on absorption and accumulation of atmospheric lead and cadmium by woody plants." Linye Kexue (1982), 18(1), 93-7.

Kim, et al. "Fatty-acid composition of vegetable oils." Choson Minjujuui Inmin Konghwaguk Kwahagwon Tongbo (1985), (3), 43-6.

Koike, et al. "New triterpenoid saponins from Maesa japonica." Journal of Natural Products (1999), 62(2), 228-232.

Kuang, et al. "Anti-inflammatory effects of n-butanol extract of Xanthoceras sorbifolia Bunge." Shenyang Yaoke Daxue Xuebao (2001), 18(1), 53-56.

Li, et al. "Medicine for enhancing mental activity." Faming Zhuanli Shenqing Gongkai Shuomingshu (1994), 7 pp.

Li, et al. "xanthoceras sorbifolia fruit extracts for enhancing mental activity." Faming Zhuanli Shenqing Gongkai Shuomingshu (1994), 6 pp.

Li, et al. "Identification of fatty acids in the kernel oil of Xanthoceras sorbifolia Bge. with GC-MS." Zhiwu Ziyuan Yu Huanjing (1993), 2(2), 28-32.

Li, et al. "Isolation and structural determination of triterpene alcohols and 4-methylsterols in unsaponifiable fraction of the oil from Xanthoceras sorbifolia Bge." Linye Kexue (1984), 20(4), 397-402.

Li, et al. "Eremophilenolides and other constituents from the roots of Ligularia sagitta." Planta Medica (2003), 69(4), 356-360.

Li, et al. "New guaianolides and xanthine oxidase inhibitory flavonols from Ajania fruticulosa." Journal of Natural Products (1999), 62(7), 1053-1055.

Liu, et al. "The components of Cecelia tangutica." Bulletin of the Korean Chemical Society (2004), 25(7), 1078-1080.

Ma, et al. "A novel protoilludane sesquiterpene from the wood of Xanthoceras sorbifolia." Chinese Chemical Letters (2004), 15(1), 65-67.

Ma, et al. "Screening of Chinese and Mongolian herbal drugs for anti-human immunodeficiency virus type 1 (HIV-1) activity." Phytotherapy Research (2002), 16(S1), 186-189.

Ma, et al. "Inhibitory effects on HIV-1 protease of constituents from the wood of Xanthoceras sorbifolia." Journal of natural products (Feb. 2000), 63(2), 238-42.

Mahato, et al. "New triterpenoids from Lantana camara: Isomerisation of the angeloyl moiety of lantadene a during catalytic hydrogenation." Journal of the Indian Chemical Society (1999), 76(11-12), 723-726.

Meng, et al. "Antifungal highly oxygenated guaianolides and other constituents from Ajania fruticulosa." Phytochemistry (2001), 58(7), 1141-1145.

Nakamura, et al. "Inhibitory effects of some traditional medicines on proliferation of HIV-1 and its protease." Yakugaku Zasshi (2004), 124(8), 519-529.

Nethaji, et al. "Molecular structure of lantadene-B&C, triterpenoids of Lantana camara, red variety: lantadene-B, 22□-angeloyloxy-3-oxoolean-12-en-28-oic acid; lantadene-C, 22□-(S)-2'-methyl butanoyloxy-3-oxoolean-12-en-28-oic acid." Journal of Crystallographic and Spectroscopic Research (1993), 23(6), 469-72.

Plouvier, et al. "Fraxoside and coumarin heterosides occurring in various botanical groups."Comptes Rendus des Seances de l'Academie des Sciences, Serie D: Sciences Naturelles (1968), 267(22), 1883-5.

Plouvier, et al. Flavone heterosides: kaempferol 3-rhamnoglucoside, myricitrin, linarin, and saponarin. Comptes Rendus des Seances de l'Academie des Sciences, Serie D: Sciences Naturelles (1966), 262(12), 1368-71.

Plouvier, et al."Oil of the seeds of Xanthoceras sorbifolia Bunge and of Koelreuteria paniculata Laxm." Compt. rend. (1946), 222 916-17.

Sakurai, et al. "Assamicin I and II, novel triterpenoid saponins with insulin-like activity from Aesculus assamica Griff." Bioorganic & Medicinal Chemistry Letters (2002), 12(5), 807-810.

Semikhov, et al. "Comparative study of the amino acid composition of the embryo in grasses (Poaceae) and other flowering plants." Botanicheskii Zhurnal (Sankt-Peterburg, Russian Federation) (1994), 79(3), 83-92.

Sharma, et al. "Molecular structure, polymorphism, and toxicity of lantadene A, the pentacyclic triterpenoid from the hepatotoxic plant Lantana camara." Journal of biochemical toxicology (1991 Spring), 6(1), 57-63.

Shang-Jiang, et al. "Constituents of Shashen (Adenophora axilliflora)." Planta Medica (1986), (4), 317-20.

Sindambiwe, et al. "Triterpenoid saponins from Maesa lanceolata." Phytochemistry (1996), 41(1), 269-77.

Singh, et al. "Biotransformation of lantadene A (22□-angeloyloxy-3-oxoolean-12-en-28-oic acid), the pentacyclic triterpenoid, by Alcaligenes faecalis." Biodegradation (1999), 10(5), 373-381.

Tian, et al. "Study on the vegetative storage proteins in temperate hardwoods of fifteen families." Xibei Zhiwu Xuebao (2000), 20(5), 835-841.

Triterpenoids. XVI. The constitution of rehmannic acid. Journal of the Chemical Society, Abstracts (1954), 900-3.

Tuntiwachwuttikul, et al. "A triterpenoid saponin from Maesa ramentacea." Phytochemistry (1997), 44(3), 491-495.

Voutquenne, et al. Triterpenoid saponins and acylated prosapogenins from Harpullia austro-caledonica. Phytochemistry (2002), 59(8), 825-832.

Wang, et al. "Chemical constituents of the oil and kernels of Xanthoceras sorbifolia Bunge." Zhiwu Xuebao (1981), 23(4), 331-3.

Waechter, et al. "Antitubercular Activity of Triterpenoids from Lippia turbinata." Journal of Natural Products (2001), 64 (1), 37-41.

Yan, et al. "Separation, identification and determination of the unsaponifiable matters in vegetable oils." Beijing Shifan Daxue Xuebao, Ziran Kexueban (1985), (1), 53-8.

Yan, et al. "Isolation, content analysis and structural determination of sterols in unsaponifiable fraction of the oil from Xanthoceras sorbifolia Bge." Linye Kexue (1984), 20(4), 389-96.

Yang, et al. "Extraction of total saponin, fat, protein, and saccharide from Xanthoceras sorbifolia." Faming Zhuanli Shenqing Gongkai Shuomingshu (2002), 4 pp.

Yang, et al. "Application of the extract of Xanthoceras sorbifolia shell in preparing the food and medicine for improving brain functions." Faming Zhuanli Shenqing Gongkai Shuomingshu (2002), 6 pp.

Yang, et al. "Two new triterpenoid saponins from the seeds of Aesculus chinensis." Chinese Chemical Letters (2000), 11(2), 139-142.

(56) References Cited

OTHER PUBLICATIONS

Zhang, et al. "Quantitative determination of myricetin and quercetin in Xanthoceras sorbifolia Bunge by HPLC." Shenyang Yaoke Daxue Xuebao (2000), 17(3), 194-196.

Zhang, et al. "Studies on chemical constituents of Xanthoceras sorbifolia Bunge." Yaoxue Xuebao (2000), 35(2), 124-127.

Zhao, et al. "Four new triterpene saponins from the seeds of Aesculus chinensis." Journal of Asian Natural Products Research (2003), 5(3), 197-203.

Zhao, et al. "Three new triterpene saponins from the seeds of Aesculus chinensis." Chemical & Pharmaceutical Bulletin (2001), 49(5), 626-628.

Zheng, et al. "Triterpenoids from Mosla chinensis." Indian Journal of Chemistry, Section B: Organic Chemistry Including Medicinal Chemistry (2000), 39B(11), 875-878.

Aper, et al. "New acylated triterpenoid saponins from Maese lanceolate." Phytochemistry 52 (1999) 1121-1131.

D'Aoquarica, et al. "Isolation and structure elucidation of four new triterpenoid estersaponins from fruits of Pittosporum tobira AIT." Tetrahedron 58 (2002) 10127-10136.

Jiang. et al. "Six Triterpenoid Saponins from Maesa Laxiflora." J. Nat. Prod. 1999. 62, 873-876.

Lu, et al. " Triterpenoid saponins from the roots of tea plants (Camellia sinensis var. assamica)." Phytochemistry 53 (2000) 941-946.

Seo, et al. "A New Triterpene Saponin from Pittosporum viridlflorum from the Madagascar Rainforest." J. Nat. Prod. 2002, 65, 65-68.

Yang, et al. "Anti-HIV-1 Protease Triterpenoid Saponins from the Seeds of Aesculus chinensis." J. Nat. Prod. 1999, 62, 1510-1513.

Oda, K. et al., "Adjuvant and Haemolytic Activities of 47 Saponins Derived from Medicinal and Food Plants" Biol. Chem. (2000) vol. 381, pp. 67-74.

Chan, Pui-Kwong, 2007, "Acylation with diangeloyl groups at C21-22 positions in triterpenoid saponins is essential for cytotoxcity towards tumor cells", Biochemical Pharmacology 73(2007): 341-350.

Lavaud, et al., 1992, "Saponins from Steganotaenia Araliacea", Phycochemistry, 31(9):3177-3181.

Zhang, et al., 2007, "Cytotoxic triterpenoid saponins from the fruits of Aesculus pavia L", Phytochemistry 68(2007): 2075-2086.

Li, et al., 2005, "Two New Triterpenes from the Husks of Xanthoceras Sorbifolia", Planta Medica, vol. 71:1068-1070.

The Merck Manual of Diagnosis and Therapy, 17th Edition, 1999, Published by Merck Research Lanoratories, pp. 397-398, 948-949, 1916, and 1979-1981.

The Oxford Textbook of Oncology, 1995, published by Oxford University Press, pp. 447-453.

Voutquenne, et al., 2005, "Haemolytic Acylated Triterpenoid saponins from Harpullia austro-caledonica". Phytochemistry, vol. 66: 825-826.

Ma, et al, 2008, "Cytotoxic Triterpenoid Saponins Acylated with Monoterpenic Acid from Pithecellobium lucidum", Journal of Natural Products, vol. 71(1): 41-46.

Ushijima, et al, 2008, "Triterpene Glycosides from the Roots of Codonopsis lanceolate", Chemical & Pharmaceutical Bulletin, vol. 56(3) 308-314.

Yadava, et al., 2008, "New antibacterial triterpenoid saponin from Lactuca scariola", Fitoterapia, vol. 1:1-5.

Wang, et al., 2008, "Bioactive Triterpene Saponins from the Roots of Phytolacca Americana", Journal of Natural Products, vol. 71(1): 35-40.

Chang, et al, 2007, "Biologically Active Triterpenoid Saponins from Ardisia japonica", Journal of Natural Products, vol. 70(2): 179-187.

Akihisa et al, 2006, "Cancer Chemopreventive Effects and Cytotoxic Activities of the Triterpene Acids from the Resin of Boswellia carteri", Biological & Pharmaceutical Bulletin, vol. 29(9):1976-1979.

Liang, et al., 2006, "Triterpenoid Saponins from Lysimachia davurica", Chemical & Pharmaceutical Bulletin, vol. 54 (10):1380-1383.

Fujioka, et al., 2006, "Antiproliferative Constituents from Umbelliferae Plants. New Triterpenoid Glycosides from the Fruits of Bupleurum rotundifolium", Chemical & Pharmaceutical Bulletin, vol. 54 (12):1694-1704.

Rabi, et al., 2007, "Novel triterpenoid 25-hydroxy-3-oxoolean-12-en-28-oic acid induces growth arrest and apoptosis in breast cancer cells", Breast Cancer Research & Treatment, vol. 101:27-36.

Sporn, et al., 2007, "Platforms and Networks in Triterpenoid Pharmacology", Drug Development Research, vol. 68:174-182 (2007).

Puiffe, et al., 2007, "Characterization of Ovarian Cancer Ascites on Cell Invasion, Proliferation, Spheroid Formation, and Gene Expression in an in Vitro Model of Epithelial Ovarian Cancer" Neoplasia, vol. 9(10):820-829.

Ricciardelli, et al., 2006, "Extracellular Matrix of Ovarian Tumors", Seminars in Reproductive Medicine, vol. 24(4): 270-282.

Bang, et al., 2007, "Facile Synthesis of Trisaccharide Moiety Corresponding to Antitumor Activity in Triterpenoid Saponins Isolated from Pullsatilla Roots", Chemical & Pharmaceutical Bulletin, vol. 55(12): 1734-1739.

Talmadge, James E., 2008, "Follistatin as an Inhibitor of Experimental Metastasis", Clinical Cancer Research, vol. 14(3) 624-626.

Wei, et al., 2004, "Anti-inflammatory Triterpenoid Saponins from the Seeds of Aesculus chinensis", Chemical & Pharmaceutical Bulletin, vol. 52(10): 1246-1248.

Zhu et al, "Preliminary test of chemical constituents of wenguanguo and its multipurpose utilization", Research of Land and Natural Resources (1): 69-71, 1997.

Konoshima, et al. "Antitumor Agents, 82. Cytotoxic Sapogenols from Aesculus Hippocastanum", Journal of Natural Products vol. 49, No. 4, pp. 650-656, Jul.-Aug. 1986.

2006 Chemical Abstracts Catalog, published 2006 by Chemical Abstracts Service, p. 52.

Maes, et al. "In vitro and in vivo activities of a triterpenoid saponin extract (px-6518) from the plant Maesa balansae against visceral leishmania species." Antimicrobial agents and chemotherapy, Jan. 2004, p. 130-136.

Murakami, et al. "New hypoglycemic constituents in "gymnemic acid" from gymnema sylvestre." Chem. Pharm. Bull. 44(2) 469-471 (1996).

Na, et al. "Protein tyroshine phosphatase 1B inhibitory activity of triterpenes isolated from astilbe koreana." Bioorg Med Chem Lett. 2006 Jun 15;16(12): 3273-6.

Zhou, et al. "The first naturally occurring tie2 kinase inhibitor." Org Lett. Dec. 13, 2001;3(25): 4047-9.

Apers Sandra et al., "Antiviral, haemolytic and molluscicidal activities of triterpenoid saponins from Maesa lanceolata: Establishment of structure-activity relationships", Planta Medica, vol. 67, No. 6, Aug. 2001, pp. 528-532.

Ahmad V U et al., "The Sapogenins from Dodonaea-Viscosa", Fitoterapia, vol. 58, No. 5, 1987, pp. 361-362.

Dizes C et al., " Harpuloside a triterpenoid saponin from Harpullia ramiflora", Phytochemistry, Pergamon Press, GB, vol. 48, No. 7, Aug. 1, 1998, pp. 1229-1232.

Cheng, et al. "Two new sterols in the husk of Xanthoceras sorbifolia." Chinese Traditional and Herbal Drugs (2001), 32 (3), 199-201.

Yang et al. "The Influence of aquaporin -1 and microvessel density on ovarian carcinogenesis and ascites formation", International Journal of Gynecological Cancer, vol. 16, No. 51, Feb. 1, 2006, pp. 400-405.

Germonprez N. et al. "In vitro and in vivo anti-leishmanial activity of triterpenoid saponins isolated from Maesa balansae and some chemical derivatives", Journal of Medicinal Chemistry, vol. 48 No. 1 (Jan. 13, 2005), p. 32-37.

Dan Peer, et al. "Nanocarriers as an emerging platform for cancer therapy." Nature Publishing Group (2007), 751-760.

Mahato et al. Tetrahedron 1991 (47) 5215-5230.

Sheng-Xiang et al. Phytochemistry (1993), 34(5), 1385-1387.

\* cited by examiner

Inhibition of Fibronectin Secretion by Xanifolia-Y (Western blot) F 1

Figure 3
Inhibition of Fibronectin Secretion by Xanifolia-Y (Western blot)

A: Experiment (F23)

D

Increase Synthesis of Angiopoietin-2 in ES2 cells by Xanifolia-Y Treatment

Figure 6
Tumor Section
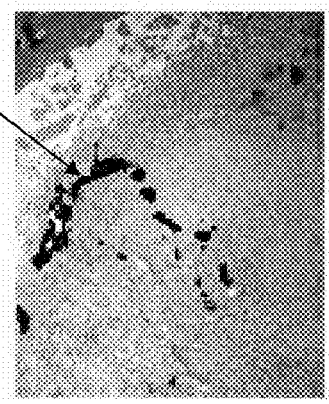
A — Control ES#1
Micro blood vessel (enhanced RBC stain)
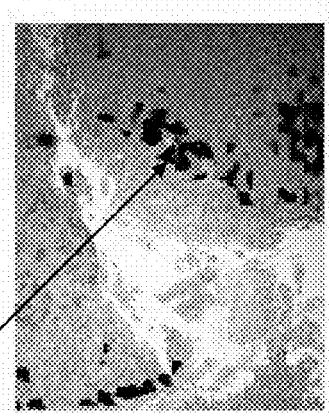
B — Control ES#3
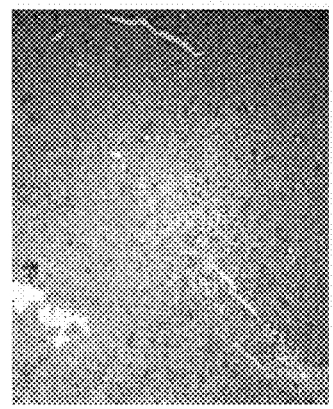
C — Day10 ES#2
D — Day10 ES#5

BLOCKING THE MIGRATION OR METASTASIS OF CANCER CELLS BY AFFECTING ADHESION PROTEINS AND THE USES OF NEW COMPOUNDS THEREOF

This application is a Continuation-in-Part of International Application No. PCT/US2008/002086 filed Feb. 15, 2008, which is a Continutation-in-part of International Application No. PCT/US2007/077273, filed Aug. 30, 2007, and claims benefit of U.S. Ser. No. 60/890,380, filed on Feb. 16, 2007, U.S. No. 60/947,705, filed Jul. 3, 2007, and U.S. Ser. No. 11/683,198, filed Mar. 7, 2007, which claims benefit of U.S. Ser. Nos. 60/795,417, filed Apr. 27, 2006, 60/841,727, filed Sep. 1, 2006, 60/890,380, filed Feb. 16, 2007, and is a Continuation-in-part of International Application No. PCT/US2006/016158, filed Apr. 27, 2006, which is a continuation-in part of International Application No. PCT/US05/31900, filed Sep. 7, 2005 (which claims benfit of U.S. Ser. Nos. 60/617,379, filed Oct. 8, 2004, 60/613,811, filed Sep. 27, 2004, and 60/607,858, filed Sep. 7, 2004); International Application No. Pct US/2006/016158 is also a Continuation-in-part of U.S. Ser. No. 11/117/,760 filed Apr. 27, 2005 now U.S. Pat. No. 7,727,561, and U.S. Ser. No. 11/131,551, filed May 17, 2005 now U.S. Pat. No. 7,762,285, which is a Continuation-In-Part of U.S. Ser. No. 11/117,745, filed Apr. 27, 2005 now U.S. Pat. No. 7,514,412. This application is also a Continuation-in-part of U.S. Ser. No. 12/392,795, filed Feb. 25, 2009 now U.S. Pat. No. 8,334,269, which is a continuation of U.S. Ser. No. 10/906,303, filed Feb. 14, 2005 now U.S. Pat. No. 7,524,824; International Application No. PCT/US09/34115 filed Feb. 13, 2009, U.S. Ser. No. 12/344,682, filed Dec. 29, 2008, which is a Continuation of U.S. Ser. Nos. 11/289,142, filed Nov. 28, 2005 now U.S. Pat. No. 7,488,753, and Ser. No. 11/267,523, filed Nov. 4, 2005 now abandoned; U.S. Ser. No. 12/195,112 filed Aug. 20, 2008, and U.S. Ser. No. 11/117,760, filed Apr. 27, 2005. The contents of these preceding applications are hereby incorporated in their entireties by reference into this application.

FIELD OF THE INVENTION

This invention provides methods and compositions for affecting the gene expression in cells as a result that cure diseases, wherein the methods comprise reducing the syndrome of diseases. In an embodiment the method comprise inhibition of gene expression. In an embodiment the method comprises stimulating the gene expression.

This invention provides methods, processes, compounds and compositions for modulating the gene expression or secretion of adhesion proteins or their receptors to cure disease, wherein the modulating comprises positive and negative regulating; wherein comprises inhibiting cancer growth, wherein the adhesion proteins or receptors comprise fibronectin, integrins family, Myosin, vitronectin, collagen, laminin, Glycosylation cell surface proteins, polyglycans, cadherin, heparin, tenascin, CD 54, CAM, elastin and FAK.

BACKGROUND OF THE INVENTION

Metastasis is the late stage of cancer in which cancer cells leave the original tumor site and migrate to other parts of the body. The cancer cells break away from the primary tumor and attach to the surrounding extracellular matrix and migrate to other parts of the body via bloodstream or the lymphatic system. The adhesion protein plays an essential role in cancer metastasis.

When metastasis occurs, there are numbers of way with which it can be treated, including radiosurgery, chemotherapy, radiation therapy, biological therapy hormone therapy, surgery and laser-immunotherapy. However, these are often not able to prevent the genesis of metastatic cancer.

SUMMARY OF THE INVENTION

This invention provide methods and compositions for modulating the secretion, expression, or synthesis of adhesion protein or angiopoietin of cancer cell and block their migration, metastasis or inhibit the growth of cancers or anti-angiogenesis, wherein the adhesion protein and their receptors comprise fibronectin, integrins family, Myosin, vitronectin, collagen, laminin, Glycosylation cell surface proteins, polyglycans, cadherin, heparin, tenascin, CD 54, CAM, elastin and FAK.

This invention provides a method of reducing the adhesion protein in cell and blocks the migration, metastasis of cancer cells or inhibits the growth of cancers or anti-angiogenesis, wherein the adhesion proteins or its receptors comprise fibronectin, integrins family, Myosin, vitronectin, collagen, laminin, Glycosylation cell surface proteins, polyglycans, cadherin, heparin, tenascin, CD 54, CAM, elastin and FAK. In an embodiment, this invention provides a method of reducing the secretion of fibronectin. In an embodiment, this invention provides a method for inhibiting the expression of adhesion proteins, wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK. This invention provides a method of inhibiting the growth, migration, metastasis of cancer by altering the characteristics of membrane of cancer cells, wherein the characteristics comprise adhesion protein; wherein the cancers comprise breast, leukocyte, liver, ovarian, bladder, prostate, skin, bone, brain, leukemia, lung, colon, CNS, melanoma, renal and cervix cancer.

DETAILED DESCRIPTION OF THE FIGURES

FIG. 1: Time studies of inhibition of Fibronectin secretion from cancer cells (ES2) after incubation of Xanifolia-Y. Fibronectin released in culture medium was determined by Western blot A: (results of experiment F1) Y is Xanifolia compound Y; B: (results of experiment F3); C: (results of experiment F4)

Figure 2:
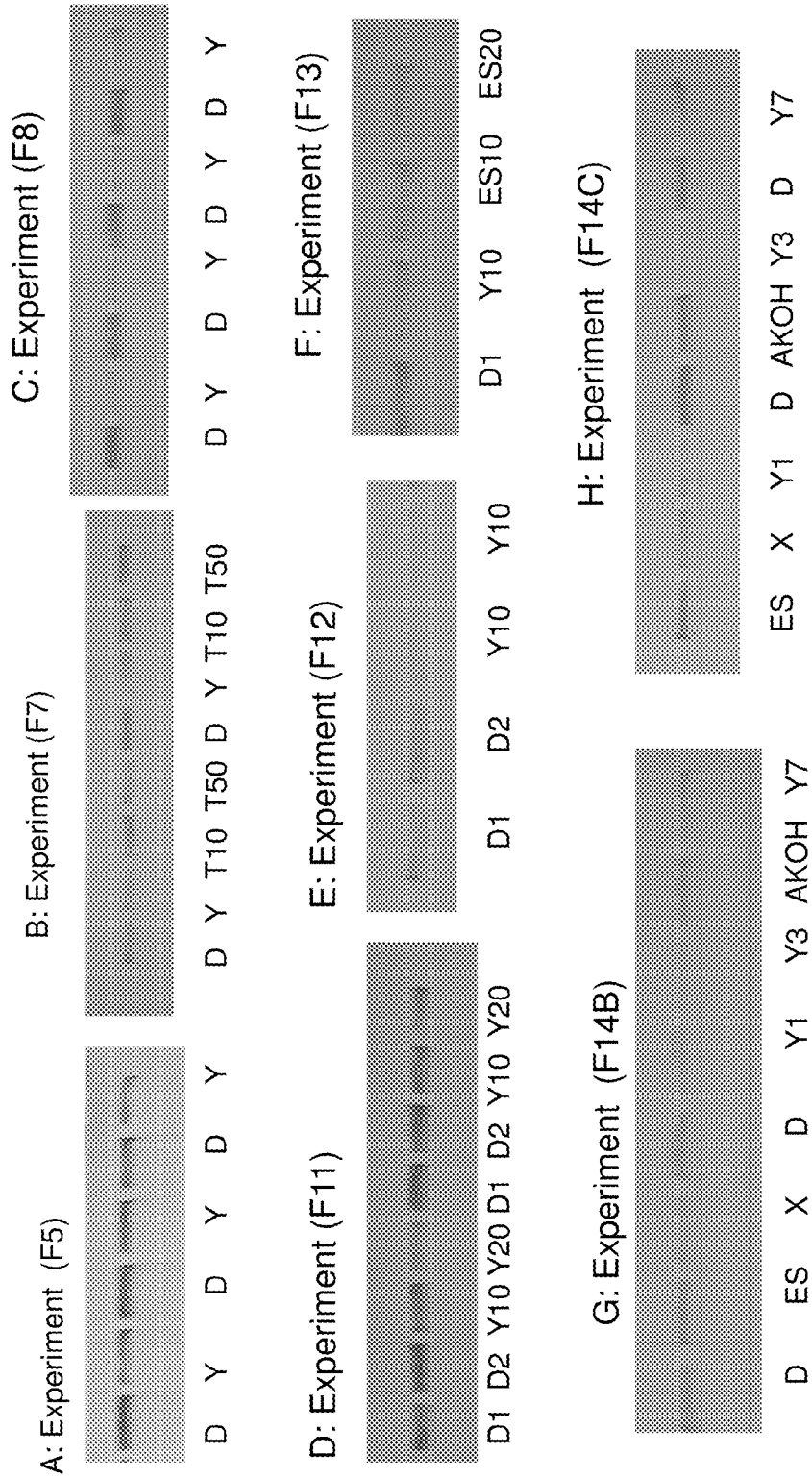

FIG. 2: Inhibition of Fibronectin Secretion by Xanifolia-Y (Western Blot). A: result of experiment F5; B: result of experiment F7; C: result of experiment F8; D: result of experiment F11; E: result of experiment F12; F: result of experiment F13; G: result of experiment F14B; H: result of experiment 14C FIG. 3: Inhibition of Fibronectin Secretion by Xanifolia-Y (Western Blot). A: result of experiment F23; B: result of experiment F24; C: result of experiment F26; D: result of experiment F27; E: result of experiment F29; F: result of experiment F28.

Figure 4:
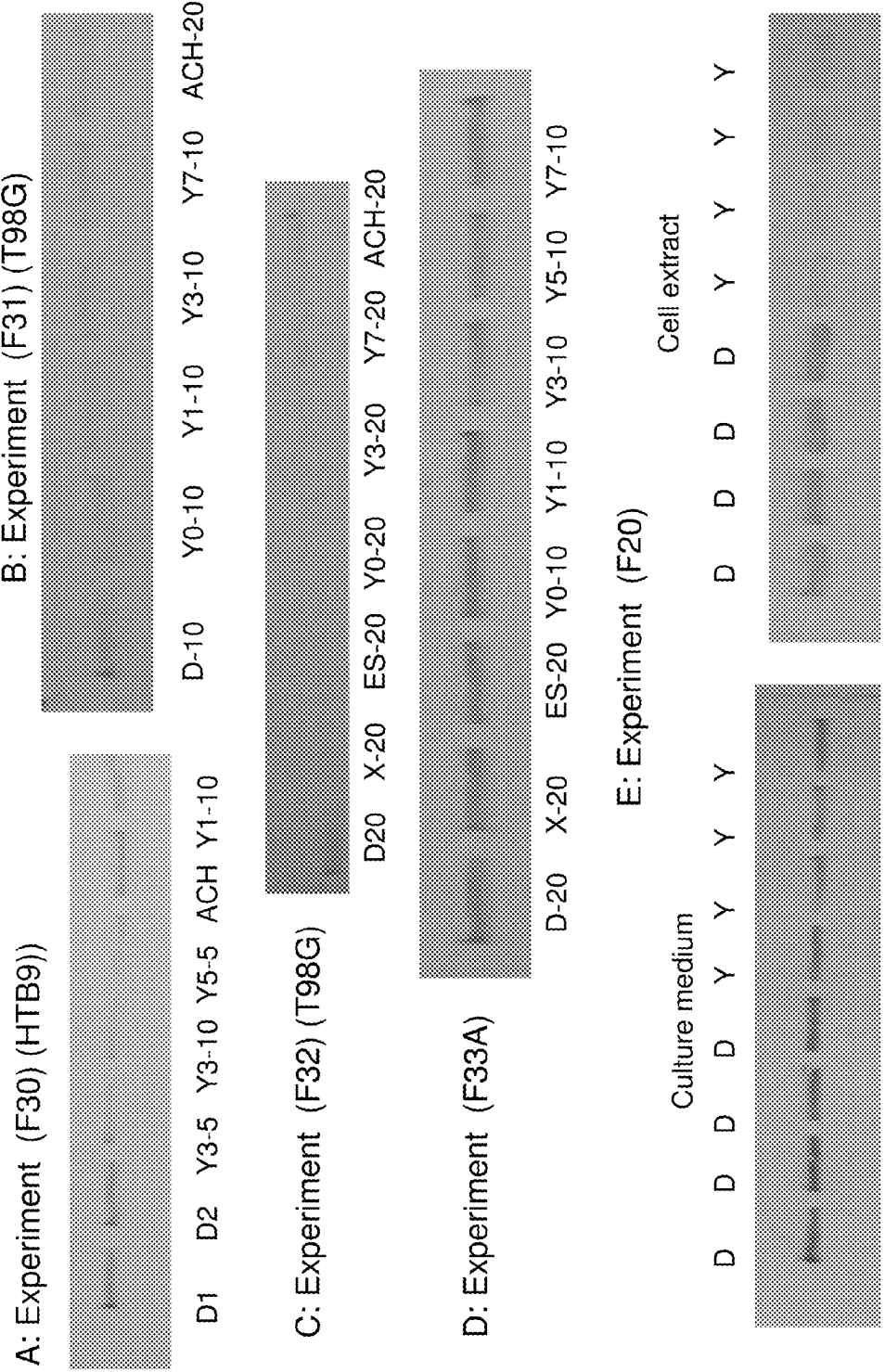

FIG. 4: Inhibition of Fibronectin Secretion by Xanifolia-Y (Western Blot). A: result of experiment F30; B: result of experiment F31; C: result of experiment F32; D: result of experiment F33A; E: result of experiment F20.

Figure 5:
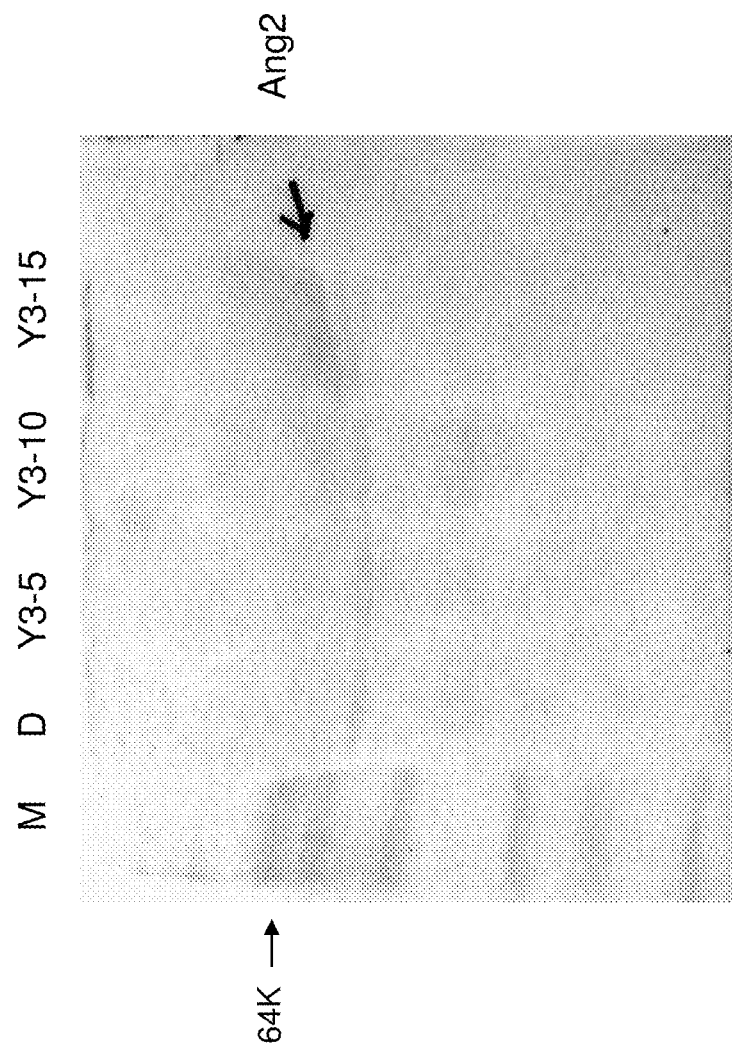

FIG. 5: Increase synthesis of Angiopoietin-2 in ES2 cells by Xanifolia-Y treatment.

FIG. 6: Analysis of genesis of blood vessel in xenograft tumor treated with compound Y. Figure A and B show the tumor sections taking from mice without Xanifolia Y treatment. Figure C and B show the tumor sections taking from mice with Xanifolia Y treatment. More blood vessels were observed in the control Group 1 than those in the drug-treated Group 2

DETAILED DESCRIPTION OF THE INVENTION

This invention provides methods and compositions for modulating the gene expression to cure diseases or reduce the syndrome of diseases, wherein the modulating comprises positive and negative regulating. In an embodiment, the method comprises inhibiting the gene expression. In an embodiment the method comprises stimulating the gene expression.

This invention provides methods and compositions for inhibiting the migration, metastasis or growth of cancers or anti-angiogenesis, wherein the methods comprise affecting the gene expression, wherein comprise affecting the adhesion proteins or their receptors, reducing adhesion protein, or inhibiting the synthesis, expression or secretion of adhesion proteins, wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK.

This invention provides methods and compositions for inhibiting the migration, metastasis or growth of cancers or anti-angiogenesis, wherein the methods comprise affecting the gene expression, wherein comprises stimulating the gene expression.

This invention provides a method for altering the characteristic of cancer cell membrane resulting in blocking the migration, metastasis of cancer cells or inhibit the growth of cancers or anti-angiogenesis, wherein the method comprises reducing adhesion proteins or their receptors, wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK.

This invention provides methods, processes, compounds and compositions of reducing adhesion protein of cells, wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK. In an embodiment, methods comprise inhibiting the gene expression. In an embodiment, this invention provides a method of reducing the secretion of fibronectin. In an embodiment the method can block the migration, metastasis of cancer cells or inhibit the growth of cancers or anti-angiogenesis, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer.

This invention provides a method of altering the characteristic of cancer cell membrane, wherein the method comprises altering the secretion of adhesion proteins, wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK. In an embodiment, the methods, processes, compounds and compositions comprises blocking, suppressing or inhibiting the expression or secretion of adhesion protein, wherein the adhesion proteins. In an embodiment, the methods, processes, compounds and compositions is interacting with adhesion protein, wherein the adhesion proteins. In an embodiment the methods, processes, compounds or compositions can block the migration, metastasis of cancer cells or inhibit the growth of cancers or anti-angiogenesis, wherein the cancers comprise breast, leukocyte, liver, ovarian, bladder, prostate, skin, bone, brain, leukemia, lung, colon, CNS, melanoma, renal and cervix cancer.

The adhesion proteins help cancer cell adhesion, invasion or metastasis, wherein the cancers comprise ovarian cancer. Reducing the adhesion proteins will reduces the metastasis of cancers. The fibronectin is one of the key factors in the biology of epithelial ovarian cancers. The reducing of fibronectin will inhibit the metastasis of cancer cells.

This invention provides a method and composition for inhibiting the secretion of adhesion protein comprising fibronectin in order to cure the diseases, wherein the diseases comprise inhibiting cancer growth, wherein the cancers comprise breast, leukocyte, liver, ovarian, bladder, prostate, skin, bone, brain, leukemia, lung, colon, CNS, melanoma, renal and cervix cancer.

This invention provides a composition for inhibiting the growth, migration, metastasis of cancer and by altering the characteristics of membrane of cancer cell, wherein the characteristics comprise adhesion of proteins; wherein comprising the secretion of proteins or the adhesion of cells; wherein the characteristic comprise adhesion ability; wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK; wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer; wherein the method is administering contacting Xanifolia Y0, Y1, Y2, Y, Y7, Y8, Y9, Y10, ACH-Y or a salt, ester, metabolite thereof. In an embodiment the composition is the compound selected from formulas in this application.

This invention provides a method for altering the adhesion characteristic of membrane of cancer cell, wherein the method comprises of reducing the adhesion ability, wherein the method comprises reducing the secretion of fibronectin. wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer, wherein the method is administering contacting an effective amount of Xanifolia Y0, Y1, Y2, Y, Y7, Y8, Y9, Y10, ACH-Y or a salt, ester, metabolite thereof. In an embodiment, the method is administering contacting an effective amount of the compound selected from formulas in this application. In an embodiment, the method is inhibiting the growth, migration, metastasis of cancer. In an embodiment the compound may be selected from formula (1A), (1B), (1C) and (1D). In an embodiment, the compound comprises a triterpene backbone, two angeloyl groups and sugar moiety. In an embodiment the compound(s) are selected from Xanifolia (x), Escin or Aescin. In an embodiment the compound(s) are selected from Compound A to X and A1 to X1. In an embodiment the compound(s) are selected from Compound Z1 to Z7, in the application.

This invention provides a composition for inhibiting the growth, migration, metastasis of cancer by altering the adhesion characteristic of membrane of cancer cell, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer. This invention provides a method and composition for reducing of adhesion protein to cure the diseases, wherein the diseases comprise inhibiting cancer growth, reducing leg swelling, symptoms of chronic venous insufficiency, peripheral edema, antilipemic, chronic venous disease, varicose vein disease, varicose syndrome, venous stasis, expectorant, peripheral vascular disorders, cerebro-organic convulsion, cerebral circulation disorder, cerebral edema, psychoses, dysmenorrheal, hemorrhoids, episiotomies, peripheral edema formation or postoperative swelling; for reducing symptoms of leg pain; for treating pruritis, lower leg volume, for reducing symptoms of pain; thrombosis, thromophlebitis; for preventing gastric ulcers antispasmotic, comprising administering to a subject, in need thereof, an effective amount of the composition of this invention.

In an embodiment, the method comprises interacting with adhesion protein, wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK. In an embodiment, this invention provides a method of reducing the secretion of fibronectin.

In an embodiment, the method comprises reducing the adhesion ability of adhesion protein; wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK.

In an embodiment, the method comprises modulating the secretion, expression, or synthesis of adhesion protein, wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK. In an embodiment, the method comprises blocking the secretion, expression, or synthesis of adhesion protein, wherein the adhesion protein comprising fibronectin. In an embodiment the method is administering contacting an effective amount of the compound selected from formulas in this application.

In an embodiment the method is administering contacting an effective amount of the compound in this application comprising Xanifolia Y0, Y1, Y2, Y, Y7, Y8, Y9, Y10, ACH-Y, Xanifolia (x), Escin or Aescin or a salt, ester, metabolite thereof. In an embodiment the compound(s) are selected from Compound A to X and A1 to X1. In an embodiment the compound(s) are selected from Compound Z1 to Z7, in the application. In an embodiment the compound may be selected from formula (1A), (1B), (1C) and (1D).

This invention provides a method and composition for altering the characteristic of adhesion protein to cure diseases, wherein the characteristic comprising adhesion ability, wherein the method comprises reducing the secretion of fibronectin, wherein the diseases comprise inhibiting cancer growth, reducing leg swelling, symptoms of chronic venous insufficiency, peripheral edema, antilipemic, chronic venous disease, varicose vein disease, varicose syndrome, venous stasis, expectorant, peripheral vascular disorders, cerebro-organic convulsion, cerebral circulation disorder, cerebral edema, psychoses, dysmenorrheal, hemorrhoids, episiotomies, peripheral edema formation or postoperative swelling; for reducing symptoms of leg pain; for treating pruritis, lower leg volume, for reducing symptoms of pain; thrombosis, thromophlebitis; for preventing gastric ulcers antispasmotic, comprising administering to a subject, in need thereof, an effective amount of the composition of this invention; wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK. In an embodiment the method is administering contacting an effective amount in a subject with the compound selected from formulas in this application.

This invention provides a method and composition for modulating the secretion, expression, or synthesis of adhesion protein or angiopoietin in cells comprising contacting said cells with an effective amount of an isolated, purified or synthesized compound, or its salt, or ester thereof. An isolated, purified or synthesized compound or its salt, ester, metabolite or derivative thereof, having the formula of

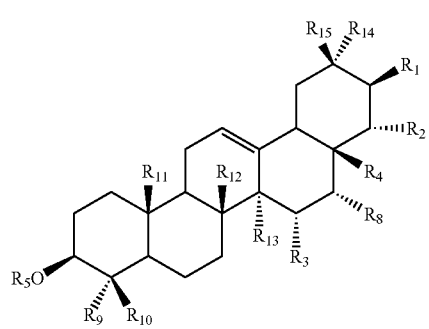

also named (1A), wherein R1 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-aryl, O-acyl, O-heterocylic, O-heteroraryl, and derivatives thereof;

R2 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-aryl, O-acyl, O-heterocylic, O-heteroraryl, and derivatives thereof;

R4 represents $CH_2R6$ or COR6, wherein R6 is selected from a group consisting of hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-aryl, O-acyl, O-heterocylic, O-heteroraryl, and derivatives thereof; or wherein at least two of R1, R2 and R4 have an angeloyl, tigloyl, senecioyl, dibenzoyl, benzoyl, alkanoyl, alkenoyl, benzoyl alkyl substituted alkanoyl, aryl, acyl, heterocylic, heteroraryl, and derivatives thereof, or any of R1, R2 and R4 has two angeloyl, tigloyl, senecioyl, dibenzoyl, benzoyl, alkanoyl, alkenoyl, benzoyl alkyl substituted alkanoyl, aryl, acyl, heterocylic, heteroraryl, and derivatives thereof; or wherein at least two of R1, R2 and R4 are a group has an acyl with C2-10, R3 is H or OH;

R8 is H or OH, particularly OH;

R5 is a hydrogen or sugar moiety(ies) or acid thereof, wherein the sugar moiety(ies) is/are selected from a group consisting of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combination thereof; wherein R9, R10, R11, R12, R13, R14, R15 are independently attached a group selecting from $CH_3$, $CH_2OH$, CHO, COOH, COO-alkyl, COO-aryl, COO-heterocyclic, COO-heteroaryl, $CH_2O$aryl, $CH_2O$-heterocyclic, $CH_2O$-heteroaryl, alkyls group, hydroxyl, acetyl group, particularly $CH_3$;

wherein at least two of R1, R2 and R6 are comprising a group selected from O-angeloyl, O-tigloyl, O-senecioyl, O-dibenzoyl, O-benzoyl, O-alkanoyl, O-alkenoyl, O-benzoyl alkyl substituted O-alkanoyl, O-aryl, O-acyl, O-heterocylic, O-heteroraryl, and derivatives thereof; or at least one of R1, R2, and R4 is a sugar moiety substituted with at least two groups selected from a group consisting of angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, and a derivative thereof; or wherein R4 is $CH_2R6$; wherein R1 and R2 independently consists an O-angeloyl group, or at least two of R1, R2 and R6 are O-angeloyl or at least one of R1, R2 or R6 is a sugar moiety with two O-angeloyls; or wherein at least two of R1, R2 and R4 are a group having an angeloyl, tigloyl, senecioyl, dibenzoyl, benzoyl, alkanoyl, alkenoyl, benzoyl alkyl substituted alkanoyl, aryl, acyl, heterocylic, heteroraryl, and derivatives thereof, or any of R1, R2 and R4 has two angeloyl, tigloyl, senecioyl, dibenzoyl, benzoyl, alkanoyl, alkenoyl, benzoyl alkyl substituted alkanoyl, aryl, acyl, heterocylic, heteroraryl, and derivatives thereof; or wherein the at least two of R1, R2 and R4 are a group having an acyl with C2-10; wherein the acyl groups are selected from a group comprise of angeloyl, methylpropanoyl, methylbutanoyl and acetyl, wherein the acyl groups may be attached to one or more sugar moieties;

wherein R5 is/are the sugar moiety(ies) selected from the following sugars and alduronis acids: glucose, galactose, rhamnose, arabinose, xylose, fucose, allose, altrose, gulose, idose, lyxose, mannose, psicose, ribose, sorbose, tagatose, talose, fructose, glucuronic acid, galacturonic acid; or their derivatives thereof, or the combination thereof; wherein the sugar preferably comprises glucuronic acid, arabinose and galactose; wherein the adhesion proteins comprise fibronectin, integrins family, Myosin, vitronectin, collagen, laminin, cadherin, heparin, tenascin, CD 54, CAM; wherein the modulating comprises reducing, inhibiting and stimulating; wherein modulating the secretion, expression, or synthesis of adhesion protein comprises reducing the fibronectin for inhibiting the metastasis of cancer cells, wherein the cancer is selected from breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, and renal cancer; wherein the angiopoietin comprising angiopoietin 1, angiopoietin 2, angiopoietin 3, angiopoietin 4, angiopoietin 5, angiopoietin 6 and angiopoietin 7; wherein the angiopoietin comprising angiopoietin-like 1, angiopoietin-like 2, angiopoietin-like 3, angiopoietin-like 4, angiopoietin-like 5, angiopoietin-like 6 and angiopoietin-like 7; wherein the modulating secretion, expression, or synthesis of angiopoietin comprises positive and negative regulating; wherein modulating the secretion, expression, or synthesis of angiopoietin comprises stimulating the secretion, expression, or synthesis of angiopoietin 2 in order to inhibit angiogenesis; wherein modulating angiopoietin comprises inhibiting the secretion, expression, or synthesis of angiopoietin 1 in order to inhibit angiogenesis; wherein modulating the secretion, expression, or synthesis of angiopoietin comprises inhibiting the secretion, expression, or synthesis of angiopoietin-like 1; wherein modulating the secretion, expression, or synthesis of angiopoietin comprises inhibiting the secretion, expression, or synthesis of angiopoietin-like 4.

In an embodiment, wherein R5 is/are sugar moiety(ies) selected from a group consisting of glucose, galactose, arabinose, alduronic acid, glucuronic acid, galacturonic acid, and a derivative or combination thereof;

In an embodiment the method is administering contacting the compounds, wherein the compound is selected from the following:

a) An isolated, purified or synthesized compound is having structure Xanifolia (Y),

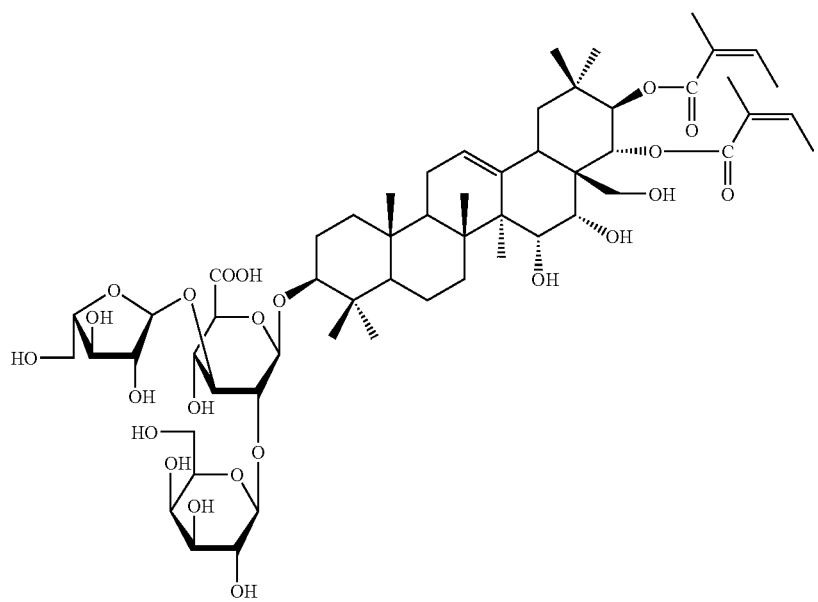

or chemical name: 3-O-[β-D-galactopyranosyl (1→2)]-α-L-arabinofuranosy (1→3)-β-D-glucuronopyranosyl-21,22-O-diangeloyl-3β, 15α, 16α, 21β, 22α, 28-hexahydroxyolean-12-ene;

b) An isolated, purified or synthesized compound is having structure Xanifolia (Y1), or chemical name: 3-O-[β-D-glucopyranosyl-(1→2)]-α-L-arabinofuranosy (1→3)-β-D-glucuronopyranosyl-21,22-O-diangeloyl-3β, 15α, 16α, 21β, 22α, 28-heptahydroxyolean-12-ene;

d) An isolated, purified or synthesized compound is having structure Xanifolia (Y8),

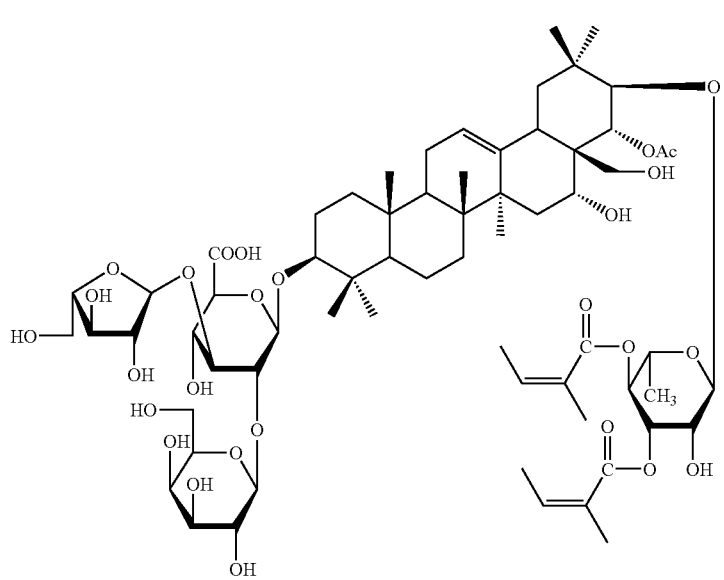

or chemical name: 3-O-[β-D-galactopyranosyl (1-2)]-α-L-arabinofuranosyl (1→3)-β-D-glucuronopyranosyl-21-O-(3,4-diangeloyl)-α-L-rhamnophyranosyl-22-O-acetyl-3β, 16α, 21β, 22α, 28-pentahydroxyolean-12-ene;

c) An isolated, purified or synthesized compound is having structure Xanifolia (Y2),

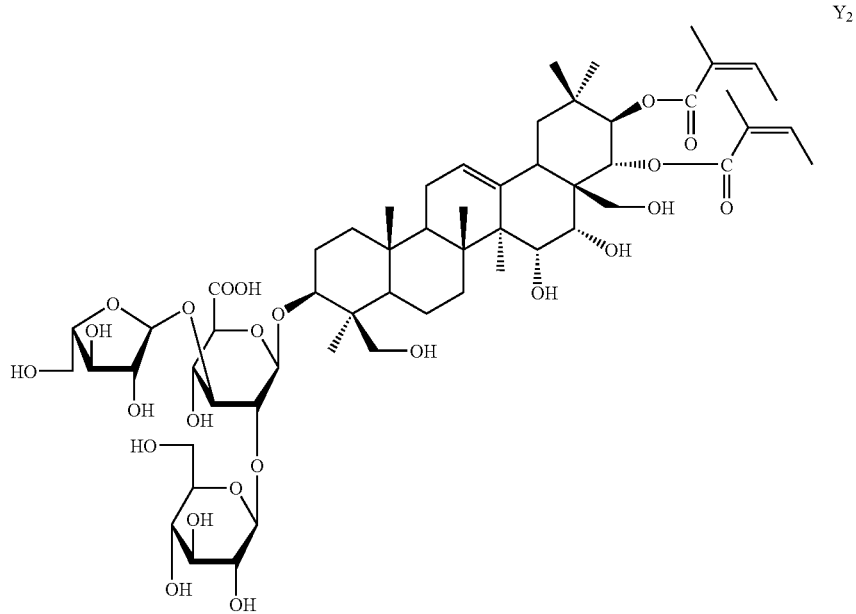

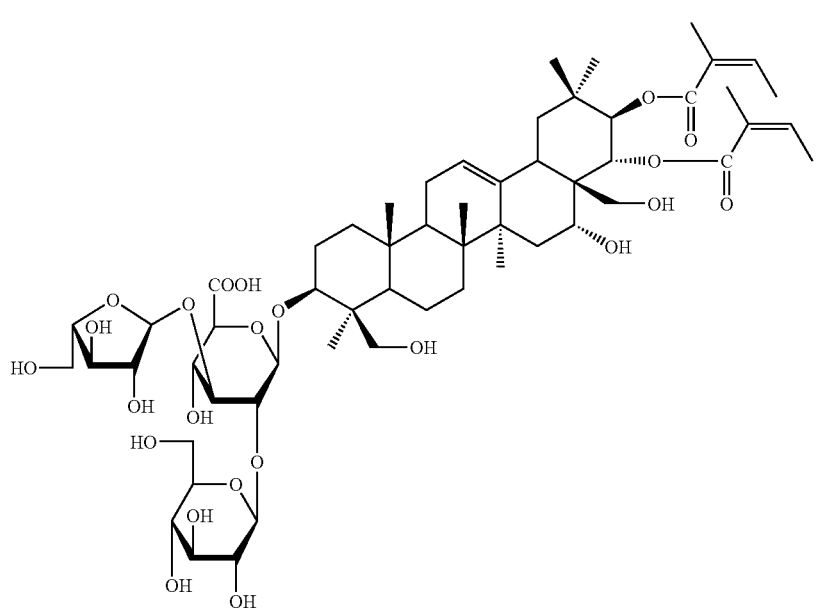

or chemical name: 3-O-[β-glucopyranosyl (1→2)]-α-arabinofuranosyl (1→3)-β-glucuronopyranosyl-21,22-O-diangeloyl-3β, 16α, 21β, 22α, 24β, 28-hexahydroxyolean-12-ene;

e) An isolated, purified or synthesized compound is having structure Xanifolia (Y9),

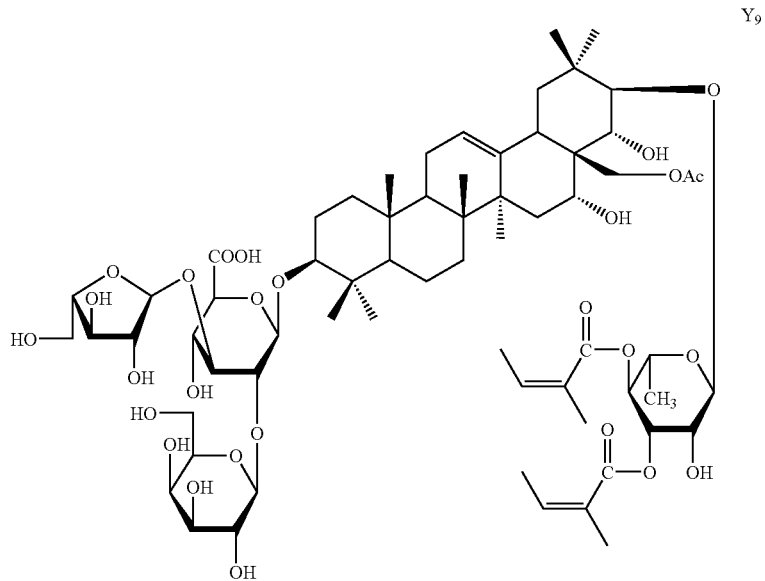

or chemical name: 3-O-[β-galactopyranosyl (1→2)]-α-arabinofuranosyl (1→3)-β-glucuronopyranosyl-21-O-(3,4-diangeloyl)-α-rhamnopyranosyl-28-O-acetyl-3β, 16α, 21β, 22α, 28-pentahydroxyolean-12-ene; and f) An isolated purified or synthesized compound is having structure Xanifolia (Y10),

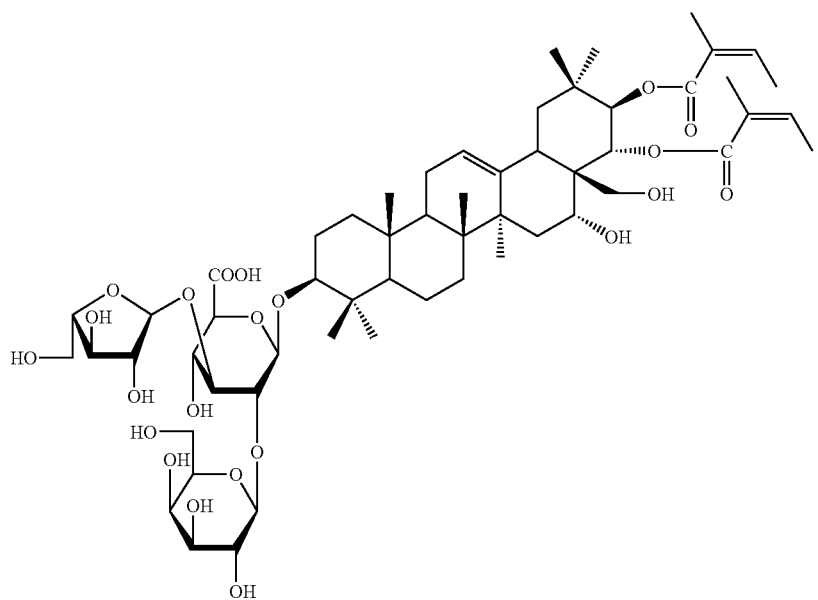

or chemical name: 3-O-[β-galactopyranosyl (1→2)]-α-arabinofuranosyl (1→3)-β-glucuronopyranosyl-21, 22-O-diangeloyl-3β, 16α, 21β, 22α, 28-pentahydroxy-olean-12-ene.

g) An isolated, purified or synthesized compound is having structure Xanifolia (Y0),

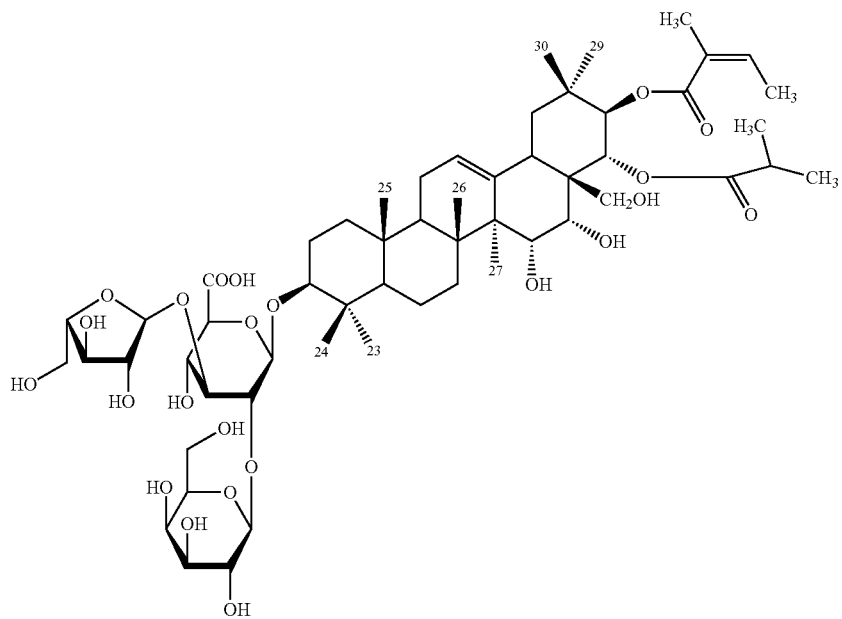

or chemical name: 3-O-[β-D-galactopyranosyl(1→2)]-α-L-arabinofuranosyl(1→3)-β-D-glucuronopyranosyl-21-O-angeloyl, 22-O-(2-methylpropanoyl)-3β, 15α, 16α, 21β, 22α, 28-hexahydroxyolean-12-ene, h) An isolated, purified or synthesized compound is having structure Xanifolia (X),

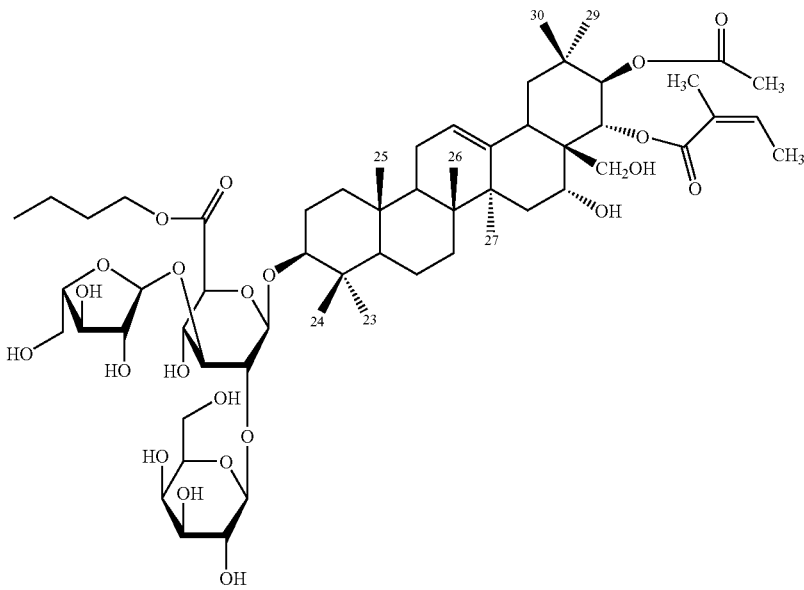

or chemical name: 3-O-({[β-D-galactopyranosyl (1→2)]-[α-arabinofuranosyl(1→3)]-β-D-glucuronopyranoside butyl ester}-21-O-acetyl-22-O-angeloyl-3β,16α,21β, 22α,28-pentahydroxyolean-12-ene.

i) An isolated, purified or synthesized compound is having structure (Y7),

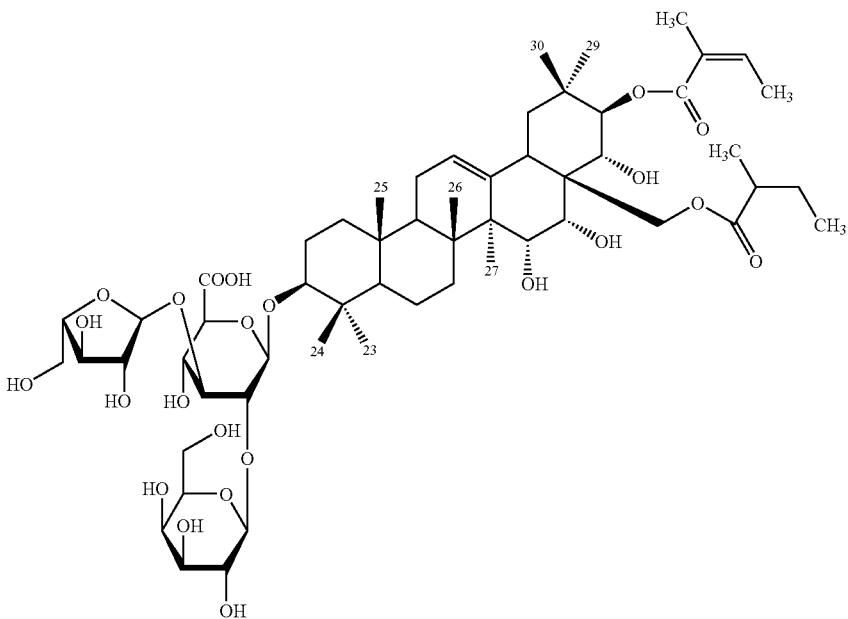

or chemical name: 3-O-[β-D-galactopyranosyl-(1→2)]-α-L-arabinofuranosyl-(1→3)-β-D-glucuronopyranosyl-21-O-angeloyl-28-O-2-methylbutanoyl-3β, 15α, 16α, 21β, 22α, 28-hexahydroxyolean-12-ene j) An isolated, purified or synthesized compound is having structure (ACH-Y):

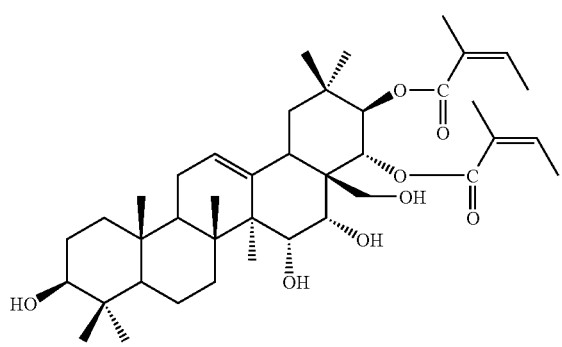

In an embodiment the method is administering contacting the compound, wherein the compound is selected from the following:

k) An isolated, purified or synthesized compound is having a structure:

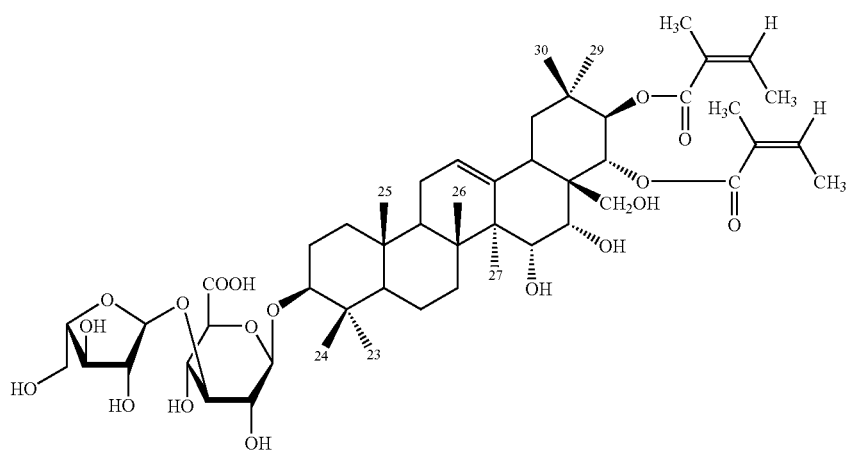

l) An isolated, purified or synthesized compound is having a structure:

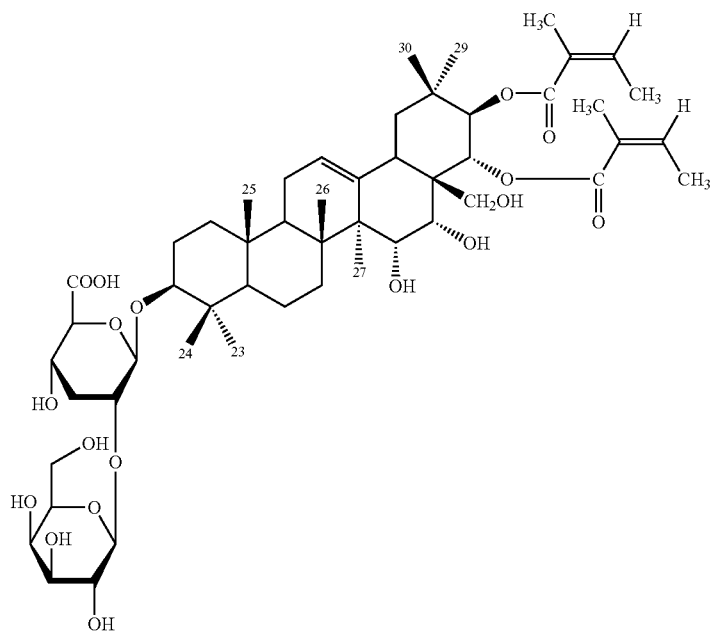

In an embodiment the method is administering contacting the compound, wherein the compound is isolated, purified or synthesized having a structure selected from following formulas:

(1C)

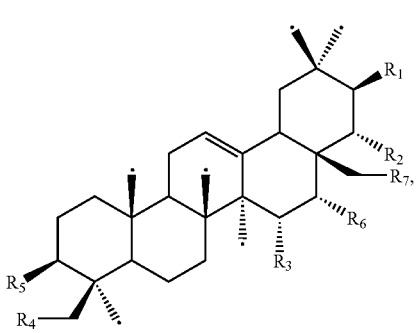

wherein R1, R2 are individually selected of an O-acetyl or O-angeloyl; wherein the R3, R4, R5, R6, R7 is hydrogen or hydroxyl In an embodiment the method is administering contacting the compound in this application comprising Xanifolia Y0, Y1, Y2, Y, Y7, Y8, Y9, Y10, Xanifolia (x), Escin or Aescin or a salt, ester, metabolite thereof. In an embodiment the compound may be selected from formulas (1A), (1B), (1C) and (1D). In an embodiment, the compound comprises a triterpene backbone, two angeloyl groups and sugar moiety. In an embodiment the compound(s) are selected from Xanifolia (Y0, Y1, Y2, Y, Y7, Y8, Y9, and Y10). In an embodiment the compound(s) are selected from Xanifolia (x), Escin or Aescin. In an embodiment the compound(s) are selected from Compound A to X and A1 to X1 in the application. In an embodiment the compound(s) are selected from Compound Z1 to Z7 in the application. In an embodiment the method is administering contacting the compound comprise of a triterpene wherein the carbon position 21, 21 has a unsaturated group and sugar moieties at carbon 3.

In an embodiment, compounds of this application reducing the adhesion ability inhibit bacteria in colonization and regulate tropism of cells.

In an embodiment, reducing the adhesion ability of cell or viruses in order to inhibit viruses binding to host cells, wherein the virus comprise HIV The composition comprises the bioactive compounds from natural plants or synthesis. The majority of the plants are from the Sapindaceae family, which has 140-150 genera with 1400-2000 species. The program is based on our purification methods and biological assays including the MTT assay See International Application No. PCT/US05/31900, filed Sep. 7, 2005, U.S. Ser. No. 11/289,142, filed Nov. 28, 2005, and U.S. Ser. No. 11/131,551, filed May 17, 2005, the contents of which are incorporated herein by reference This invention provides the method uses of compositions comprising a triterpenoidal saponin. In an embodiment, the saponin has triterpenoid, triterpenoidal or other sapogenin, one or more sugar moieties and two angeloyl groups, or at least two side groups selected from the following groups: angeloyl groups, tigloyl groups or senecioyl groups, wherein the side groups are attached to the sapogenin backbone at carbon 21 and 22. In an embodiment, at least two of angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroaryl attached to the side groups; wherein the sugar moiety in the saponin comprises at least one or more of the following sugars and alduronis acids: glucose, galactose, rhamnose, arabinose, xylose, fucose, allose, altrose, gulose, idose, lyxose, mannose, psicose, ribose, sorbose, tagatose, talose, fructose, glucuronic acid, galacturonic acid; or their derivatives thereof, or the combination thereof; wherein the sugar preferably comprises glucuronic acid, arabinose and galactose.

This invention further provides a composition comprising the structures substituted with at least two side groups selected from angeloyl, tigloyl or senecioyl groups, wherein the side groups are attached to a triterpenoidal, triterpenoid, triterpenoidal or other sapongenin backbone. These structures are obtainable from the natural or synthesis. This invention provides a method of preparing the bioactive compounds, comprising the steps of:

(a) Extracting roots, kernels, leaves, bark, stem, husks, seeds, seed shells or fruits of the plant, or combinations thereof with organic solvents such as ethanol or methanol to obtain an organic extract; (b) Collecting the organic extracts; (c) Refluxing the organic extract to obtain a second extract; (d) Removing the organic solvent from the second extract to obtain a third extract; (e) Drying and sterilizing the third extract to obtain a crude extract powder; (f) Fractionating the crude extract powder into fractions or components. Fractionation may be achieved by HPLC and FPLC chromatography with silica gel, C18 or other equivalent solid phase materials; (g) Monitoring the fractionating, if using HPLC or FPLC, the absorption wavelength at 207 nm to 500 nm may be used; (h) Identifying the bioactive components of the crude extract; (i) Purifying one or more bioactive components of the crude extract with FPLC to obtain one or more fractions of the bioactive component; and (j) isolating the bioactive components with chromatographic techniques that employ preparative columns and HPLC.

In an embodiment, this invention provides the method of MTT Assay TEST PLATFORM to test the bioactivities of the saponins or other compounds.

Cells. Human cancer cell lines were obtained from American Type Culture Collection: HTB-9 (bladder), HeLa-S3 (cervix), DU145 (prostate), H460 (lung), MCF-7 (breast), K562 (leukocytes), HCT116 (colon), HepG2 (liver), U2OS (bone), T98G (brain), SK-MEL-5 (Skin) and OVCAR-3 (ovary). The cells were grown in following culture media: HeLa-S3, DU145, MCF-7, Hep-G2 and T98G are in MEN (Earle's salts); HTB-9, H460, K562 and OVCAR-3 in RPMI-1640; HCT-116 and U2OS in McCoy-5A. They are supplemented with 10% fetal calf serum, glutamine and antibiotics, and incubated in an incubator with 5% $CO_2$ humidified at 37° C.

MTT Assay. The procedure for MTT assay followed the method described by Carmichael et al. (1987) with modifications. The cells were seeded into a 96-well plate at concentration of 10,000/well for HTB-9, HeLa, H460, HCT116, T98G and OVCAR-3), 15,000/well for DU145, MCF-7, HepG2 and U2OS), and 40,000/well for K562 for 24 hours before drug-treatment. The cells were then exposed to the drugs for 48 hours (72 hours for HepG2 and U2OS, and 96 hours for MCF-7). After the drug-treatment, MTT (0.5 mg/mL) was added to cultures and incubated for an hour. The formazan (product of the reduction of tetrazolium by viable cells) formed and was dissolved with DMSO and the O.D. at 490 nm, and was measured by an ELISA reader. The MTT level of the cells before drug-treatment was also measured (T0). The % cell-growth (% G) is calculated as: % G=(TD−T0/TC−T0)×100(1), where TC or TD represents O.D. readings of control or drug-treated cells.

When T0>TD, then the cytotoxicity (LC) expressed as % of the control is calculated as:

$$\% LC=(TD-T0/T0)\times100 (2).$$

Micro Array: Analysis of Gene Expression of ES2 Cells after Y-Treatment by Microarray In this invention, the microarray experiments were done in studying the gene expression. Total number of 54676 genes has been studied.

Cell culture and drug-treatment. ES2 cells were seeded in a T-25 flask with 4.5 million cells per flask for 24 hours. Cell culture was replaced with fresh medium with xanifolia-Y (Y) or DMSO no-drug-control (D) for 24 hours. Cells were then harvested for RNA isolation. Three experiments were done.

RNA extraction, labeling, hybridization, and data analysis. RNA was extracted from tumor cells using the Qiagen RNeasy Kit. RNA quality and quantity was checked by the Agilent BioAnalyzer and the NanoDrop® ND-1000 spectrophotometer respectively before further manipulation. The first and second cDNA strands were synthesized from 20 ng of total RNA using the Affymetrix T7 oligo(dT) primer protocol and kit for the two-cycle amplification. To produce amplified biotin-labeled-cRNA, the cDNA was reverse transcribed by in vitro transcription using the MegaScript kit from Ambion. 15.0 μg of the labeled cRNA was fragmented and re-checked for concentration using the NanoDrop® ND-1000 spectrophotometer. A hybridization cocktail containing Affymetrix spike-in controls and fragmented labeled cRNA was loaded onto the Human U133 Plus 2.0 GeneChip® oligonucleotide array. The Affymetrix array (Affymetrix, Inc. Santa Clara, Calif.) is comprised of over 1,300,000 unique oligonucleotide features that represent greater than 38,500 well-substantiated human genes. The array was hybridized for 16 hours at 45° C. with rotation at 60 rpm then washed and stained with a strepavidin, R-phycoerythrin conjugate stain on the Affymetrix Fluidicis Station 450. Signal amplification was done using biotinylated antistreptavidin. The arrays were scanned using the GeneChip® 3000 confocal laser scanner with autoloader. The images were analyzed and quality control metrics recorded using Affymetrix GCOS software version 1.4. Lastly, the expression value for each gene was calculated using dChip PM-only model based or Plier algorithm.

Data Analysis Methods

Pairwise comparisons were made as follows: Treated vs. Control (Y vs. D), Modified Drug vs Control (YM/ACY-H vs. D) and Treated vs. Modified Drug (Y vs. YM/ACH-Y) Cel files analyzed using the Bioconductor package of R Statistical programming. Limma analysis generated a reasonable number of changing genes between the samples.

The raw data were normalized by the GCRMA method (robust multi-array analysis). It is implemented in Bioconductor (http://www.bioconductor.org/). The raw signal intensity data were normalized, background corrected and summarized based on certain statistical models, and an expression value, in log2-scale, is obtained per chip per probe set. Then the null hypothesis was tested that there's no significant changes in gene expression between the treatment pairs. This was done by LIMMA and is also implemented in Bioconductor. It uses empirical Bayes method to estimate the variance in gene expression. One comparison was made, namely, High Grade vs. Low Grade. The raw p-values were adjusted by the Benjamnin-Hochberg method for false discovery rate (FDR) control. All data sets contained a significant number of genes with a p-value less than 0.05, which is that the probability that a gene is NOT differential expressed (false positive) is 1:20.

All expression data is filtered by p-value (0.05).

The raw p-values were adjusted by the Benjamnin-Hochberg method for false discovery rate (FDR) control to yield an adjusted p-value.

Western Blot

Western blot is applied in this invention as a method to detect the specific proteins in treated and untreated cells with compounds in this invention, wherein the cells are breast, leukocyte, liver, ovarian, bladder, prostate, skin, bone, brain, leukemia, lung, colon, CNS, melanoma, renal and cervix cancer Cells: targeted cells were grown in RPMI 1640 medium. 1.5 million cells were seeded in a T25 flask and grown for 24 hours before drug-treatment.

Drug-treatment: Cells cultures were replaced with fresh RPMI medium containing either 2.5 ul of DMSO (as control) [D]; or 10, 20, 30, 40, 80 ug/ml of tested compounds.

After 24 hours, aliquot of culture medium was taken out for Fibronectin determination (Western blot method).

Cell viability at 24 hours was determined by MTT assay. Cultures were replaced with RPMI medium (5 ml) with MTT and incubated for an hour. The formation of formazan was dissolved in 10 ml of DMSO and OD at 570 nm was measured (MTT units).

Western Blot: Spent culture medium was mixed with SDS sample buffer, boiled for 3 minutes before loading to SDS gel. Samples were applied to a 6-10% SDS gel and electrophoresis was conducted with 100 volts for 2 hours. Protein was transferred to a nitrocellulose membrane electrophoretically. The nitrocellulose blot was incubated with the first antibody and second antibody (AP conjugated, Promega S3721). The immuno-bands were developed with BCIP/NBT color development system.

Determination of Western band intensity: The band-images of Western blot were captured with a digital camera and the intensity of bands was determined using "Image J" software.

This invention provides a composition comprising an effective amount of triterpenoidal saponins named as Xanifolia Y1, Y2, Y, Y7, Y8, Y9, Y10, Y0 or their derivatives for modulating the adhesion protein, reducing adhesion protein or reducing the secretion of fibronectin, for treating chronic venous insufficiency, peripheral edema, antilipemic, chronic venous disease, varicose vein disease, varicose syndrome, venous stasis, expectorant, peripheral vascular disorders, cerebro-organic convulsion, cerebral circulation disorder, cerebral edema, psychoses, dysmenorrheal, hemorrhoids, episiotomies, peripheral edema formation or postoperative swelling; for reducing symptoms of pain; for reducing symptoms of stomach pain; for reducing symptoms of leg pain; for treating pruritis, lower leg volume, thrombosis, thrombophlebitis; for treating rheumatism; for preventing gastric ulcers antispasmotic; blocking the migration, metastasis of cancer cells or inhibiting tumor growth. In an embodiment the method is administering contacting the compound in this application comprising Xanifolia Y0, Y1, Y2, Y, Y7, Y8, Y9, Y10, Xanifolia (x), Escin or Aescin or a salt, ester, metabolite thereof. In an embodiment the compound may be selected from formulas (1A), (1B), (1C) and (1D). In an embodiment, the compound comprises a triterpene backbone, two angeloyl groups and sugar moiety. In an embodiment the compound(s) are selected from Compound A to X and A1 to X1 in the application. In an embodiment the compound(s) are selected from Compound Z1 to Z7 in the application.

This invention provides a method for reducing adhesion proteins or their receptors on cells, wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK. In an embodiment the method can block the migration, metastasis of cancer cells or inhibit the growth of cancers or anti-angiogenesis, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer and cervix cancer.

This invention provides a method for interacting with adhesion proteins or their receptors, wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK. In an embodiment, this invention provides a method of reducing the secretion of fibronectin. Furthermore the method is blocking the migration, metastasis of cancer cells or treating a mammal cancers comprising administering to said mammal a therapeutically effective amount of a pharmaceutical composition comprising a composition comprises the molecular formula or compound in this invention. The cancers comprise Leukemia, Lung, Colon, CNS, Melanoma, Ovary, Renal, Prostate, Breast, bladder c, cervix, liver, bone, brain and Skin cancer. The compounds comprise Xanifolia Y0, Y1, Y2, Y, Y7, Y8, Y9, Y10, or a salt, ester, metabolite or derivative thereof. The compounds of this invention can be isolated from natural sources or synthesized.

See experiments results in this application and see PCT/US05/31900, filed Sep. 7, 2006; U.S. Ser. No. 10/906,303, filed Feb. 14, 2005; International Application No. PCT/US04/43465, filed Dec. 23, 2004; International Application No. PCT/US04/33359, filed Oct. 8, 2004 and U.S. Ser. No. 11/131,551, filed May 17, 2005, PCT/US2007/077273, filed Aug. 30, 2007, the contents of which are incorporated herein by reference.

A salt of compound comprise sodium salt, potassium salt or calcium salt.

A salt of compounds for inhibiting venous insufficiency, particularly hemorrhoids or inhibiting leg swelling, or peripheral edema, antilipemic, chronic venous disease, varicose vein disease, varicose syndrome, venous stasis, Expectorant, peripheral vascular disorders, cerebro-organic convulsion, cerebral circulation disorder, cerebral edema, psychoses, dysmenorrheal, hemorrhoids, episiotomies, hamonhoids, peripheral edema formation or postoperative swelling; for reducing symptoms of pain; for reducing symptoms of stomach pain; for reducing symptoms of leg pain; for treating pruritis, lower leg volume, thrombosis, thromophlebitis; for preventing gastric ulcers antispasmotic.

This invention provides a method of modulating the adhesion proteins or their receptors, reducing the adhesion ability of the cancer cells, wherein the modulating comprises the positive or negative regulating. In an embodiment, the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK. In an embodiment, the method is reducing the secretion of fibronectin. This invention provides a method of blocking the migration, metastasis of cancer cells or inhibiting cancer cell growth comprising administering an effective amount of a pharmaceutical composition comprising a composition comprises the molecular formula or compound in this invention. The cancers comprise Leukemia cancer, Lung cancer, Colon cancer, CNS cancer, Melanoma cancer, ovarian cancer, renal cancer, Prostate cancer, Breast cancer, bladder cancer, cervix cancer, liver cancer, bone cancer, brain cancer and Skin cancer. The compounds of this invention can be isolated from natural sources or synthesized. In an embodiment the method is administering contacting the compounds, wherein the compound is selected from the following:

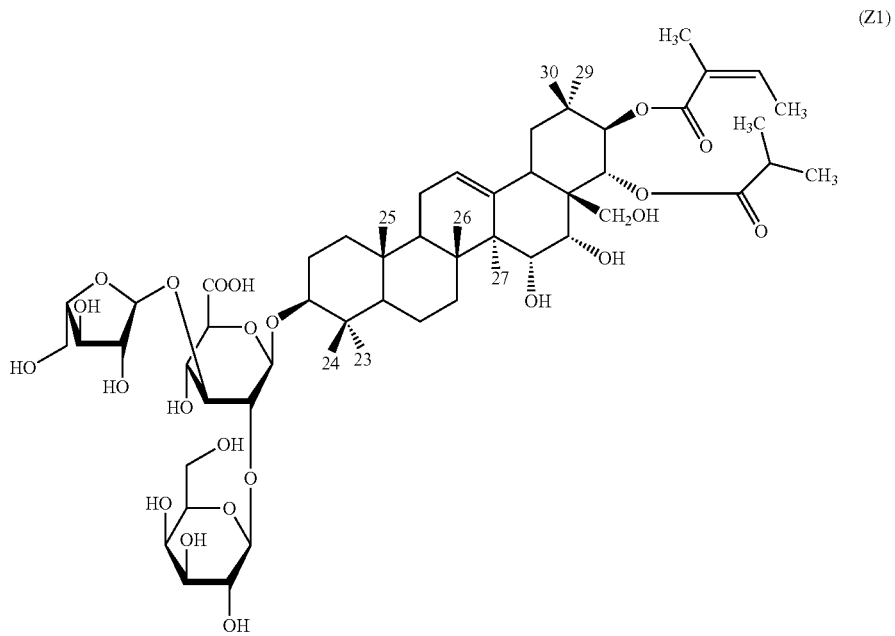

3-O-[β-D-galactopyranosyl(1→2)]-α-L-arabinofuranosyl (1→3)-β-D-glucuronopyranosyl-21-O-angeloyl, 22-O-(2-methylpropanoyl)-3β, 15α, 16α, 21β, 22α, 28-hexahydroxyolean-12-ene,

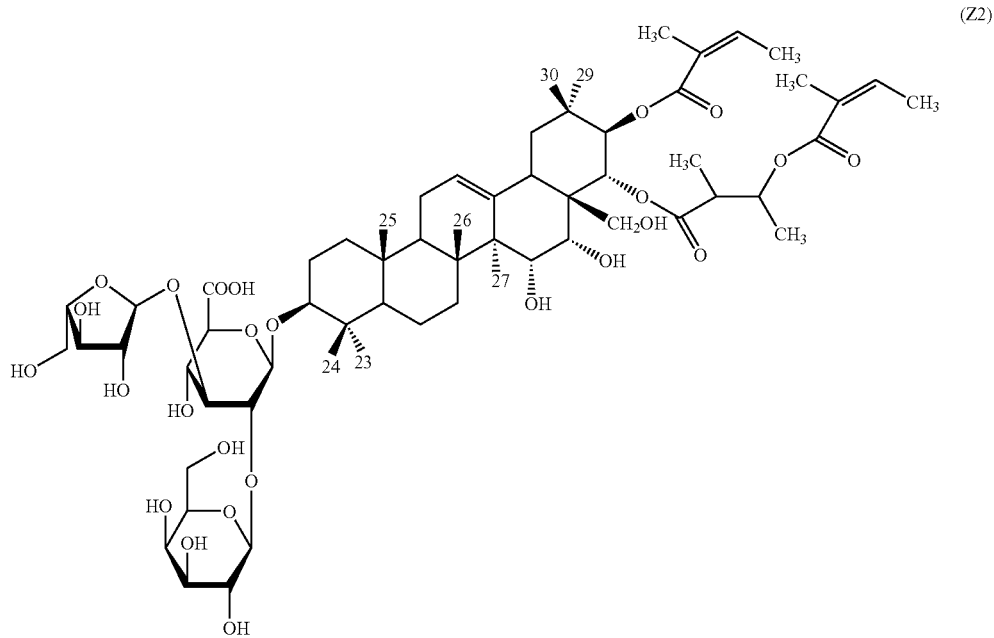

(Z2)

3-O-[β-D-galactopyranosyl-(1→2)]-α-L-arabinofuranosyl-(1→3)-β-D-glucuronopyranosyl-21-O-angeloyl-22-O-(angeloyl-2-methylbutanoyl) -3β, 15α, 16α, 21β, 22α, 28-hexahydroxyolean-12-ene

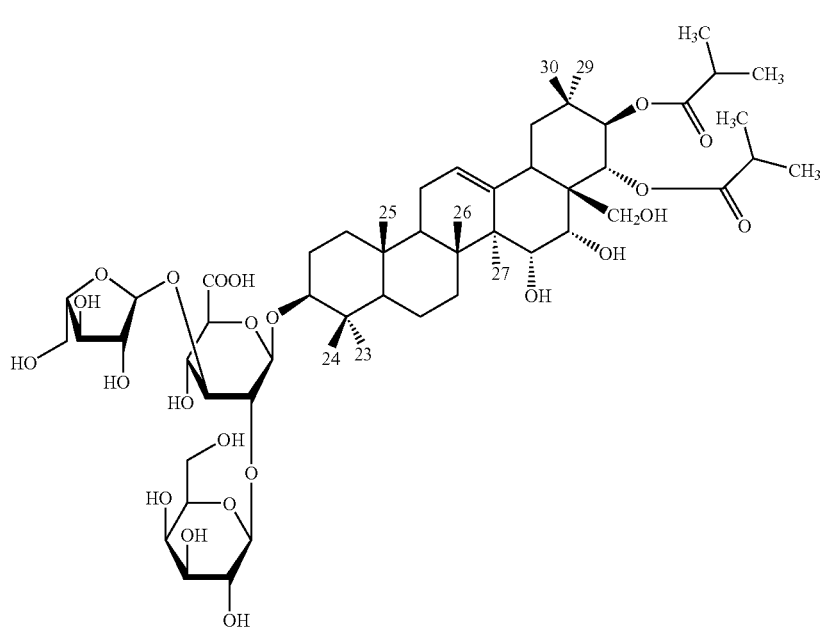

(Z3)

3-O-[β-D-galactopyranosyl(1→2)]-α-L-arabinofuranosyl (1→3)-β-D-glucuronopyranosyl-21-O-(2-methylpropanoyl), 22-O-(2-methylpropanoyl)-3β, 15α, 16α, 21β, 22α, 28-hexahydroxyolean-12-ene,

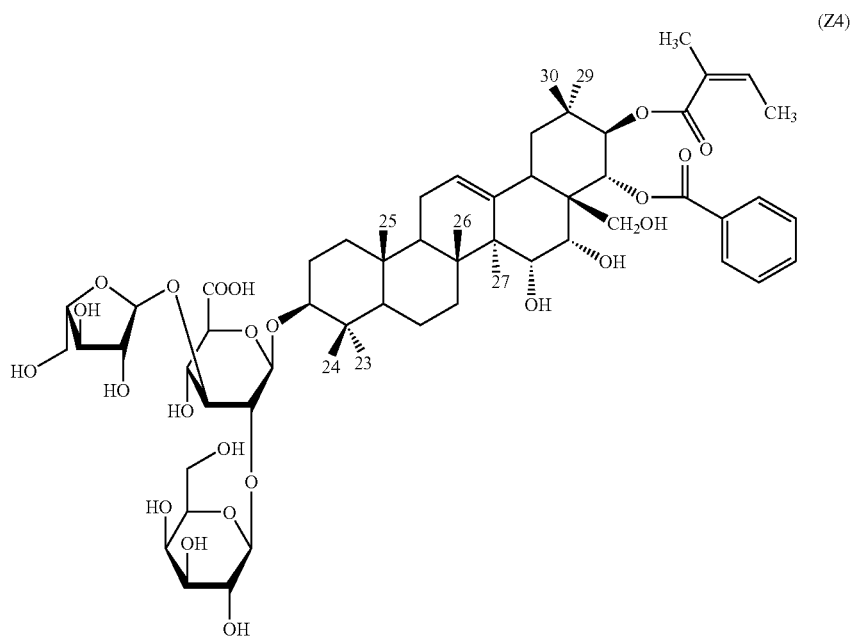
(Z4)
3-O-[β-D-galactopyranosyl(1→2)]-α-L-arabinofuranosyl (1→3)-β-D-glucuronopyranosyl-21-O-angeloyl, 22-O-benzoyl-3β, 15α, 16α, 21β, 22α, 28-hexahydroxyolean-12-ene,
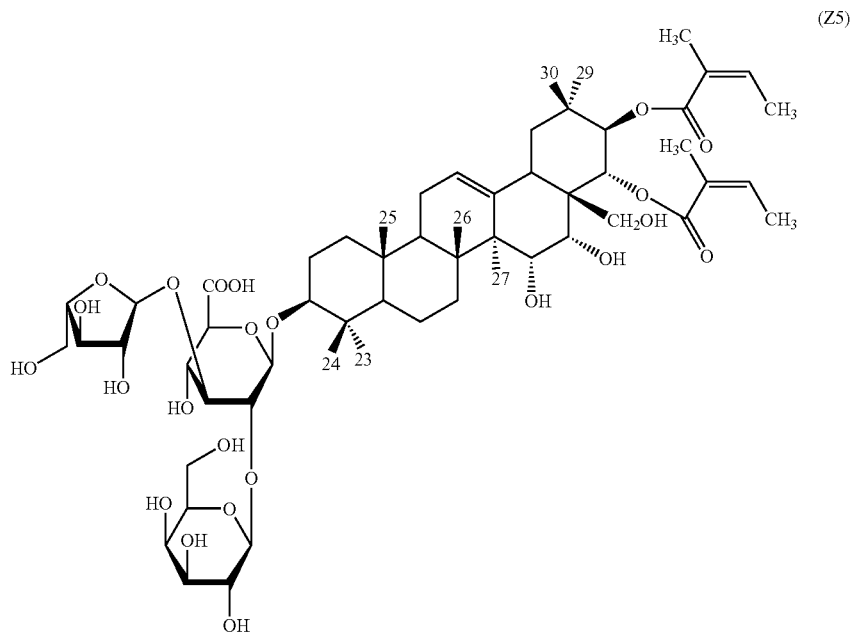
(Z5)
3-O-[β-D-galactopyranosyl(1→2)]-α-L-arabinofuranosyl (1→3)-β-D-glucuronopyranosyl-21-O-angeloyl, 22-O-angeloyl-3β, 15α, 16α, 21β, 22α, 28-hexahydroxyolean-12-ene,

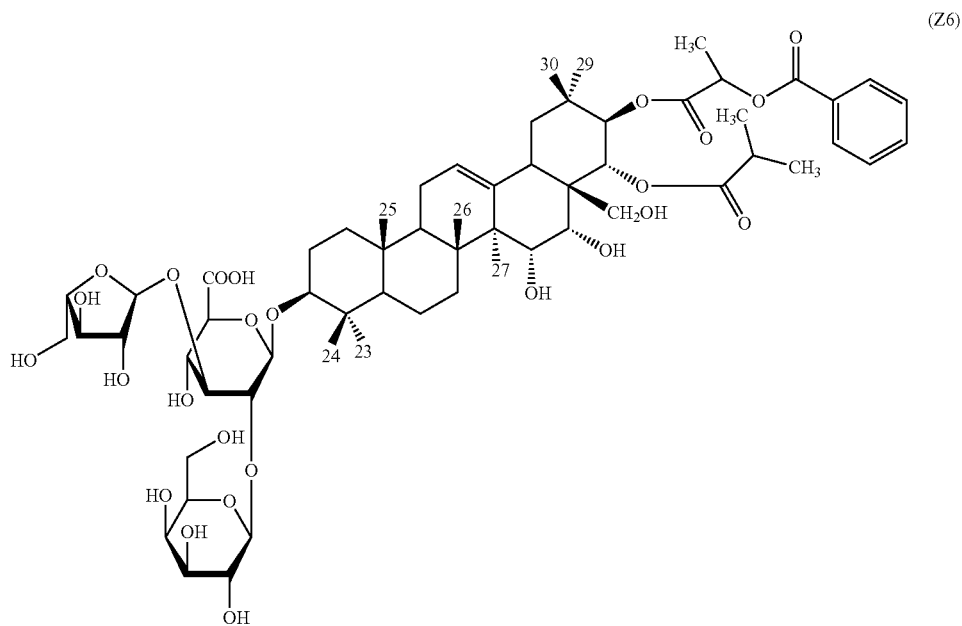
3-O-[β-D-galactopyranosyl(1→2)]-α-L-arabinofuranosyl (1→3)-β-D-glucuronopyranosyl-21-O-(2-methylpropanoyl)-O-benzoyl, 22-O-(2-methylpropanoyl)-3β, 15α, 16α, 21β, 22α, 28-hexahydroxyolean-12-ene,
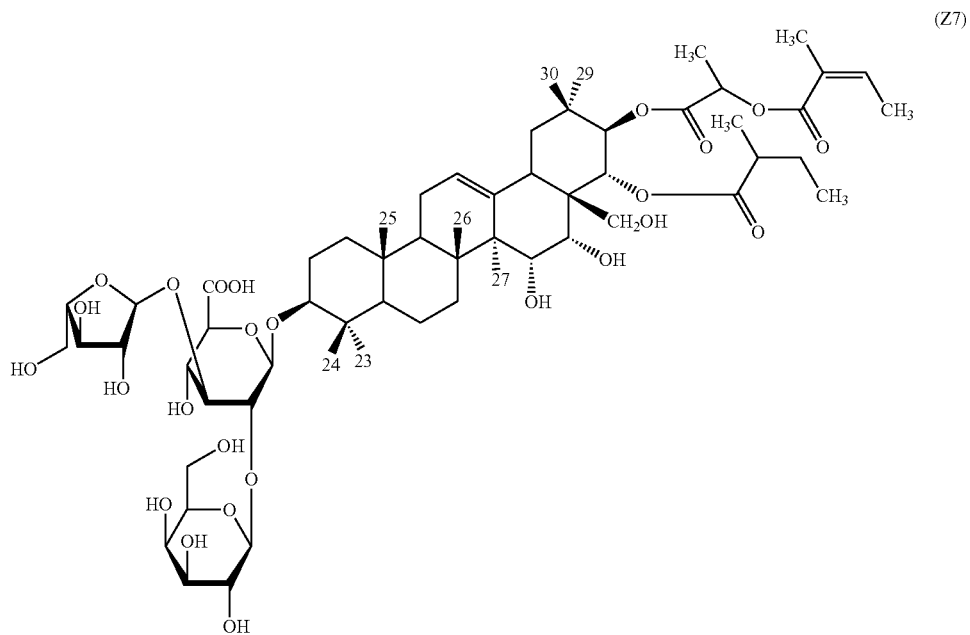
3-O-[β-D-galactopyranosyl(1→2)]-α-L-arabinofuranosyl (1→3)-β-D-glucuronopyranosyl-21-O-(2-methylpropanoyl)-O-angeloyl, 22-O-(2- methylbutanoyl)-3β, 15α, 16α, 21β, 22α, 28-hexahydroxyolean-12-ene,

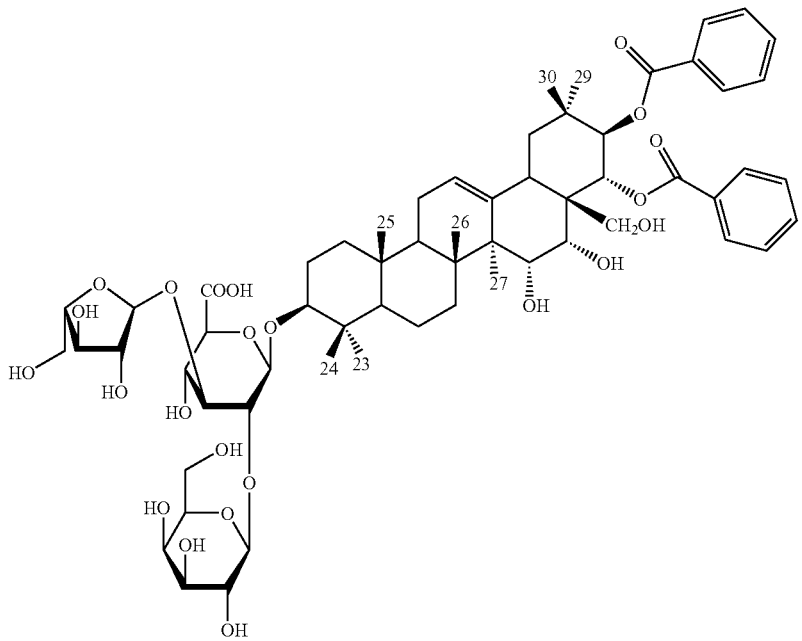

Z8

3-O-[β-D-galactopyranosyl(1→2)]-α-L-arabinofuranosyl (1→3)-β-D-glucuronopyranosyl-21-O-benzoyl, 22-O-benzoyl-3β, 15α, 16α, 21β, 22α, 28-hexahydroxyolean-12-ene This invention provide uses of a compound selected from a compound with formula (1B), for modulating, regulating or interacting the adhesion protein, wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK. In an embodiment, this invention provides a method of reducing the secretion of fibronectin. In an embodiment, this invention provides method for modulating the secretion, expression, or synthesis of adhesion protein or angiopoietin in cells comprising contacting said cells with an effective amount of an isolated, purified or synthesized compound, or its salt, or ester thereof, selected from the formula:

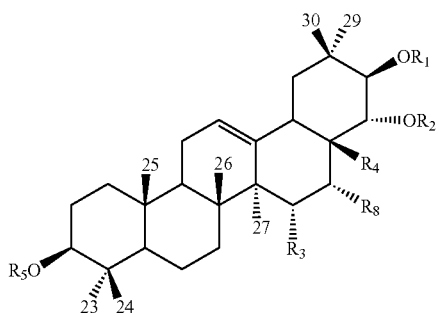

also named as (1B), or a salt, ester, metabolite or derivative thereof, wherein R1 comprises a group selected from hydrogen, angeloyl, acetyl, tigloyl, senecioyl, alkyl, dibenzoyl, benzoyl, alkanoyl, alkenoyl, benzoyl alkyl substituted alkanoyl, acyl, aryl, heterocylic, heteroaryl and derivatives thereof; R2 comprises a group selected from hydrogen, angeloyl, acetyl, tigloyl, senecioyl, alkyl, benzoyl, dibenzoyl, alkanoyl, alkenoyl, benzoyl alkyl substituted alkanoyl, aryl, acyl, heterocyclic, heteroaryl and derivative thereof; R4 comprise $CH_2OR6$ or $COOR6$, wherein R6 is selected from hydrogen, angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroaryl and derivative thereof; R3 is H or OH; wherein at least one of R1, R2, and R6 comprises a group selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroaryl and derivative thereof; R5 comprises a sugar moiety, wherein the sugar moiety comprises at least one sugar of, but is not limited to, D-glucose, D-galactose, L-rhamnose, L-arabinose, D-xylose, alduronic acid: D-glucuronic acid, D-galacturonic acid or a derivative thereof, or the combination thereof. In an embodiment, R1 comprises a sugar moiety wherein substituted with two groups selecting from angeloyl, acetyl, tigloyl, senecioyl, benzoyl, dibenzoyl, alkanoyl, alkenoyl, benzoyl alkyl substituted alkanoyl, aryl, acyl, heterocylic heteroaryl and a derivative thereof; wherein the adhesion proteins comprise fibronectin, integrins family, Myosin, vitronectin, collagen, laminin, cadherin, heparin, tenascin, CD 54, CAM; wherein the modulating comprises reducing, inhibiting and stimulating; wherein modulating the secretion, expression, or synthesis of adhesion protein comprises reducing the fibronectin for inhibiting the metastasis of cancer cells, wherein the cancer is selected from breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, and renal cancer; wherein the angiopoietin comprising angiopoietin 1, angiopoietin 2, angiopoietin 3, angiopoietin 4, angiopoietin 5, angiopoietin 6 and angiopoietin 7; wherein the angiopoietin comprising angiopoietin-like 1, angiopoietin-like 2, angiopoietin-like 3, angiopoietin-like 4, angiopoietin-like 5, angiopoietin-like 6 and angiopoietin-like 7; wherein the modulating secretion, expression, or synthesis of angiopoietin comprises positive and negative regulating; wherein modulating the secretion, expression, or synthesis of angiopoietin comprises stimulating the secretion, expression, or synthesis of angiopoietin 2 in order to inhibit angiogenesis; wherein modulating angiopoietin comprises inhibiting the secretion, expression, or synthesis of angiopoietin 1 in order to inhibit angiogenesis; wherein modulating the secretion, expression, or synthesis of angiopoietin comprises inhibiting the secretion, expression, or synthesis of angiopoietin-like 1; wherein modulating the secretion, expression, or synthesis of angiopoietin comprises inhibiting the secretion, expression, or synthesis of angiopoietin-like 4.

In an embodiment, R1 comprises a sugar moiety wherein substituted with at least one group selecting from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl and a derivative thereof.

In an embodiment, R2 comprises a sugar moiety wherein at least one group is selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl and a derivative thereof.

In an embodiment, R2 comprises a sugar moiety or a side chain wherein at least two groups are selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl and a derivative thereof.

In an embodiment, R4 comprises $CH_2OR6$ or COOR6 wherein R6 is a sugar moiety which comprises at least one group selected from angeloyl, acetyl, tigloyl, senecioyl, benzoyl, dibenzoyl, alkanoyl, alkenoyl, benzoyl alkyl substituted alkanoyl, aryl, acyl, heterocyclic, heteroraryl and a derivative thereof.

In an embodiment, R4 comprises $CH_2OR6$ or COOR6, wherein R6 is a sugar moiety which comprises at least two groups selected from angeloyl, acetyl, tigloyl, senecioyl, benzoyl, dibenzoyl, alkanoyl, alkenoyl, benzoyl alkyl substituted alkanoyl, aryl, acyl, heterocyclic, heteroraryl and a derivative thereof.

In an embodiment, R4 comprises $CH_2OR6$ or COOR6, wherein R6 is a sugar moiety which comprises at least two groups selected from angeloyl, acetyl, tigloyl and senecioyl.

In an embodiment, R4 comprises $CH_2OR6$ or COOR6 of formula (1B), at least two of R1, R2 and R6 comprise the group selected from angeloyl, acetyl, tigloyl, senecioyl, benzoyl, dibenzoyl, alkanoyl, alkenoyl, benzoyl alkyl substituted alkanoyl, aryl, acyl, heterocyclic, heteroraryl and a derivative thereof.

In an embodiment, R4 comprises $CH_2OR6$ or COOR6 of formula (1B), at least two of R1, R2 and R6 comprise angeloyl, benzoyl, alkenoyl, or a derivative thereof.

In an embodiment, R4 is a side chain comprising $CH_2OCOCH_3$, $CH_2COO$-alkyl, $CH_2OH$, COOH, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or a derivative thereof.

In a further embodiment, R5 comprises a sugar moiety, wherein the sugar moiety comprises one or more sugar of, but is not limited to glucose, galactose, rhamnose, arabinose, xylose, fucose, allose, altrose, gulose, idose, lyxose, mannose, psicose, ribose, sorbose, tagatose, talose, fructose, or alduronic acid: glucuronic acid, galacturonic acid, or derivatives thereof, or the combination thereof.

In an embodiment, R5 comprises a sugar moiety or a group capable of performing the function of the sugar moiety.

In an embodiment, the R5 represents H.

In an embodiment, R4 represents H, OH or $CH_3$.

In an embodiment, position C23, C24, C25, C26, C29 and C30 of the compound independently comprise $CH_3$, $CH_2OH$, CHO, COOH, COOa-lkyl, COO-aryl, COO-heterocyclic, COO-heteroaryl, $CH_2Oaryl$, $CH_2O$— heterocyclic, $CH_2O$— heteroaryl, alkyls group, acetyl group or derivatives thereof, particular $CH_3$.

In an embodiment, R1 and R2 independently comprise an angeloyl group.

In an embodiment, R1 is a sugar moiety or a side chain which comprise two angeloyl groups.

In an embodiment, R1 and R2 independently comprise a benzoyl group.

In an embodiment, R1 is a sugar moiety which is substituted with two benzoyl groups.

In an embodiment, R3 represents H or OH.

In an embodiment, R8 may be OH

Substitution, deletion and/or addition of any group in the above-described compounds by other group(s) will be apparent to one of ordinary skill in the art based on the teachings of this application. In a further embodiment, the substitution, deletion and/or addition of the group(s) in the compound of the invention does not substantially affect the biological function of the compound. A composition comprising an effective amount of the compound selected from the above formula or a salt, ester, metabolite or derivative thereof as a medicament for regulating or interacting with adhesion protein, wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK. In an embodiment, this invention provides a method of reducing the secretion of fibronectin; wherein the medicament is for inhibiting tumor or cancer cell growth and for treating cancer, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer.

This invention provides uses of a compound selected from a compound of formula (1D), for regulating or interacting with adhesion protein, wherein the adhesion proteins comprise of fibronectin, integrins family, Myosin, vitronectin, collagen, laminin, Glycosylation cell surface proteins, polyglycans, cadherin, heparin, tenascin, CD 54, CAM, elastin and FAK. In an embodiment, this invention provides a method of reducing the secretion of fibronectin.

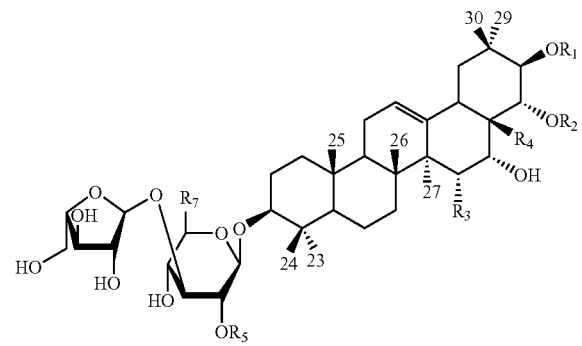

and also named as (1D), or a salt, ester, metabolite or derivative thereof, wherein R1 comprises a group selected from hydrogen, angeloyl, acetyl, tigloyl, senecioyl, alkyl, benzoyl, alkanoyl, alkenoyl, benzoyl alkyl substituted alkanoyl, aryl, acyl, heterocylic, heteroraryl and a derivative thereof; R2 comprises a group selected from hydrogen, angeloyl, acetyl, tigloyl, senecioyl, alkyl, benzoyl, alkanoyl, alkenoyl, benzoyl alkyl substituted alkanoyl, aryl, acyl, heterocyclic, heteroraryl and a derivative thereof; R4 comprises $CH_2OR6$ or COOR6, wherein R6 comprises a group selected from hydrogen, angeloyl, acetyl, tigloyl, senecioyl, alkyl, benzoyl, alkanoyl, alkenoyl, benzoyl alkyl substituted alkanoyl, aryl, acyl, heterocylic, heteroraryl and a derivative thereof; R3 is H or OH; R5 comprises sugar moiety, D-glucose or D-galactose; R7 represents COOH; wherein at least one of R1 and R2 is an acyl.

In an embodiment, R7 is selected from $CH_3$, $CH_2OH$, COOH and COOalkyl.

In an embodiment, R7 is selected from $CH_3$, $CH_2OH$, CHO, COOH, COOalkyl, COOaryl, COO-heterocyclic, COO-heteroaryl, $CH_2Oaryl$, $CH_2O$-heterocyclic, $CH_2O$-heteroaryl, alkyls group, acetyl group and a derivative thereof.

In an embodiment, R1 represents a compound comprising a sugar moiety wherein the sugar moiety is substituted with at least two compounds selected from angeloyl, acetyl, tigloyl, senecioyl, alkyl, benzoyl, alkanoyl, alkenoyl, benzoyl alkyl substituted alkanoyl, aryl, acyl, heterocyclic, heteroraryl and a derivative thereof;

In an embodiment, R1 represents a compound comprising a sugar moiety substituted with at least one selected from angeloyl, acetyl, tigloyl, senecioyl, benzoyl, alkanoyl, alkenoyl, benzoyl alkyl substituted alkanoyl, aryl, acyl, heterocylic, heteroraryl and a derivative thereof;

In an embodiment, R2 represents a compound comprising a sugar moiety, wherein the sugar moiety substituted with at least one selected from angeloyl, acetyl, tigloyl, senecioyl, benzoyl, alkanoyl, alkenoyl, benzoyl alkyl substituted alkanoyl, aryl, acyl, heterocyclic, heteroraryl and a derivative thereof;

In an embodiment, R2 represents a compound comprising a sugar moiety or a compound which substituted with at least two selected from, angeloyl, acetyl, tigloyl, senecioyl, benzoyl, alkanoyl, alkenoyl, benzoyl alkyl substituted alkanoyl, aryl, acyl, heterocyclic, heteroraryl and a derivative thereof;

In an embodiment, R4 comprises a group selected from $CH_2OR6$ and COOR6 wherein R6 is a sugar moiety which substituted with at least one selected from angeloyl, acetyl, tigloyl, senecioyl, benzoyl, alkanoyl, alkenoyl, benzoyl alkyl substituted alkanoyl, aryl, acyl, heterocylic, heteroraryl and a derivative thereof;

In an embodiment, R4 comprises a group selected from $CH_2OR6$ and COOR6 wherein R6 is a sugar moiety which substituted with at least two selected from angeloyl, acetyl, tigloyl, senecioyl, benzoyl, alkanoyl, alkenoyl, benzoyl alkyl substituted alkanoyl, aryl, acyl, heterocylic, heteroraryl and a derivative thereof;

In an embodiment, R4 comprises a group selected from $CH_2OR6$ and COOR6 wherein R6 is a sugar moiety which substituted with at least two selected from angeloyl, acetyl, tigloyl and senecioyl.

In an embodiment, R4 comprises a group selected from $CH_2OR6$ and COOR6 wherein R6 is a sugar moiety which substituted with at least two selected from angeloyl, acetyl, tigloyl, senecioyl, benzoyl, alkanoyl, alkenoyl, dibenzoyl, benzoyl alkyl substituted alkanoyl, aryl, acyl, heterocyclic, heteroraryl and a derivative thereof;

In an embodiment, R4 comprises a group selected from $CH_2OR6$ and COOR6 wherein at least two of R1, R2 and R6 comprise a group selected from angeloyl, acetyl, tigloyl, senecioyl, benzoyl, alkanoyl, alkenoyl, benzoyl alkyl substituted alkanoyl, aryl, acyl, heterocyclic, heteroraryl and derivative thereof;

In an embodiment, R4 comprises a group selected from $CH_2OCOCH_3$, $CH_2COOalkyl$, $CH_2OH$, COOH, angeloyl, acetyl, tigloyl, senecioyl, alkyl, benzoyl, alkanoyl, alkenoyl, benzoyl alkyl substituted alkanoyl, aryl, acyl, heterocyclic, heteroraryl and derivative thereof.

In a further embodiment, R5 comprises a sugar moiety, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or derivative thereof, or the combination thereof. In an embodiment, R5 comprises a compound capable of performing the function of the sugar moiety. In a further embodiment, the R5 comprises a H. In a further embodiment, R4 represents H or OH or $CH_3$.

In an embodiment, position 24 of the compound is $CH_3$ or $CH_2OH$, In a further embodiment, positions 23, 24, 25, 26, 29, 30 of the compound independently comprise $CH_3$, $CH_2OH$, CHO, COOH, COOalkyl, COOaryl, COO-heterocyclic, COO-heteroaryl, $CH_2Oaryl$, $CH_2O$-heterocyclic, $CH_2O$-heteroaryl, alkyls group, acetyl group or a derivative thereof.

In an embodiment, R5 comprises a sugar moiety comprising L-glucose, D-galactose, L-rhamnose, or/and L-arabinose.

In an embodiment, R1 and R2 independently comprise an angeloyl group; In a embodiment, R1 is a sugar moiety or rhamnose which comprise two angeloyl groups.

In an embodiment, R3 represents H or OH; In a further embodiment, the compounds can be isolated from natural sources or synthesized.

A sugar moiety is a segment of a molecule comprising one or more sugar groups. Substitution, deletion and/or addition of any group in the above-described compounds will be apparent to one of ordinary skill in the art based on the teaching of this application. In a further embodiment, the substitution, deletion and/or addition of the group(s) in the compound of the invention does not substantially affect the biological function of the compound.

A method of inhibiting venous insufficiency, particularly hemorrhoids or inhibiting leg swelling, or peripheral edema, antilipemic, chronic venous disease, varicose vein disease, varicose syndrome, venous stasis, Expectorant, peripheral vascular disorders, cerebro-organic convulsion, cerebral circulation disorder, cerebral edema, psychoses, dysmenorrheal, hemorrhoids, episiotomies, hamonhoids, peripheral edema formation or postoperative swelling; for reducing symptoms of pain; for reducing symptoms of stomach pain; for reducing symptoms of leg pain; for treating pruritis, lower leg volume, thrombosis, thromophlebitis; for preventing gastric ulcers antispasmotic comprising administering to a subject, in need thereof, an effective amount of the composition of any one of the above compounds or a compound comprises a triterpene which comprises any two of angeloyl, tigloyl, senecioyl, preferable two angeloyl groups, and a sugar moiety, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or a derivative thereof, or the combination thereof, preferable selected from glucuronic acid, galacturonic acid, glucose, galactose and arabinose. The method is regulating or interacting with adhesion protein, wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK. In an embodiment, the method is reducing the secretion of fibronectin.

This invention provides a method for inhibiting the growth, migration, metastasis of cancer by altering the characteristic of membrane of cancer cell, wherein the characteristic comprise reducing adhesion protein; wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK; wherein comprising inhibiting the secretion of fibronectin, wherein comprising administering to a subject, in need thereof, an appropriate amount of triterpenoidal saponins comprising two or more angeloyl groups, or a compound comprises a triterpene which comprises any two of angeloyl, tigloyl, senecioyl, preferable two angeloyl groups, and a sugar moiety, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or a derivative thereof, or the combination thereof, preferably selected from glucuronic acid, galacturonic acid, glucose, galactose and arabinose. This invention provides a composition comprising an effective amount of the compound of any one of compound selected from the above formula or a salt, ester, metabolite or derivative thereof as a medicament for reducing adhesion protein; wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK, for inhibiting the growth, migration, metastasis of cancer, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer.

This invention also provides a composition comprising the above described compounds or their derivatives for reducing adhesion protein, wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK; wherein comprising inhibiting the secretion of fibronectin, wherein for treating venous insufficiency, particularly hemorrhoids or inhibiting leg swelling, or peripheral edema, antilipemic, chronic venous disease, varicose vein disease, varicose syndrome, venous stasis, Expectorant, peripheral vascular disorders, cerebro-organic convulsion, cerebral circulation disorder, cerebral edema, psychoses, dysmenorrheal, episiotomies, hemorrhoids, peripheral edema formation or postoperative swelling; for reducing symptoms of pain; for reducing symptoms of stomach pain; for reducing symptoms of leg pain; for treating pruritis, lower leg volume, thrombosis, thromophlebitis; for preventing gastric ulcers antispasmotic comprising administering to a subject, in need thereof, an effective amount of the composition.

In an embodiment of the above, the uses of compositions comprising any one of triterpenoid saponins with the following formula:

3-{[[β-D-galactopyranosyl(1→2)]-[α-L-arabinofuranosyl (1→3)]-β-D-glucuronopyranoside butyl ester}-21-acetyl-22-O-angeloyl-3β,16α,21β,22α,28-pentahydroxyolean-12-ene.

3-O-[β-D-galactopyranosyl(1→2)]-α-L-arabinofuranosyl (1→3)-β-D-glucuronopyranosyl-21,22-O-diangeloyl-3β, 15α, 16α, 21β, 22α, 28-hexahydroxyolean-12-ene, 3-O-[β-D-galactopyranosyl(1→2)]-α-L-arabinofuranosyl (1→3)-β-D-glucuronopyranosyl-21-O-(3,4-diangeloyl)-α-L-rhamnophyranosyl-22-O-acetyl-3β, 16α, 21β, 22α, 28-pentahydroxyolean-12-ene, 3-O-[β-D-glucopyranosyl-(1→2)]-α-L-arabinofuranosyl (1→3)-β-D-glucuronopyranosyl-21,22-O-diangeloyl-3β, 15α, 16α, 21β, 22α, 28-heptahydroxyolean-12-ene, 3-O-[β-glucopyranosyl(1→2)]-α-arabinofuranosyl(1→3)-β-glucuronopyranosyl-21, 22-O-diangeloyl-3β, 16α, 21β, 22α, 24β, 28-hexahydroxyolean-12-ene, 3-O-[β-galactopyranosyl(1→2)]-α-arabinofuranosyl(1→3)-β-glucuronopyranosyl-21-O-(3,4-diangeloyl)-α-rhamnopyranosyl-28-O-acetyl-3β, 16α, 21β, 22α, 28-pentahydroxyolean-12-ene, 3-O-[β-galactopyranosyl(1→2)]-α-arabinofuranosyl(1→3)-β-glucuronopyranosyl-21, 22-O-diangeloyl-3β, 16α,21β, 22α, 28-pentahydroxyolean-12-ene, 3-O-[β-D-galactopyranosyl(1→2)]-α-L-arabinofuranosyl (1→3)-β-D-glucuronopyranosyl-21-O-angeloyl, 22-O-(2-methylpropanoyl)-3β, 15α, 16α, 21β, 22α, 28-hexahydroxyolean-12-ene, 3-O-[β-D-galactopyranosyl-(1→2)]-α-L-arabinofuranosyl-(1→3)-β-D-glucuronopyranosyl-21-O-angeloyl-28-O-2-methylbutanoyl-3β, 15α, 16α, 21β, 22α, 28-hexahydroxyolean-12-ene This invention provides a composition comprising the compounds as described above effective in regulating or reducing adhesion protein, wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK; inhibiting venous insufficiency, particularly hemorrhoids or inhibiting of leg swelling, and inhibiting cancer growth. The cancer includes but is not limited to bladder cancer, bone, cancer, skin cancer and ovarian cancer.

This invention also provides a composition for regulating or reducing adhesion protein, wherein the adhesion protein comprising fibronectin, integrins family, CD44, Myosin VI, vitronectin collagen, laminin, Glycosylation cell surface proteins, polyglycans and FAK; inhibiting venous insufficiency, particularly hemorrhoids or inhibition of leg swelling, or inhibiting cancer growth comprising any of compounds selected from the following compounds:

A) 3-O-[β-D-galactopyranosyl (1→2)]-α-L-arabinofuranosyl (1→3)-β-D-glucuronopyranosyl-21, 22-O-diangeloyl-3β, 15α, 16α, 21β, 22α, 28-hexahydroxyolean-12-ene, B) 3-O-[β-D-galactopyranosyl (1→2)]-α-L-arabinofuranosyl (1→3)-β-D-glucuronopyranosyl-21-O-(3, 4-diangeloyl)-α-L-rhamnophyranosyl-22-O-acetyl-3β, 16α, 21β, 22α, 28-pentahydroxyolean-12-ene C) 3-O-[β-D-glucopyranosyl-(1→2)]-α-L-arabinofuranosyl (1→3)-(-D-glucuronopyranosyl-21,22-O-diangeloyl-3β, 15α, 16α, 21β, 22α, 24β, 28-heptahydroxyolean-12-ene D) 3-O-[β-galactopyranosyl (1→2)]-α-arabinofuranosyl (1→3)-β-glucuronopyranosyl-21,22-O-diangeloyl-3β, 16α, 21β, 22α, 28-pentahydroxyolean-12-ene E) 3-O-[β-galactopyranosyl (1→2)]-α-arabinofuranosyl (1→3)-β-glucuronopyranosyl-21-O-(3,4-diangeloyl)-α-rhamnopyranosyl-28-O-acetyl-3β, 16α, 21β, 22α, 28-pentahydroxyolean-12-ene F) 3-O-[β-galactopyranosyl (1→2)]-α-arabinofuranosyl (1→3)-β-glucuronopyranosyl-21,22-O-diangeloyl-3β, 16α, 21β, 22α, 28-pentahydroxyolean-12-ene G) 3-O-[β-D-galactopyranosyl(1→2)]-α-L-arabinofuranosyl(1→3)-β-D-glucuronopyranosyl-21, 22-O-dibenzoyl-3β, 15α, 16α, 21β, 22α, 28-hexahydroxyolean-12-ene, H) 3-O-[β-D-galactopyranosyl(1→2)]-α-L-arabinofuranosyl(1→3)-β-D-glucuronopyranosyl-21-O-(3,4-dibenzoyl)-α-L-rhamnophyranosyl-22-O-acetyl-3β, 16α, 21β, 22α, 28-pentahydroxyolean-12-ene I) 3-O-[β-D-glucopyranosyl-(1→2)]-α-L-arabinofuranosyl (1→3)-β-D-glucuronopyranosyl-21, 22-O-dibenzoyl-3β, 15α, 16α, 21β, 22α, 24β, 28-heptahydroxyolean-12-ene J) 3-O-[β-galactopyranosyl (1→2)]-α-arabinofuranosyl (1→3)-β-glucuronopyranosyl-21,22-O-dibenzoyl-3β, 16α, 21β, 22α, 28-pentahydroxyolean-12-ene K) 3-O-[β-galactopyranosyl (1→2)]-α-arabinofuranosyl (1→3)-β-glucuronopyranosyl-21-O-(3,4-dibenzoyl)-α-rhamnopyranosyl-28-O-acetyl-3β,16α,21β,22α, 28-pentahydroxyolean-12-ene L) 3-O-[β-galactopyranosyl (1→2)]-α-arabinofuranosyl (1→3)-β-glucuronopyranosyl-21,22-O-dibenzoyl-3β, 16α, 21β, 22α, 28-pentahydroxyolean-12-ene M) 3-O-[β-D-galactopyranosyl (1→2)]-β-D-xyopyranosyl (1→3)-β-D-glucuronopyranosyl-21, 22-O-dibenzoyl-3β, 15α, 16α, 21β, 22α, 28-hexahydroxyolean-12-ene, N) 3-O-[β-D-galactopyranosyl(1→2)]-β-D-xyopyranosyl (1→3)-β-D-glucuronopyranosyl-21-O-(3,4-dibenzoyl)-α-L-rhamnophyranosyl-22-O-acetyl-3β, 16α, 21β, 22α, 28-pentahydroxyolean-12-ene O) 3-O-[β-D-glucopyranosyl-(1→2)]-β-D-xyopyranosyl (1→3)-(-D-glucuronopyranosyl-21, 22-O-dibenzoyl-3β, 15α, 16α, 21β, 22α, 28-heptahydroxyolean-12-ene P) 3-O-[β-D-galactopyranosyl(1→2)]-β-D-xyopyranosyl (1→3)-β-D-glucuronopyranosyl -21, 22-O-dibenzoyl-3β, 16α, 21β, 22α, 28-pentahydroxyolean-12-ene Q) 3-O-[β-galactopyranosyl (1→2)]-β-xyopyranosyl (1→3)-β-glucuronopyranosyl-21-O-(3,4 -dibenzoyl)-α-rhamnopyranosyl-28-O-acetyl-3β,16α,21β,22α, 28-pentahydroxyolean-12-ene R) 3-O-[β-galactopyranosyl(1→2)]-β-xyopyranosyl(1→3)-β-glucuronopyranosyl-21,22-O-dibenzoyl-3β, 16α, 21β, 22α, 28-pentahydroxyolean-12-ene S) 3-O-[β-D-galactopyranosyl (1→2)]-β-D-xyopyranosyl (1→3)-β-D-glucuronopyranosyl-21, 22-O-diangeloyl-3β, 15α, 16α, 21β, 22α, 28-hexahydroxyolean-12-ene, T) 3-O-[β-D-galactopyranosyl (1→2)]-β-D-xyopyranosyl (1→3)-β-D-glucuronopyranosyl-21-O-(3,4-diangeloyl)-α-L-rhamnophyranosyl-22-O-acetyl-3β, 16α, 21β, 22α, 28-pentahydroxyolean-12-ene U) 3-O-[β-D-glucopyranosyl-(1→2)]-β-D-xyopyranosyl (1→3)-(-D-glucuronopyranosyl-21, 22-O-diangeloyl-3β, 15α, 16α, 21β, 22α, 24β, 28-heptahydroxyolean-12-ene V) 3-O-[β-galactopyranosyl (1→2)]-β-D-xyopyranosyl (1→3)-β-glucuronopyranosyl-21,22-O-diangeloyl-3β, 16α, 21β, 22α, 28-pentahydroxyolean-12-ene W) 3-O-[β-galactopyranosyl (1→2)]-β-D-xyopyranosyl (1→3)-β-glucuronopyranosyl-21-O- (3,4-diangeloyl)-α-rhamnopyranosyl-28-O-acetyl-3β,16α,21β,22α, 28-pentahydroxyolean-12-ene X) 3-O-[β-D-galactopyranosyl (1→2)]-β-D-xyopyranosyl (1→3)-β-D-glucuronopyranosyl-21, 22-O-diangeloyl-3β, 16α, 21β, 22α, 28-pentahydroxyolean-12-ene This invention provides a composition for regulating or reducing adhesion protein, wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK; wherein blocking the migration, metastasis of cancer cells inhibiting venous insufficiency, particularly hemorrhoids or inhibiting leg swelling, inhibiting cancer growth comprising any of the compounds selected from the following:

A1) 3-O-[β-D-galactopyranosyl 1→2)]-α-L-arabinofuranosyl(1→3)-β-D-glucuronopyranosyl-21-O-angeloyl,22-O-benzoyl-3β, 15α, 16α, 21β, 22α, 28-hexahydroxyolean-12-ene, B1) 3-O-[β-D-galactopyranosyl(1→2)]-α-L-arabinofuranosyl(1→3)-β-D-glucuronopyranosyl-21-O-(3-angeloyl, 4-benzoyl)-α-L-rhamnophyranosyl-22-O-acetyl-3β, 16α, 21β, 22α, 28-pentahydroxyolean-12-ene C1) 3-O-[β-D-glucopyranosyl-(1→2)]-α-L-arabinofuranosyl (1→3)-(-D-glucuronopyranosyl-21-O-angeloyl,22-O-benzoyl-3β, 15α, 16α, 21β, 22α, 24β, 28-heptahydroxyolean-12-ene D1) 3-O-[β-galactopyranosyl (1→2)]-α-arabinofuranosyl (1→3)-β-glucuronopyranosyl-21-O-angeloyl, 22-benzoyl-3β, 16α, 21β, 22α, 28-pentahydroxyolean-12-ene E1) 3-O-[β-galactopyranosyl (1→2)]-α-arabinofuranosyl (1→3)-β-glucuronopyranosyl-21-O—F) (3-angeloyl, 4-benzoyl)-α-rhamnopyranosyl-28-O-acetyl-3β, 16α, 21β, 22α, 28-pentahydroxyolean-12-ene F1) 3-O-[β-galactopyranosyl (1→2)]-α-arabinofuranosyl (1→3)-β-glucuronopyranosyl-21-O-angeloyl, 22-O-benzoyl-3β, 16α, 21β, 22α, 28-pentahydroxyolean-12-ene G1) 3-O-[β-D-galactopyranosyl(1→2)]-α-L-arabinofuranosyl (1→3)-β-D-glucuronopyranosyl-21-O-benzoyl,22 -O-angeloyl-3β, 15α, 16α, 21β, 22α, 28-hexahydroxyolean-12-ene, H1) 3-O-[β-D-galactopyranosyl(1→2)]-α-L-arabinofuranosyl(1→3)-β-D-glucuronopyranosyl-21-O-(3-benzoyl, 4-angeloyl)-α-L-rhamnophyranosyl-22-O-acetyl-3β, 16α, 21β,22α,28-pentahydroxyolean-12-ene I1) 3-O-[β-D-glucopyranosyl-(1→2)]-α-L-arabinofuranosyl (1→3)-(-D-glucuronopyranosyl-21 -O-benzoyl, 22-O-angeloyl-3β, 15α, 16α, 21β, 22α, 24β, 28-heptahydroxyolean-12-ene J1) 3-O-[β-galactopyranosyl (1→2)]-α-arabinofuranosyl (1→3)-β-glucuronopyranosyl-21-O-benzoyl, 22-O-angeloyl-3β, 16α, 21β, 22α, 28-pentahydroxyolean-12-ene K1) 3-O-[β-galactopyranosyl (1→2)]-α-arabinofuranosyl (1→3)-β-glucuronopyranosyl-21-O-(3 -benzoyl, 4-angeloyl)-α-rhamnopyranosyl-28-O-acetyl-3β, 16α, 21β, 22α, 28-pentahydroxyolean-12-ene L1) 3-O-[β-galactopyranosyl (1→2)]-α-arabinofuranosyl (1→3)-β-glucuronopyranosyl-21-O-benzoyl, 22-O-angeloyl-3β, 16α, 21β, 22α, 28-pentahydroxyolean-12-ene M1) 3-O-[β-D-galactopyranosyl (1→2)]-β-D-xyopyranosyl (1→3)-β-D-glucuronopyranosyl-21 -O-angeloyl, 22-O-benzoyl-3β, 15α, 16α, 21β, 22α, 28-hexahydroxyolean-12-ene, N1) 3-O-[β-D-galactopyranosyl(1→2)]-β-D-xyopyranosyl (1→3)-β-D-glucuronopyranosyl-21-O-(3-angeloyl, 4-dibenzoyl)-α-L-rhamnophyranosyl-22-O-acetyl-3β, 16α, 21β, 22α, 28-pentahydroxyolean-12-ene O1) 3-O-[β-D-glucopyranosyl-(1→2)]-β-D-xyopyranosyl (1→3)-(-D-glucuronopyranosyl-21 -O-21 -O-angeloyl, 22-O-benzoyl-3β, 15α, 16α, 21β, 22α, 24β, 28-heptahydroxyolean-12-ene, P1) 3-O-[β-galactopyranosyl (1→2)]-β-D-xyopyranosyl (1→3)-β-D-glucuronopyranosyl-2121 -O-angeloyl, 22-O-benzoyl-3β, 16α, 21β, 22α, 28-pentahydroxyolean-12-ene Q1) 3-O-[β-galactopyranosyl (1→2)]-β-xyopyranosyl (1→3)-β-glucuronopyranosyl-21-O-(3-angeloyl, 4 -dibenzoyl)-α-rhamnopyranosyl-28-O-acetyl-3β, 16α, 21β, 22α, 28-pentahydroxyolean-12-ene, R1) 3-O-[β-galactopyranosyl (1→2)]-β-xyopyranosyl (1→3)-β-glucuronopyranosyl-angeloyl, 22-O-benzoyl -3β, 16α, 21β, 22α, 28-pentahydroxyolean-12-ene, S1) 3-O-[β-D-galactopyranosyl (1→2)]-β-D-xyopyranosyl (1→3)-β-D-glucuronopyranosyl-21-O-benzoyl, 22-O-angeloyl-3β, 15α, 16α, 21β, 22α, 28-hexahydroxyolean-12-ene, T1) 3-O-[β-D-galactopyranosyl (1→2)]-β-D-xyopyranosyl (1→3)-β-D-glucuronopyranosyl-21-O-(3-benzoyl, 4-angeloyl)-α-L-rhamnophyranosyl-22-O-acetyl-3β, 16α, 21β, 22α, 28-pentahydroxyolean-12-ene, U1) 3-O-[β-D-glucopyranosyl-(1→2)]-β-D-xyopyranosyl (1→3)-(-D-glucuronopyranosyl-21-O-benzoyl, 22-O-angeloyl-3β, 15α, 16α, 21β, 22α, 24β, 28-heptahydroxyolean-12-ene V1) 3-O-[β-galactopyranosyl (1→2)]-β- D-xyopyranosyl (1→3)-β-glucuronopyranosyl-21-O-benzoyl, 22-O-angeloyl-3β, 16α, 21β, 22α, 28-pentahydroxyolean-12-ene W1) 3-O-[β-galactopyranosyl (1→2)]-β-D-xyopyranosyl (1→3)-β-glucuronopyranosyl-21-O-(3-benzoyl,4-angeloyl)-α-rhamnopyranosyl-28-O-acetyl-3β, 16α, 21β, 22α, 28-pentahydroxyolean-12-ene X1) 3-O-[β-D-galactopyranosyl(1→2)]-β-D-xyopyranosyl (1→3)-β-D-glucuronopyranosyl-21-O-benzoyl, 22-O-angeloyl-3β, 16α, 21β, 22α, 28-pentahydroxyolean-12-ene.

Triterpenoid saponins with the characteristic structures mentioned above in this invention can be used to inhibit venous insufficiency, particularly hemorrhoids or inhibit leg swelling, Triterpenoid saponins with the characteristic structures mentioned above in this invention can be used to block the migration, metastasis of cancer cells, reduce or inhibit cancer growth. The cancers are included but not limited to Leukemia cancer, Lung cancer, Colon cancer, CNS cancer, Melanoma cancer, Ovarian cancer, Renal cancer, Prostate cancer, Breast cancer, bladder cancer, cervix cancer, liver cancer, bone cancer, brain cancer and Skin cancer. Triterpenoid saponins with the characteristic structures mentioned above in this invention can be used to affect cell membrane structure and adhesion process. In an embodiment, it provides a method of regulating or reducing adhesion proteins to blocks the migration, metastasis of cancer cells, growth of cancers. In an embodiment, the method comprises reducing the adhesion ability of the cancer cells. In an embodiment, the adhesion proteins comprise IgSF CAM, Selectins, Integrin or Cadherins. In an embodiment, the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK; In an embodiment, the compound is a triterpenoidal saponin or sapogenin, wherein the triterpenoidal saponin comprises at least any one or two of an angeloyl group, tigloyl group, or senecioyl group, or their combinations thereof at carbon 21 and/or 22, or 28, directly attached to the sapogenin or attached to a sugar moiety can be used to treat varicose vein disease, inhibit venous insufficiency, particularly hemorrhoids or inhibit leg swelling, reduce or inhibit cancer growth. In an embodiment, the compound is a five ring triterpene saponin comprising at least two angeloyl groups, tigloyl group, or senecioyl group, or their combinations thereof and a sugar moiety. The angeloyl groups are attached to a side chain at the end of the five rings and a sugar moiety is attached to a side chain of the ring at the other end of the five rings. In an embodiment, the compound comprises at least two angeloyl groups, a tigloyl group, or a senecioyl group, or combinations thereof and a sugar moiety. The angeloyl groups and the sugar moiety are attached to the side chains of the backbone of the compound respectively. In an embodiment, the angeloyl can be replaced by a functional group which functions as an angeloyl group. In an embodiment, a sugar moiety or chain is at C3 or other positions, comprising one or more sugar selected from, but is not limited to glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, or derivatives thereof, or the combination thereof preferably D-glucose, D-galactose, L-rhamnose, L-arabinose, alduronic acids of D-glucuronic acid or D-galacturonic acid, or their combinations thereof, or their derivatives thereof. In a further embodiment, $CH_3$ or $CH_2OH$ or COOH or acetyl group may attach at C 23-30 independently. The activities of a saponin compound for regulating or inhibiting tumor cell growth are based on or attributed to its structure that has the functional group(s) such as angeloyl group, tigloyl group, senecioyl group or acetyl group, or their combinations thereof.

This invention provides a composition comprising the compounds with the structure of:

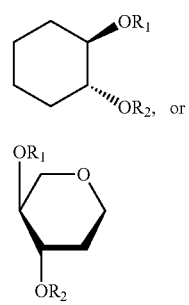

wherein R1 and R2 comprise angeloyl groups, tigloyl groups, senecioyl groups or acetyl group or their combinations, preferable wherein the R1 and R2 comprise angeloyl groups. In an embodiment, R1 and R2 comprise compounds selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof.

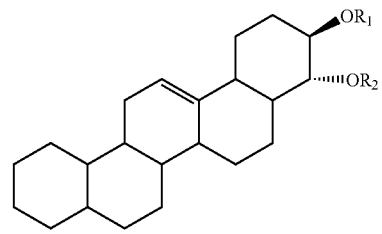

wherein R1 and R2 comprise angeloyl groups, tigloyl groups, senecioyl groups or acetyl group or their combinations, preferable wherein the R1 and R2 comprise angeloyl groups.

In an embodiment, R1 and R2 comprise compounds selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof.

In an embodiment, the compound further comprises a sugar moiety.

In a further embodiment, the sugar moiety comprises glucose, galactose or arabinose or combination thereof.

In an embodiment, the sugar moiety comprises at least one sugar, or glucose, or galactose, or rhamnose, or arabinose, or xylose, or alduronic acid, or glucuronic acid, or galacturonic acid, or their derivative thereof, or the combination thereof.

In an embodiment, the R1 or R 2 may be attached in other position of the structure.

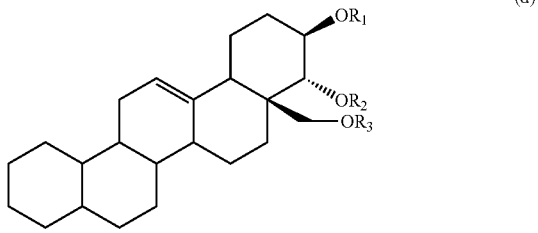

(d)

wherein R1, R2 or R3 comprise angeloyl groups, tigloyl groups, senecioyl groups or acetyl group or their combinations, preferable wherein at least two of the R1, R2 and R3 comprise angeloyl groups. In embodiment, at least two of R1, R2 and R3 comprise compounds selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof.

In an embodiment, at least one of R1, R2 and R3 comprise a sugar moiety comprising two compounds selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof.

In an embodiment, the compound comprises a sugar moiety. In an embodiment, the sugar moiety is attached at one end of structure (d), opposite to R1, R2 and R3. In a further embodiment, the sugar moiety comprises glucose, galactose or arabinose or combination thereof.

In a further embodiment, the sugar moiety comprises at least one sugar, or glucose, or galactose, or rhamnose, or arabinose, or xylose, or alduronic acid, or glucuronic acid, or galacturonic acid, or their derivative thereof, or the combination thereof.

In a further embodiment, the sugar moiety comprises one or more sugar selected from, but is not limited to glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, or derivatives thereof, or the combination thereof. In an embodiment, the R1, R 2 and R3 may be attached in other position of the structure.

In an embodiment, the compound is triterpenoid saponin comprise comprises at least two angeloyl groups, tigloyl groups, senecioyl groups or acetyl group or their combinations, preferable wherein at least two angeloyl groups.

In an embodiment, at least two compounds selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof.

In an embodiment, at least one of the side bonds comprise a sugar moiety comprising two compounds selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof.

In an embodiment, the compound comprises a sugar moiety. In a further embodiment, the sugar moiety comprises glucose, galactose or arabinose or combination thereof. In a further embodiment, the sugar moiety comprises at least one sugar, or glucose, or galactose, or rhamnose, or arabinose, or xylose, or alduronic acid, or glucuronic acid, or galacturonic acid, or their derivative thereof, or the combination thereof.

In a further embodiment, the sugar moiety comprises one or more sugar selected from, but is not limited to glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, or derivatives thereof, or the combination thereof.

In an embodiment, a triterpene comprise the following structure has activities of reducing adhesion proteins to blocks the migration, metastasis of cancer cells, growth of cancers.

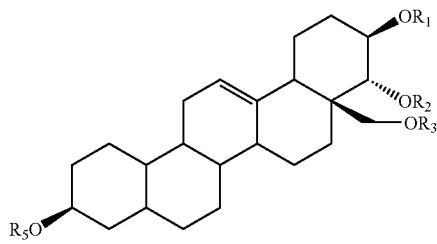

wherein at least two of R1, R2 and R3 comprise compounds selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof. In an embodiment, at least one of R1, R2 and R3 comprise a sugar moiety comprising two compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof. In embodiment, R1, R2 or R3 comprise angeloyl groups, tigloyl groups, senecioyl groups or acetyl group or their combinations, preferable wherein at least two of the R1, R2 and R3 comprise angeloyl groups.

In an embodiment, R5 comprises sugar moiety. In an embodiment, the sugar moiety comprises at least one sugar, or glucose, or galactose, or rhamnose, or arabinose, or xylose, or alduronic acid, or glucuronic acid, or galacturonic acid, or their derivative thereof, or the combination thereof. In an embodiment, the sugar moiety comprises one or more sugar selected from, but is not limited to glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, or derivatives thereof, or the combination thereof. In an embodiment, the sugar moiety comprise glucose, galactose or arabinose, or combination thereof, or derivatives thereof. In an embodiment, the sugar moiety comprise alduronic acids, galactose and arabinose, wherein the alduronic comprise glucuronic acid or galacturonic acid. In an embodiment, the sugar moiety comprise alduronic acids, glucose and arabinose, wherein the alduronic comprise glucuronic acid or galacturonic acid.

In an embodiment, the R1, R 2 and R3 may be attached in other position of the structure.

In an embodiment, the compound is triterpenoid saponin comprise comprises at least two angeloyl groups, tigloyl groups, senecioyl groups or acetyl group or their combinations, preferable wherein at least two angeloyl groups.

In an embodiment, at least two compounds selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof.

In an embodiment, at least one of the side bonds comprise a sugar moiety comprising two compounds selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof.

In an embodiment, the compound comprises a sugar moiety. In a further embodiment, the sugar moiety comprises glucose, galactose or arabinose or combination thereof.

In a further embodiment, the sugar moiety comprises at least one sugar, or glucose, or galactose, or rhamnose, or arabinose, or xylose, or alduronic acid, or glucuronic acid, or galacturonic acid, or their derivative thereof, or the combination thereof.

In a further embodiment, the sugar moiety comprises one or more sugar selected from, but is not limited to glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, or derivatives thereof, or the combination thereof.

A composition comprising an effective amount of compound selected from the above formula or a salt, ester, metabolite or derivative thereof as a medicament for regulating or reducing adhesion protein, blocking the migration, metastasis of cancer cells, inhibiting tumor or cancer cell growth and for treating cancer, wherein the cancers comprise breast, leukocyte, liver, ovarian, bladder, prostate, skin, bone, brain, leukemia, lung, colon, CNS, melanoma, renal and cervix cancer.

In a further embodiment, a compound or sapongenin comprises the structure (d) or (e) has anti-cancer or inhibiting virus activities.

A composition for regulating or reducing adhesion protein, blocking the migration, metastasis of cancer cells, treating cancers or inhibiting virus, comprising a compound, wherein the compound is a triterpene, which comprises at least two side chains which comprise angeloyl groups, wherein the side chains are at adjacent carbon in trans position. In an embodiment, the side chains are at alternate carbon in cis position. In an embodiment, the side chains are at alternate carbon in trans position. In an embodiment, the side chains are attached an acyl. In an embodiment, the side chains are attached an unsaturated group.

In an embodiment, the side chains are in non-adjacent carbon cis or trans position. In an embodiment, the side chains comprise a functional group capable of performing the function of angeloyl group.

The above compounds can be used for regulating or reducing adhesion protein, blocking the migration, metastasis of cancer cells, inhibiting tumor cell growth, reducing leg swelling, symptoms of chronic venous insufficiency, peripheral edema, antilipemic, chronic venous disease, varicose vein disease, varicose syndrome, venous stasis, expectorant, peripheral vascular disorders, by administering to a subject in need thereof, an effective amount of the above described compounds.

This invention provides a method for inhibiting tumor cell growth, regulating cell growth, reducing inflammation, in a subject, comprising administering to a subject, in need thereof, an effective amount of the compound which comprises any of the above structures to said subject. The cancers are included but not limited to Leukemia cancer, Lung cancer, Colon cancer, CNS cancer, Melanoma cancer, Ovarian cancer, Renal cancer, Prostate cancer, Breast cancer, bladder cancer, cervix cancer, liver cancer, bone cancer, brain cancer and Skin cancer.

This invention also provides a method for reducing swelling, reducing symptoms of chronic venous insufficiency, peripheral edema, antilipemic, chronic venous disease, varicose vein disease, varicose syndrome, venous stasis, Expectorant, peripheral vascular disorders, cerebro-organic convulsion, cerebral circulation disorder, cerebral edema, psychoses, dysmenorrheal, hemorrhoids, episiotomies, peripheral edema formation or postoperative swelling; for reducing symptoms of leg pain; for treating pruritis, lower leg volume, for reducing symptoms of pain; thrombosis, thromophlebitis; for preventing gastric ulcers antispasmotic, comprising administering to a subject, in need thereof, an effective amount of the composition of this invention.

This invention provides a composition comprising the compounds provided in the invention for treating cancers; for inhibiting virus; for preventing cerebral aging; for improving memory; improving cerebral functions, for curing enuresis, frequent micturition, urinary incontinence, dementia, Alzheimer's disease, autism, brain trauma, Parkinson's disease or other diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; cerebrovascular disease; inhibiting NF-Kappa B activation; for treating brain edema, sever acute respiratory syndrome, respiratory viral diseases, chronic venous insufficiency, hypertension, chronic venous disease, anti-edematous, anti inflammatory, hemorrhoids, peripheral edema formation, varicose vein disease, flu, post traumatic edema and postoperative swelling; for inhibiting blood clot, for inhibiting ethanol absorption; for lowering blood sugar; for regulating the adrenocorticotropin and corticosterone level. This invention provides a composition for AntiMS, antianeurysm, antiasthmatic, antibradykinic, anticapillarihemorrhagic, anticephalagic, anticervicobrachialgic, antieclamptic, antiedemic, antiencaphalitic, antiepiglottitic, antiexudative, antiflu, antifracture, antigingivitic, antihematomic, antiherpetic, antihistaminic, antihydrathritic, antimeningitic, antioxidant, antiperiodontic, antiphlebitic, antipleuritic, antiraucedo, antirhinitic, antitonsilitic, antiulcer, antivaricose, antivertiginous, cancerostatic, corticosterogenic, diuretic, fungicide, hemolytic, hyaluronidase inhibitor, lymphagogue, natriuretic, pesticide, pituitary stimulant, thymolytic, vasoprotective, and venotonic treatment.

Alkenyl means unsaturated linear or branched structures and combinations thereof, having 1-7 carbon atoms, one or more double bonds therein. Non-limiting examples of alkenyl groups include vinyl, propenyl, isopropenyl, butenyl, s- and t-butenyl, pentenyl, hexenyl, butadienyl, pentadienyl, and hexadienyl.

An aryl is a functional group of organic molecule derived from an aromatic compound such as benzene, a 6-14 membered carbocyclic aromatic ring system comprising 1-3 benzene rings. If two or more aromatic rings are present, then the rings are fused together, so that adjacent rings share a common bond. Examples include phenyl and naphthyl. The aryl group may be substituted with one or more substitutes independently selected from halogen, alkyl or alkoxy.

Acyl is a functional group obtained from an organic acid by the removal of the carboxyl. Acyl groups can be written as having the general formula —COR, where there is a double bond between the carbon and oxygen. The names of acyl groups typically end in -yl, such as formyl, acetyl, propionyl, butyryl and benzoyl.

Benzoyl is one of acyls, $C_6H_5COR$, obtained from benzoic acid by the removal of the carboxyl.

Heterocyclic compound—a compound containing a heterocyclic ring which refers to a non-aromatic ring having 1-4 heteroatoms said ring being isolated or fused to a second ring selected from 3- to 7-membered alicyclic ring containing 0-4 heteroatoms, aryl and heteroaryl, wherein said heterocyclic comprises pyrrolidinyl, pipyrazinyl, morpholinyl, trahydrofuranyl, imidazolinyl, thiomorpholinyl, and the like.

Heterocyclyl groups derived from heteroarenes by removal of a hydrogen atom from any ring atom.

Alkanoyl is the general name for an organic functional group RCO—, where R represents hydrogen or an alkyl group. Preferably alkanoyl is selected from acetyl, propionoyl, butyryl, isobutyryl, pentanoyl and hexanoyl.

Alkenoyl is alkenylcarbonyl in which alkenyl is defined above. Examples are pentenoyl(tigloyl) and hexenoyl(angeloyl).

Alkyl is a radical containing only carbon and hydrogen atoms arranged in a chain, branched, cyclic or bicyclic structure or their combinations, having 1-18 carbon atoms. Examples include but are not limited to methyl, ethyl, propyl isopropyl, butyl, s- and t-butyl, pentyl, hexyl, heptyl, octyl, nonyl, undecyl, dodecyl, tridecyl, tetradecyl, pentadecyl, cyclopropyl, cyclobutyl, cyclopentyl and cyclohexyl.

Benzoyl alkyl substituted alkanoyl is refer to straight or branched $C_1$-$C_6$ alkanoyl substituted with at least one benzoyl and at least one alkyl, wherein the benzoyl is attached to a straight or branched $C_1$-$C_6$ alkyl. Preferably a benzoyl alkyl substituted alkanoyl is benzoyl methyl isobutanoyl.

A sugar moiety is a segment of molecule comprising one or more sugars or derivatives thereof or alduronic acid thereof.

Isobutyryl is Synonym of 2-Methylpropanoyl

Y and Y3 represent the same compound.

YM and (ACH-Y) represent the same compound.

This invention provides a method of altering the characteristic of cancer cell membrane to block the migration, metastasis of cancer cells or inhibit the growth of cancers or anti-angiogenesis.

This invention provides a method of inhibiting the growth, migration, metastasis of cancer by altering the characteristic of membrane of cancer cell, wherein the characteristic comprise adhesion protein; wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer, wherein the method is administering contacting Xanifolia Y0, Y1, Y2, Y, Y7, Y8, Y9, Y10, or a salt, ester, metabolite thereof.

This invention provides a composition and method for inhibiting the growth, migration, metastasis of cancer by altering the adhesion characteristic of membrane of cancer cell, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer, wherein the method is administering contacting Xanifolia Y0, Y1, Y2, Y, Y7, Y8, Y9, Y10, or a salt, ester, metabolite thereof. In an embodiment the method is administering contacting the compound selected from formula in this application.

This application shows Xanifolia-Y is an alternate or supplemental agent to DNA-inhibition or microtubule-targeting drugs. It could be beneficial if it is used singly or in combination with other drugs of different mechanisms (block M-phase progression or DNA synthesis). Our inventions show combined effect of Xanifolia-Y and paclitaxel on inhibition of ES2 cells' growth (Detail in Experiment 14 U.S. Ser. No. 11/683,198, filed on Mar. 7, 2007)

Identify the binding target of Xanifolia-Y of adhesion proteins and signaling proteins in ovarian cancer cells.

In our animal studies, it was shown that Xanifolia-Y extended the life span of tumor bearing mice. (See Experiments 7, 8, 9 in U.S. Ser. No. 11/683,198, filed on Mar. 7, 2007,). The animals died sooner if the treatment of Xanifolia-Y was delayed (comparing results of treatments started from 1, 4 or 10 days after tumor inoculation). The results show that Xanifolia-Y inhibits migration or metastasis of the inoculated cancer cells. Ovarian carcinoma cells express high levels of adhesion molecules. Adhesion proteins are present in both cancer cells and mesothelial cells. While the lost of adhesion blocks of the protein accessibility due to a result of modulating by Xanifolia-Y, In an embodiment, the interaction of Xanifolia-Y with membrane alter the adhesion protein's binding site(s).

We have shown that Xanifolia-Y are cytotoxic to tumor cells, In an embodiment it kills ovarian cancer cells. Our inventions show that Xanifolia-Y inhibits cancer cell growth and prolongs life-span of tumor bearing mice. Our studies also indicate that the sooner the drug-treatment, the longer the life-span of the tumor bearing animals is extended. Xanifolia-Y also has an effect in blocking or inhibiting migration or metastasis. The delay of Xanifolia-Y-treatment allows more chances for cancer cells to metastasize to the mesothelium lining in the peritoneal cavity which resulted in more tumor growth and shorter life span. Adhesive molecules play an important role in cell migration and metastasis. It was shown in our studies that Xanifolia-Y inhibits cell attachment to culture flasks. Our experiment showed that Xanifolia-Y family inhibits the secretion of adhesion protein. Xanifolia-Y interferes with the function of the adhesive molecules. In embodiment Xanifolia-Y blocks the function of the adhesive molecules. In an embodiment, Xanifolia-Y modulates adhesive proteins. It is masking the adhesive proteins. In an embodiment, Xanifolia-Y indirectly alters membrane structure that cause changes in protein conformation, or locations and result in loss of adhesion process. In an embodiment, the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK, particular fibronectin.

Fibronectin is a kind of glycoprotein that binds to membrane spanning receptor proteins comprising the integrins, collagen, fibrin and heparin sulfate. Fibronectin has been implicated in tumor development and metastasis. This application provides methods and compositions for modulating the gene expression of fibronectin, inhibiting the secretion, expression, or synthesis of fibronectin, reducing the receptors of fibronectin, reducing the adhesion ability fibronectin, inhibiting the metastasis, or inhibiting cancer growth, wherein the method and composition comprises administering to the said subject as effective amount of compounds selected in this application.

Vitronectin is an abundant glycoprotein found in blood plasma and the extracellular matrix. Vitronectin is involved in hemostasis and tumor malignancy. This application provides methods and compositions for modulating the gene expression of vitronectin, reducing the receptors of vitronectin, reducing the adhesion ability Vitronectin, inhibiting the metastasis, and inhibiting cancer growth, wherein the method and composition comprises administering of compounds selected in this application.

Integrins are cell surface receptors that interact with the extracellular matrix. They define cellular shape, mobility, and regulate the cell cycle. Integrin plays a role in the attachment of cells to other cells, and also plays a role in the attachment of a cell to the material part of a tissue. Besides the attachment role, integrin also plays a role in signal transduction. This application provides method and composition for modulating the gene expression of integrins, wherein comprising inhibiting integrins, inhibiting the adhesion ability of integrins, inhibiting cancer cell metastasis and inhibiting cancer growth, wherein the method and composition comprise administering of compounds selected in this application.

Laminins are a family of glycoproteins that are an integral part of the structural scaffolding of basement membranes in almost every animal tissue. They are secreted and incorporated into cell-associated extracellular matrices. Inhibiting the gene expression of laminins will reduce the adhesion ability of cells in order to inhibit the cell migration and metastasis of cancer cells. This application provides method and composition for modulating the gene expression of laminins, wherein comprising inhibiting laminins, inhibiting the adhesion ability of laminins inhibiting cancer cell metastasis and inhibiting cancer growth, wherein the method and composition comprise administering of compounds selected in this application.

CAM (cell adhesion molecules) are proteins located on the cell surface which involve with binding with other cells in an adhesion process. Inhibiting the gene expression of CAM will reduce the adhesion ability of cells and further inhibit the cell migration and metastasis of cancer cells. This application provides method and composition for modulating the gene expression of CAM, wherein comprising inhibiting CAM, inhibiting the adhesion ability of CAM, inhibiting cancer cell metastasis and inhibiting cancer growth, wherein the method and composition comprise administering of compounds selected in this application.

Collagen is the main protein of connective tissue in mammal. Inhibiting the gene expression of collagen will reduce the adhesion ability of cells in order to inhibit the cell migration and metastasis of cancer cells. This application provides methods and compositions for modulating the gene expression of laminins, wherein comprising inhibiting laminins, inhibiting the adhesion ability of laminins inhibiting cancer cell metastasis and inhibiting cancer growth, wherein the method and composition comprise administering of compounds selected in this application.

Tenascin-C (Tn-C) is an extracellular matrix protein on the cell. It is a positive factor for cancer growth, invasion and angiogenesis activities. This application provides methods and compositions for inhibiting Tenascin-C and inhibiting cancer growth, wherein the methods and compositions comprise administering of compounds selected in this application.

Angiogenesis is a process involving the growth of new blood vessels. It is a normal process in growth and development. However, this is also a fundamental step in the transition of tumors from a dormant state to a malignant state. The angiopoietins are protein growth factors that modulate angiogenesis. The identified angiopoietins comprise angiopoietin 1, angiopoietin 2, angiopoietin 3, angiopoietin 4, angiopoietin 5, angiopoietin 6, angiopoietin 7, angiopoietin-like 1, angiopoietin-like 2, angiopoietin-like 3, angiopoietin-like 4, angiopoietin-like 5, angiopoietin-like 6, and angiopoietin-like 7. In an embodiment, the angiopoietin 1 is a positive factor to promote the new blood vessels. In embodiment, the angiopoietin 2 is antagonist of angiopoietin 1, which is a negative factor for the growth of new blood vessels. This application provides methods and compositions for modulating angiopoietin and inhibiting cancer growth; wherein the cancers comprise breast, leukocyte, liver, ovarian, bladder, prostate, skin, bone, brain, leukemia, lung, colon, CNS, melanoma, renal and cervix cancer, wherein the methods and compositions comprise administering to the said subject as effective amount of compounds selected in this application. The compounds in this application are positive regulating angiopoietin 2. The compounds in this application are negative regulating the angiopoietin 1. The results of the micro array experiment showed that compound Y and YM (ACH-Y) modulate the gene expression of angiopoietin family in ES2 cells. They promote angiopoietin 2 and inhibit angiopoietin 1 and angiopoietin-like 1 and angiopoietin-like 4.

The compounds in this application are anti-angiogenesis, inhibiting cancer cell metastasis and inhibiting cancer growth, wherein the compounds comprise Xanifolia Y0, Y1, Y2, Y, Y7, Y8, Y9, Y10, ACH-Y or a salt, ester, metabolite thereof and compounds selected from formula (1A), (1B), (1C) and (1D). In an embodiment the method is administering contacting the compound in this application comprising Xanifolia Y0, Y1, Y2, Y, Y7, Y8, Y9, Y10, Xanifolia (x), Escin or Aescin or a salt, ester, metabolite thereof. In an embodiment the compound may be selected from formulas (1A), (1B), (1C) and (1D). In an embodiment, the compound comprises a triterpene backbone, two angeloyl groups and sugar moiety. In an embodiment the compound(s) are selected from Compound A to X and A1 to X1 in the application. In an embodiment the compound(s) are selected from Compound Z1 to Z7 in the application.

Data obtained from our Microarray experiments disclose that Xanifolia Y modulates gene expression of the following genes (represented by gene symbol):

Gene Symbol: ABL2, ADAMTS1, AKR1C3, AMIGO2, ANGPT2, ANKRD11, AP2B1, APEH, APLP2, ARL10C, ARMC4, ARMCX1, ARMCX6, ARNTL2, ARNTL2, ATF3, ATP6V0E, ATP6V1B2, ATP6V1C1, ATP6V1C1, BCL2A1, BCL6, BRI3, BTD, C14orf109, C14orf78, C17orf32, C6orf65, C9orf10, C9orf103, CAD, CAV1, CAV2, CBLL1, CCL20, CD33L3, CEBPB, CEP4, CFH///CFHL1, CHRDL1, CITED2, CITED2, CLDN14, CLN8, CLTA, CNAP1, COG6, COL18A1, COL4A2, COL5A1, COL5A2, COL6A3, COPG, CPM, CPNE3, CPSF1, CSRP2BP, CSTB, CTNS, CXCL2, DDB1, DDIT3, DDX20, DKFZP56411171, DKFZP586JO619, DUSP10, DUSP10, DYRK3, EEF2K, EFEMP1, EMP1, EVC, EVI2A, EXT2, FAM62A, FER1L3, FLJ14466, FLNA, FN1, FN1, GANAB, GDF15, GEM, GNPDA1, GPAA1, GPC6, GPNMB, GPNMB, GUSB, H2AFV, H2AFV, HDAC9, HDLBP, HECW2, HMGA2, HMOX1, HSDL2, HSPBAP1, HSPC196, HYOU1, IDS, IGFBP3, IKBKAP, INSIG1, IP04, IRS2, JAG1, KDELR3, KIAA0251, KIAA0586, KIAA1211, KIAA1462, KIAA1706, KIAA1754, KRT18, KRT7, KRTAP4-7, LAMP2, LEPR, LEPREL1, LHFPL2, LIF, LOC286044, LOC339229, LOC90693, LRRC8E, MAFG, MAGED2, MCTP1, MGC16291, MGC19764, MGC5618, MRPS30, MRPS31, MTERFD3, MYH9, NAGA, NAV2, NCSTN, NEK9, NEU1, NFKBIZ, NMT2, NPC2, NSUN5C, NTNG1, NUP188, OACT2, OS9, P4HA1, P8, PALM2-AKAP2, PALM2-AKAP2, PARVA, PBX2, PDE4DIP, PDIA4, PDIA6, PEG10, PHF19, PIK4CA, PLEKHM1, PLOD1, PLOD2, PPP1R15A, PPP1R15A, PRKDC, PRSS23, PRSS23, PSEN2, PSMD1, PTPRF, PTPRJ, RAB32, RAB9A, RG9MTD1, RGS4, RHOQ, RND3, RNF25, RNPEP///UBE2V1///Kua///Kua-UEV, RNU17D, ROBO4, RRAGC, RRS1, SEC31L1, SERPINB2, SERPINB7, SESN2, SGEF, SGSH, SKIV2L, SLC25A21, SLC35A3, SLC3A2, SMARCA1, SNAPC1, SNF1LK, SPOCD1, SPTAN1, SQSTM1, ST3GAL6, STC2, STX3A, TFPI2, TFPI2, TGFBI, TGM2, THRAP1, TLN1, TMEM60, TNFAIP3, TRIB3, TRIO, TSC2, UAP1L1, UBAP2L, UPP1, URB, USP11, USP5, VDR, WDR4, YTHDF2, ZCCHC9, ZDHHC20, ZFHX1B, ZNF185, ZNF278, ZNF690, ZNF697

Our experiment disclosed that Xanifolia Y and ACH-Y inhibited genes expression of the following genes: FN1, ITGAV, LAMA4, LAMB2, LAMC1, LAMB1, LAMB1, LAMA4, LAMA5, LAMC1, LAMA2, LAMB1, LAMA3, SCAMP1, TICAM2, SCAMP1, TICAM2, SCAMP1, SCAMP1, CAMK2B, DL1, ICAM3, CEECAM1, ICAM5, SCAMP1, CAMK1G, CAMSAP1, MCAM, CAMTA1, CKN1, ALCAM, DCAMKL2, CEACAM3, CAMK2D, CAMK2B, SCAMP5, CAMK4, NCAM1, CAMK2G, MYH9, MYH10, MYO1D, MYO5A, MYLK, MYO6, MYO5A, MYO1C, MYLK, MYO6, MYLC2PL, MYO10, MYO6, TPM3, MYO1C, BECN1, MYO1E, TPM3, M-RIP, MYO1B, MYO10, MYO5A, M-RIP, MYO10, MYL6, MYOHD1, BECN1, TPM4, MYLK, MYH10, MYOHD1, LOC221875, LOC402643, MYO15B, LOC129285, MYH11, MYO1B, MYO1C, MYO9B, CDH13, CTNNAL1, CDH13, CDH12, CTNNB1, CDH5, CTNND1, CDH2, CTNNA1, CDH2, PCDHB16, CTNNA1, CELSR2, PCDHB6, PCDHB7, CTNND2, PCDHGC3, PCDHGB4, PCDHGA8, PCDHGA12, PCDHGC5, PCDHGC4, PCDHGB7, PCDHGB6, PCDHGB5, PCDHGB3, PCDHGB2, PCDHGB1, PCDHGA11, PCDHGA10, PCDHGA9, PCDHGA7, PCDHGA6, PCDHGA5, PCDHGA4, PCDHGA3, PCDHGA2, PCDHGA1, CTNND1, CDH23, PCDHB12, PCDHB10, PCDH18, CDH20, PCDH9, PCDHGA12, PCDHGA11, PCDHGA10, PCDHGA6, PCDHGA5, PCDHGA3, PCDH7, CDH18, CDH6, CCBE1, COL10A1, COL12A1, COL13A1, COL18A1, COL1A1, COL21A1, COL4A1, COL4A2, COL4A5, COL4A6, COL5A1, COL5A2, COL6A1, COL6A2, COL6A3, COL9A1, MMP9, P4HA1, P4HA2, P4HB, PCOLCE, PCOLCE2, PCOTH, PLOD1, PLOD2, PLOD3, CIB1, ILK, ITGA2, ITGA3, ITGA4, ITGA6, ITGAV, ITGB1, ITGB1BP1, ITGB2, ITGB5, ITGBL1, TNC, EMILIN1, ICAM1, HSPG2, HPSE, HS2ST1, SDC2, This invention provides methods of regulating adhesion proteins which are important for blocking migration, metastasis of cancer cells, and inhibiting the growth of cancers. In an embodiment, the method comprises reducing the adhesion ability of the cancer cells. In an embodiment, the adhesion protein comprise fibronectin, integrins family, Myosin, vitronectin, collagen, laminin, Glycosylation cell surface proteins, polyglycans, cadherin, heparin, tenascin, CD 54, CAM, elastin and FAK, particular for fibronectin.

This invention provide processes and methods of contacting the said cells with the said compound or administration by intravenous injection, intravenous drip, intraperitoneal injection or oral administration; A process and method for administration of the composition, wherein administration is by intravenous injection, intravenous drip, intraperitoneal injection or oral administration; wherein administration is by intravenous drip: 0.003-0.03 mg/kg body weight of compound dissolved in 250 ml of 10% glucose solution or in 250 ml of 0.9% NaCl solution, or by intravenous injection: 0.003-0.03 mg/kg body weight per day of compound dissolved in 10-20 ml of 10% glucose solution or of 0.9% NaCl solution, or 0.01-0.03 mg/kg body weight of compound dissolved in 250 ml of 10% glucose solution or in 250 ml of 0.9% NaCl solution, or by intravenous injection: 0.01-0.03 mg/kg body weight per day of compound dissolved in 10-20 ml of 10% glucose solution or of 0.9% NaCl solution, or 0.01-0.05 mg/kg body weight of compound dissolved in 250 ml of 10% glucose solution or in 250 ml of 0.9% NaCl solution, or by intravenous injection: 0.01-0.05 mg/kg body weight per day of compound dissolved in 10-20 ml of 10% glucose solution or of 0.9% NaCl solution, or 0.05-0.2 mg/kg body weight of compound dissolved in 250 ml of 10% glucose solution or in 250 ml of 0.9% NaCl solution, or by intravenous injection: 0.05-0.2 mg/kg body weight per day of compound dissolved in 10-20 ml of 10% glucose solution or of 0.9% NaCl solution, or by intravenous drip: 0.1-0.2 mg/kg body weight per day of compound dissolved in 250 ml of 10% glucose solution or in 250 ml of 0.9% NaCl solution, or by intravenous injection: 0.1-0.2 mg/kg body weight per day compound dissolved in 10-20 ml of 10% glucose solution or of 0.9% NaCl solution, or by intraperitoneal injection (I.P.): 2.5 mg/kg body weight per day compound dissolved in 10% glucose solution or of 0.9% NaCl solution, or by oral administration wherein the dosage of mammal is 1-10 mg/Kg, 10-30 mg/Kg, 30-60 mg/Kg, or 60-90 mg/Kg body weight of compound, or by intravenous injection or intravenous drip wherein the dosage of mammal is 0.01-0.1 mg/Kg body weight, 0.1-0.2 mg/Kg, 0.2-0.4 mg/Kg body weight, or 0.4-0.6 mg/Kg body weight of compound, or by intraperitoneal injection (I.P.) wherein the dosage of mammal is 1-3 mg/Kg, 3-5 mg/Kg, 4-6 mg/Kg, or 6-10 mg/Kg body weight of compound.

The following results are obtained from MicroArray experiments:

Y/D is the ratio (in folds) of gene expression in cells treated with compound Y as compared with those of the no drug control (D), YM/D is the ratio of gene expression in cells treated with compound YM (ACH-Y, Y without sugar moiety) compared with those of the no drug control (D)

TABLE 1

Effect of Y and YM on fibronectin expression in ES2 cells

| Probe Set ID | Y/D | YM/D | Gene.Symbol | Gene.Title |
| --- | --- | --- | --- | --- |
| 212464_s_at | −2.7 | −1.1 | FN1 | fibronectin 1 |
| 216442_x_at | −2.6 | −1.1 | FN1 | fibronectin 1 |
| 211719_x_at | −2.6 | −1.2 | FN1 | fibronectin 1 |
| 210495_x_at | −2.5 | −1.1 | FN1 | fibronectin 1 |

The results of the microarray experiment showed that compound Y and YM(ACH-Y) inhibit fibronectin expression; The expression ratio of compound Y/Y3 to the control are −2.7, −2.6, −2.6, −2.5 folds detected by gene probes 212464_s_at; 216442_x_at; 211719x_at and 210495_x_at, respectively. These results indicate Y/Y3 inhibits fibronectin expression; wherein the YM/ACH-Y also show minor fibronectin inhibition with the inhibiting ratio of −1.1, −1.1, −1.2, −1.1 folds by gene probes 212464_s_at; 216442_x_at; 211719_x_at and 210495_x_at, respectively. The results indicate that while YM is active but is less potent than Y/Y3.

TABLE 2

Effects of Y and YM on integrin (vitronectin receptor) expression in ES2 cells

| Probe Set ID | Y/D | YM/D | Gene.Symbol | Gene.Title |
| --- | --- | --- | --- | --- |
| 202351_at | −1.8 | −1.3 | ITGAV | integrin, alpha V (vitronectin receptor, alpha polypeptide, antigen CD51) |
| 236251_at | −1.4 | −1.4 | ITGAV | Integrin, alpha V (vitronectin receptor, alpha polypeptide, antigen CD51) |

The results of the micro array experiment showed that compound Y and YM(ACH-Y) inhibit integrin (vitronectin receptor) expression; wherein the inhibiting ratio of compound Y/Y3 to the control are −1.8, −1.4, folds as detected by different probes; wherein the inhibiting ratio of YM (ACH-Y) to the control are −1.3, −1.4 folds.

TABLE 3

Effects of Y and YM on laminin expression in ES2 cells

| Probe Set ID | Y/D | YM/D | Gene.Symbol | Gene.Title |
|---|---|---|---|---|
| 202202_s_at | −2.2 | −2.0 | LAMA4 | laminin, alpha 4 |
| 216264_s_at | −2.0 | −2.0 | LAMB2 | laminin, alpha 5 |
| 200770_s_at | −1.9 | −1.1 | LAMC1 | laminin, alpha 6 |
| 211651_s_at | −1.6 | −1.7 | LAMB1 | laminin, alpha 7 |
| 201505_at | −1.6 | −2.0 | LAMB1 | laminin, beta 1 |

The results of the micro array experiment showed that compound Y and YM(ACH-Y) inhibit laminin expression; The expression ratio of compound Y/Y3 to the control are −2.2, −2.0, −1.9, −1.6, −1.6 folds as detected by different probes; wherein the inhibiting ratio of YM/ACH-Y to the control are −2.0, −2.0, 1.1, −1.7, −2.0 folds.

TABLE 4

Effects of Y and YM on CAM expression in ES2 cells

| Probe Set ID | Y/D | YM/D | Gene.Symbol | Gene.Title |
|---|---|---|---|---|
| 201952_at | −1.9 | −1.4 | ALCAM | activated leukocyte cell adhesion molecule |
| 201951_at | −1.9 | −1.7 | ALCAM | activated leukocyte cell adhesion molecule |
| 212425_at | −1.7 | −1.5 | SCAMP1 | Secretory carrier membrane protein 1 |
| 240655_at | −1.6 | −1.3 | ALCAM | Activated leukocyte cell adhesion molecule |
| 212417_at | −1.4 | −1.4 | SCAMP1 | secretory carrier membrane protein 1 |
| 239431_at | −1.3 | −1.3 | TICAM2 | toll-like receptor adaptor molecule 2 |
| 212416_at | −1.3 | −1.1 | SCAMP1 | secretory carrier membrane protein 1 |
| 228234_at | −1.3 | −1.3 | TICAM2 | toll-like receptor adaptor molecule 2 |
| 206667_s_at | −1.3 | −1.5 | SCAMP1 | secretory carrier membrane protein 1 |

The micro array experiment showed that compound Y and YM(ACH-Y) inhibit gene expression related to the adhesion molecule; wherein the inhibiting ratio of compound Y/Y3 to the control are −1.3 to −1.9 folds as detected by different probes; wherein the inhibiting ration of YM/ACH-Y to the control are −1.1 to −1.7 folds.

TABLE 5

Effects of Y and YM on collagen expression in ES2 cells

| Probe Set ID | Y/D | YM/D | Gene.Symbol | Gene.Title |
|---|---|---|---|---|
| 217428_s_at | −3.0 | −1.2 | COL10A1 | collagen, type X, alpha 1(Schmid metaphyseal chondrodysplasia) |
| 231766_s_at | −2.8 | −2.4 | COL12A1 | collagen, type XII, alpha 1 |
| 201438_at | −2.4 | −1.5 | COL6A3 | collagen, type VI, alpha 3 |
| 1556138_a_at | −2.2 | −2.8 | COL5A1 | Collagen, type V, alpha 1 |
| 211809_x_at | −2.0 | −1.5 | COL13A1 | collagen, type XIII, alpha 1 |
| 207543_s_at | −2.0 | −1.5 | P4HA1 | procollagen-proline, 2-oxoglutarate 4-dioxygenase (proline 4-hydroxylase), alpha polypeptide I |
| 213992_at | −2.0 | −1.9 | COL4A6 | collagen, type IV, alpha 6 |
| 211343_s_at | −1.9 | −1.7 | COL13A1 | collagen, type XIII, alpha 1 |
| 211966_at | −1.8 | −1.7 | COL4A2 | collagen, type IV, alpha 2 |
| 200656_s_at | −1.8 | −1.2 | P4HB | procollagen-proline, 2-oxoglutarate 4-dioxygenase (proline 4-hydroxylase), beta polypeptide (protein disulfide isomerase-associated 1) |
| 209081_s_at | −1.7 | −1.5 | COL18A1 | collagen, type XVIII, alpha 1 |
| 202619_s_at | −1.7 | −1.2 | PLOD2 | procollagen-lysine, 2-oxoglutarate 5-dioxygenase 2 |
| 203325_s_at | −1.7 | −2.8 | COL5A1 | collagen, type V, alpha 1 |
| 200827_at | −1.7 | −1.2 | PLOD1 | procollagen-lysine 1,2-oxoglutarate 5-dioxygenase 1 |
| 221730_at | −1.6 | −1.6 | COL5A2 | collagen, type V, alpha 2 |
| 202311_s_at | −1.6 | −3.6 | COL1A1 | collagen, type I, alpha 1 |
| 213110_s_at | −1.6 | −2.2 | COL4A5 | collagen, type IV, alpha 5 (Alport syndrome) |
| 212091_s_at | −1.6 | −1.9 | COL6A1 | collagen, type VI, alpha 1 |
| 213290_at | −1.6 | −1.5 | COL6A2 | collagen, type VI, alpha 2 |
| 211981_at | −1.6 | −2.2 | COL4A1 | collagen, type IV, alpha 1 |
| 200654_at | −1.6 | −1.3 | P4HB | procollagen-proline, 2-oxoglutarate 4-dioxygenase (proline 4-hydroxylase), beta |

TABLE 5-continued

Effects of Y and YM on collagen expression in ES2 cells

| Probe Set ID | Y/D | YM/D | Gene.Symbol | Gene.Title |
|---|---|---|---|---|
|  |  |  |  | polypeptide (protein disulfide isomerase-associated 1) |
| 212489_at | −1.5 | −4.1 | COL5A1 | collagen, type V, alpha 1 |
| 202620_s_at | −1.4 | −1.3 | PLOD2 | procollagen-lysine, 2-oxoglutarate 5-dioxygenase 2 |
| 202733_at | −1.4 | −1.9 | P4HA2 | procollagen-proline, 2-oxoglutarate 4-dioxygenase (proline 4-hydroxylase), alpha polypeptide II |
| 208535_x_at | −1.4 | −1.2 | COL13A1 | collagen, type XIII, alpha 1 |
| 202185_at | −1.3 | −1.1 | PLOD3 | procollagen-lysine, 2-oxoglutarate 5-dioxygenase 3 |
| 202465_at | −1.3 | −1.6 | PCOLCE | procollagen C-endopeptidase enhancer |
| 221729_at | −1.3 | −1.8 | COL5A2 | collagen, type V, alpha 2 |
| 242324_x_at | −1.3 | −1.8 | CCBE1 | collagen and calcium binding EGF domains 1 |
| 1568611_at | −1.3 | −2.4 | P4HA2 | Procollagen-proline, 2-oxoglutarate 4-dioxygenase (proline 4-hydroxylase), alpha polypeptide II |

The results of the micro array experiment showed that compound Y and YM(ACH-Y) inhibit collagen expression. The expression ratio of compound Y/Y3 to the control range from −1.3 to −3.0 folds; wherein the expression ratio of YM/ACH-Y to the control range from −1.1 to −3.6 folds

TABLE 6

Effects of Y and YM on integrin expression in ES2 cells

| Probe Set ID | Y/D | YM/D | Gene.Symbol | Gene.Title |
|---|---|---|---|---|
| 205422_s_at | −1.9 | −2.0 | ITGBL1 | integrin, beta-like 1 (with EGF-like repeat domains) |
| 202351_at | −1.8 | −1.3 | ITGAV | integrin, alpha V (vitronectin receptor, alpha polypeptide, antigen CD51) |
| 1557080_s_at | −1.7 | −2.5 | ITGBL1 | Integrin, beta-like 1 (with EGF-like repeat domains) |
| 214927_at | −1.7 | −1.8 | ITGBL1 | Integrin, beta-like 1 (with EGF-like repeat domains) |
| 205885_s_at | −1.7 | −2.0 | ITGA4 | integrin, alpha 4 (antigen CD49D, alpha 4 subunit of VLA-4 receptor) |
| 213416_at | −1.6 | −1.7 | ITGA4 | integrin, alpha 4 (antigen CD49D, alpha 4 subunit of VLA-4 receptor) |
| 215177_s_at | −1.6 | 1.1 | ITGA6 | integrin, alpha 6 |
| 205884_at | −1.6 | −1.7 | ITGA4 | integrin, alpha 4 (antigen CD49D, alpha 4 subunit of VLA-4 receptor) |
| 1555349_a_at | −1.6 | −1.4 | ITGB2 | integrin, beta 2 (antigen CD18 (p95), lymphocyte function-associated antigen 1; macrophage antigen 1 (mac-1) beta subunit) |
| 227259_at | −1.6 | −1.1 | CD47 | CD47 antigen (Rh-related antigen, integrin-associated signal transducer) |
| 201474_s_at | −1.6 | −1.5 | ITGA3 | integrin, alpha 3 (antigen CD49C, alpha 3 subunit of VLA-3 receptor) |
| 214021_x_at | −1.5 | −2.2 | ITGB5 | Integrin, beta 5 |
| 201656_at | −1.5 | −1.1 | ITGA6 | integrin, alpha 6 |

The results of the micro array experiment showed that compound Y and YM(ACH-Y) inhibit gene expression related to the integrin family in ES2 cells. The expression ratio of compound Y/Y3 to the control are ranging from −1.5 to −1.9 folds; wherein the expression ratio of YM/ACH-Y to the control are ranging from −1.1 to −2.5 folds.

TABLE 7

Effects of Y and YM on myosin expression in ES2 cells

| Probe Set ID | Y/D | YM/D | Gene.Symbol | Gene.Title |
|---|---|---|---|---|
| 211926_s_at | −2.2 | −1.2 | MYH9 | myosin, heavy polypeptide 9, non-muscle |
| 212372_at | −1.7 | −1.4 | MYH10 | myosin, heavy polypeptide 10, non-muscle |
| 212338_at | −1.7 | −2.1 | MYO1D | myosin ID |

TABLE 7-continued

Effects of Y and YM on myosin expression in ES2 cells

| Probe Set ID | Y/D | YM/D | Gene.Symbol | Gene.Title |
|---|---|---|---|---|
| 204527_at | −1.6 | −1.2 | MYO5A | myosin VA (heavy polypeptide 12, myoxin) |
| 202555_s_at | −1.6 | −1.2 | MYLK | myosin, light polypeptide kinase /// myosin, light polypeptide kinase |
| 203215_s_at | −1.6 | −1.6 | MYO6 | myosin VI |
| 225080_at | −1.5 | −1.4 | MYO1C | Myosin IC |
| 224823_at | −1.5 | −1.4 | MYLK | myosin, light polypeptide kinase |

The results of the micro array experiment showed that compound Y and YM(ACH-Y) inhibit gene expression related to the myosin family in ES2 cells. The expression ratio of compound Y/Y3 to the control are ranging from −1.5 to −2.2 folds; wherein the expression ratio of YM/ACH-Y to the control are ranging from −1.2 to −2.1 folds.

TABLE 8

Effects of Y and YM on cadherins expression in ES2 cells

| Probe Set ID | Y/D | YM/D | Gene. Symbol | Gene.Title |
|---|---|---|---|---|
| 244091_at | −2.0 | −1.7 | CDH13 | Cadherin 13, H-cadherin (heart) |
| 202468_s_at | −1.9 | −1.6 | CTNNAL1 | catenin (cadherin-associated protein), alpha-like 1 |
| 204726_at | −1.8 | −1.7 | CDH13 | cadherin 13, H-cadherin (heart) |
| 207149_at | −1.7 | −2.2 | CDH12 | cadherin 12, type 2 (N-cadherin 2) |
| 201533_at | −1.5 | 1.2 | CTNNB1 | catenin (cadherin-associated protein), beta 1, 88 kDa |
| 204677_at | −1.5 | −1.1 | CDH5 | cadherin 5, type 2, VE-cadherin (vascular epithelium) |
| 208407_s_at | −1.5 | −1.7 | CTNND1 | catenin (cadherin-associated protein), delta 1 |
| 203440_at | −1.4 | 1.0 | CDH2 | cadherin 2, type 1, N-cadherin (neuronal) |
| 210844_x_at | −1.4 | −1.2 | CTNNA1 | catenin (cadherin-associated protein), alpha 1, 102 kDa |

The results of the micro array experiment showed that compound Y and YM(ACH-Y) inhibit gene expression of cadherins family in ES2 cells.

TABLE 9

Effects of Y and YM on tenascin-C expression in ES2 cells

| Probe Set ID | Y/D | YM/D | Gene. Symbol | Gene.Title |
|---|---|---|---|---|
| 201645_at | −3.2 | 1.0 | TNC | Tenascin C (hexabrachion) |

The results of the micro array experiment showed that compound Y inhibit gene expression of cadherins family in ES2 cells.

TABLE 10

Effects of Y and YM on heparin sulfate expression in ES2 cells

| Probe Set ID | Y/D | YM/D | Gene.Symbol | Gene.Title |
|---|---|---|---|---|
| 201655_s_at | −2.4 | −1.3 | HSPG2 | heparan sulfate proteoglycan 2 (perlecan) |
| 219403_s_at | −1.4 | −1.3 | HPSE | Heparanase |
| 203284_s_at | −1.3 | −1.7 | HS2ST1 | heparan sulfate 2-O-sulfotransferase 1 |

The results of the micro array experiment showed that compound Y inhibit gene expression of heparin sulfate family in ES2 cells.

TABLE 11

Effects of Y and YM on CD54 expression in ES2 cells

| Probe Set ID | Y/D | YM/D | Gene.Symbol | Gene.Title |
|---|---|---|---|---|
| 202638_s_at | 1.6 | 2.3 | ICAM1 | intercellular adhesion molecule 1 (CD54), human rhinovirus receptor |

The results of the micro array experiment showed that compound Y stimulate gene expression of CD54 in ES2 cells.

TABLE 12

Effects of Y and YM on angiopoietin expression in ES2 cells

| Probe Set ID | Y/D | YM/D | Gene.Symbol | Gene.Title |
|---|---|---|---|---|
| 205572_at | 3.5 | 1.4 | ANGPT2 | angiopoietin 2 |
| 211148_s_at | 2.5 | 1.4 | ANGPT2 | angiopoietin 2 |
| 205609_at | −1.1 | −1.2 | ANGPT1 | angiopoietin 1 |
| 221009_s_at | −1.2 | −1.4 | ANGPTL4 | angiopoietin-like 4 |
| 227533_at | −1.5 | −2.3 | ANGPTL1 | Angiopoietin-like 1 |

The results of the micro array experiment showed that compound Y and YM(ACH-Y) modulate the gene expression of angiopoietin family in ES2 cells. There is a up regulation of (positive regulating on) angiopoietin 2 and a down regulation of (negative regulating on) angiopoietin 1 and angiopoietin-like 1 and angiopoietin-like 4.

Fibronectin Secretion Studies Summary:

Reduction of Fibronectin Secretion from ES2 Cells after Xanifolia-Y Treatment.

(Results of F1 and F3) In these experiments, we established and described the basic phenomenon that Y-treatment of ES2 cancer cells cause inhibition of fibronectin secretion. With a Western blot assay, we showed that ES2 cells without drug treatment (DMSO control) secret Fibronectin to medium and the amount of Fibronectin accumulated with time. However, no or only minimally secretion of Fibronectin was observed in cell culture treated with Xanifolia-Y. Inhibition of Fibronectin was observed as early as 8 hours after drug-treatment.

Inhibition of Fibronectin secretion is physiological and the determination of its quantity is based on the following criteria:
1. Fibronectin is secreted from viable cells. Only cell with over 85% viable cells after drug-treatment are employed in these experiments. The viable cells were determined by MTT assay.
2. For comparison, the immuno-band intensity from each samples are normalized with cell mass. The cell mass was determined by the MTT assay and is assigned as a MTT unit for each cell sample.

(Results of F4) Under a sub-lethal drug concentration (10 ug/ml Y), Over 95% of cells after 18 hours of Y-treatment was viable as determined by MTT assay. Western Blots show a reduction of Fibronectin secretion by cells into culture medium after Y-treatment. Scan of Fibronectin Western bands (average 6 pairs of blots) shows that there is a 40% reduction of Fibronectin secretion after 18 hours of Y-treatment.

(Results of F5) Similarly, 85% of cells after 24 hours of Y-treatment were viable as determined by the MTT assay. Western blot shows a reduction of Fibronectin bands of Y-treated samples. Based on 6 pairs of blots and after normalize them to MTT units, a 31% reduction of Fibronectin band intensity of Y-treated samples was observed. Accordingly, these results indicate that Fibronectin secretion by cells reduce 31% after 24 hours of Y-treatment.

(Results of F7) Effects of Paclitaxel on Fibronectin secretion by ES2 cells. To demonstrate that not all anticancer drugs can inhibit Fibronectin secretion from cells, we employed Paclitaxel, a well known anticancer drug that is effective for ovarian cancer. Our results showed that there is no inhibition of Fibronectin secretion with Paclitaxel treatment in ES2 cells (10 to 50 ng/ml, the $IC_{50}$ of Paclitaxel is 1.5 ng/ml). This study also showed that Fibronectin secreted by ES2 cells reduced 30-40% after Y-treatment which agrees with previous results.

(Results of F8) In addition to ES2 cells, another human ovarian cancer cells (Hey8A) were employed in this study. It was found that Y-treated Hey8A cells secrete 31% Fibronectin as compared with the DMSO control, accordingly it has a inhibition of 69%.

Beside ovarian cancer, other human cancer cells were tested in the following experiments. These experiments show that the secretion of Fibronectin from cancer cells derived from lung, bladder, liver, brain and skin is inhibited by Xanifolia-Y treatment.

(F11) For lung carcinoma cells (H460), at concentration of 20 ug/ml, there are inhibitions of Fibronectin secretion ranged from 20-60%.

(F12A) For bladder carcinoma cells (HTB-9), Xanifolia-Y (10 ug/ml) inhibits 50% of Fibronectin secretion.

(F15) In liver HepG2 cells. 10 ug/ml of xanifolia-Y inhibits 42% secretion of Fibronectin.

(F16) Incubation of brain glioblastoma T98G cells with 10 ug/ml of xanifolia-Y inhibits 27% Fibronectin secretion and with 20 ug/ml Y inhibits 74% Fibronectin secretion.

(F17) For skin SK-Mel-5 cells, the inhibition is 40-57% with 20 ug/ml of Xanifolia-Y.

Studies of Xanifolia-Y Analogs and Other Saponin on Fibronectin Secretion from ES2 Cells.

(F 23) To study the inhibition effect with other saponins, we tested the compound O54, a triterpenoid saponin isolated from the same plant. With O54, there is no inhibition activity of Fibronectin secretion in ES2 cells, even at higher dose of 40 ug/ml (instead of the usual effective concentration of 10 ug/ml). This result indicates there is specificity in triterpenoid saponin that is responsible for the inhibition effect.

(F21) To research for functional groups that are effective for Fibronectin inhibition activity, we tested several derivatives of xanifolia-Y3. In these experiments, ES2 cells treated with ACH-Y (Y3 without sugars) and AKOH-Y (Y3 without the C21, C22 angeloyl group).

With 20 ug/ml Ach-Y, there is a reduction of Fibronectin secretion from ES2 cells (ranging from 53%-75% of the control). Inhibition of Fibronectin secretion was less (or not observed) when only 10 ug/ml Ach-Y was used. However, no effect was observed with AKOH even at 80 ug/ml.

(F 13) We also tested for inhibition activity with beta-Escin, a triterpenoid saponin with only one angeloyl group attached at C21.

The results show that 10 and 20 ug/ml of beta-Escin inhibit 7% and 48%, respectively, of Fibronectin secretion from ES2 cells. But 10 ug/ml of xanifolia-Y inhibits 49% Fibronectin secretion. Results indicate that beta-Escin also inhibits Fibronectin secretion but has half potency as xanifolia-Y.

(F14) (F24) We have determined the inhibition effect of different analogs of xanifolia-Y on ES2 cells. The results are shown in the following table.

| | ES2 cells | | | | | | | |
|---|---|---|---|---|---|---|---|---|
| | β-ES-10 | X-10 | Y0-10 | Y1-10 | Y3-10 | Y7-10 | ACH-Y-20 | AKOH-80 |
| % inhibition | 19 | 39 | 34 | 41 | 47 | 34 | 48 | No effect |

All samples (except AKOH) tested have effects of inhibition of Fibronectin secretion from ES2 cells. With 80 ug/ml of AKOH-Y which is 4 times higher concentration used in others saponins (10 ug/ml), it still has no effect on inhibition of Fibronectin secretion on ES2 cells.

In conclusion, saponins in general have effects in inhibition of Fibronectin secretion from ES2 cells. The fact that AKOH-Y (the Y3 without diangeloyl group) does not show any activity, indicating that acylation of C21, 22 positions is important for the inhibition activity.

In addition to ES2 cells, other cancer cells derived from different organs were also investigated. Results are shown in following tables.

(F25, 26, 31B) Liver

HepG2

| | β-ES-10 | X-10 | Y0-10 | Y1-10 | Y3-10 | Y7-10 | ACH-Y-30 |
|---|---|---|---|---|---|---|---|
| % inhibition | 44 | 42 | 40 | 33 | 48 | 10 | 21 |

(F27, 29) Lung

H460

| | β-ES-20 | X-20 | Y0-10 | Y1-10 | Y3-10 | Y7-10 | ACH-Y-20 |
|---|---|---|---|---|---|---|---|
| % inhibition | No effect | 37 | 22 | 13 | 19 | 18 | 28 |

(F28, 30) Bladder

HTB-9

| | β-ES-10 | X-10 | Y0-10 | Y1-10 | Y3-10 | Y7-10 | ACH-Y-30 |
|---|---|---|---|---|---|---|---|
| % inhibition | 47 | 38 | 32 | 50 | 51 | 60 | No effect |

F 31, 32) Brain

T98G

| | β-ES-20 | X-20 | Y0-10 | Y1-10 | Y3-10 | Y7-10 | ACH-Y-20 |
|---|---|---|---|---|---|---|---|
| % inhibition | 66 | 52 | 22 | 40 | 26 | 24 | 30 |

(F 33) Skin

SK-MEL-5

| | β-ES-20 | X-20 | Y0-10 | Y1-10 | Y3-10 | Y7-10 | ACH-Y-30 |
|---|---|---|---|---|---|---|---|
| % inhibition | 17 | 15 | 27 | 10 | 11 | No effect | 21 |

(F20) Determination of cellular contents and secretion of Fibronectin after xanifolia-Y-treatment Results: This experiment shows that (1) there is a 46% reduction (54% of control) of Fibronectin secretion after xanifolia-Y-treatment and (2) the Fibronectin cellular content decrease 70% (30% of control) after the Y-treatment; (3) there is no change of the cellular beta-actin content in ES2 cells after the Y-treatment.

Up Regulation of Angiopoietin 2 (Ang2) in ES2 Cells with Xanifolia-Y Treatment.

Methods: ES2 (human ovarian carcinoma cells) were grew in RPMI 1640 medium. 4.5 million cells were seeded in a T75 flask and grown for 24 hours before drug-treatment.

Drug-treatment: Cells cultures were treated with 5, 10 and 15 ug/ml (final concentration) of Xanifolia-Y3 [Y3-5, Y3-10, Y3-15]. or DMSO control [D-10]. After 24 hours, cells were suspended in 1 ml of SDS sample buffer (cell-extract). Samples (80 ul/lane) were applied to 10% SDS gel and electrophoresis was conducted with 100 volts for 2 hours. Protein was transferred to a nitrocellulose membrane electrophoretically. The nitrocellulose blot was blocked with 5% non-fat dry milk in PBS. The blot was then incubated with the first antibodies (goat anti-Ang2, SIGMA A0851) and second antibody (donkey anti-goat AP conjugated, Promega V115A). The immuno-bands were developed with BCIP/NBT color development system (Promega S3771).

Results: As shown in FIG. 5, a Angiopoietin-2 immuno-band (M.W., 66K) was observed in cell extract from cells treated with 15 ug/ml Xanifolia-Y. No detectable or minimal immuno-band of Angiopoietin-2 was observed in control and low concentration of xanifolia-Y under these conditions. This results indicate that treatment of Xanifolia-Y in ES2 cells increase the cellular content of Angiopoietin-2. These results corroborate the results of Microarray studies.

This invention provides compositions and methods for modulating the gene expression in cancer cells, wherein the modulating comprises of positive and negative regulation, wherein genes being modulated are adhesion proteins; wherein modulation includes expression, production and secretion of adhesion proteins, wherein the adhesion proteins comprise fibronectin, integrins family, Myosin, vitronectin, collagen, laminin, cadherin, heparin, tenascin, CD 54, CAM. This invention provides compositions and methods for modulating angiopoietins, wherein comprises positive regulating the angiopoietin 2, wherein comprises negative regulating angiopoietin 1. The composition and method of this invention comprises a triterpene wherein acylation group at carbon position 21 and/or 22 of the triterpene is necessary for the function and are selected from angeloyl, acetyl, alkanoyl, alkenoyl and acyl group. The sugar moiety (ies) at position 5 of the triterpene is important for enhancing activity of these compounds.

Experimental Details

Experiment details of herb extraction, analysis of extract components by HPLC, determination of the cell-growth activity effected by Xanifolia Y with cells derived from different human organs using MTT Assay, purification of the bioactive components from plant extract, fractionation of plant extracts with FPLC, isolation of component Ys with preparative HPLC, determination of the chemical structure, cell experiments and aminal studings are disclosed in PCT/US05/31900, U.S. Ser. No. 11/289,142, U.S. Ser. No. 10/906,303, U.S. Ser. No. 11/131,551 and U.S. Ser. No. 11/683,198, filed on Mar. 7, 2007, PCT/US2007/077273, filed Aug. 30, 2007, U.S. Ser. No. 60/890,380, filed on Feb. 16, 2007, U.S. No. 60/947,705, filed on Jul. 3, 2007, the contents of which are incorporated herein by reference.

MicroArray
Experiment 1
Analysis of Gene Expression of ES2 Cells after Y-treatment by Microarray In this invention, the microarray experiments were done in studying the gene expression. Total number of 54676 genes has been studied.

Cell culture and drug-treatment.: ES2 cells were seeded in a T-25 flask with 4.5 million cells per flask for 24 hours. Cell culture was replaced with fresh medium with xanifolia-Y (Y) or DMSO no drug control (D) for 24 hours. Cells were then harvested for RNA isolation. Three experiments were done.

RNA extraction, labeling, hybridization, and data analysis. RNA was extracted from tumor cells using the Qiagen RNeasy Kit. RNA quality and quantity was checked by the Agilent BioAnalyzer and the NanoDrop® ND-1000 spectrophotometer respectively before further manipulation. The first and second cDNA strands were synthesized from 20 ng of total RNA using the Affymetrix T7 oligo(dT) primer protocol and kit for the two-cycle amplification. To produce amplified biotin-labeled-cRNA, the cDNA was reverse transcribed by in vitro transcription using the MegaScript kit from Ambion. 15.0 μg of the labeled cRNA was fragmented and re-checked for concentration using the NanoDrop® ND-1000 spectrophotometer. A hybridization cocktail containing Affymetrix spike-in controls and fragmented labeled cRNA was loaded onto the Human U133 Plus 2.0 GeneChip® oligonucleotide array. The Affymetrix array (Affymetrix, Inc. Santa Clara, Calif.) is comprised of over 1,300,000 unique oligonucleotide features that represent greater than 38,500 well-substantiated human genes. The array was hybridized for 16 hours at 45° C. with rotation at 60 rpm then washed and stained with a strepavidin, R-phycoerythrin conjugate stain on the Affymetrix Fluidicis Station 450. Signal amplification was done using biotinylated antistreptavidin. The arrays were scanned using the GeneChip® 3000 confocal laser scanner with autoloader. The images were analyzed and quality control metrics recorded using Affymetrix GCOS software version 1.4. Lastly, the expression value for each gene was calculated using dChip PM-only model based or Plier algorithm.

Data Analysis Methods

Pairwise comparisons were made as follows: Treated vs. Control (Y vs. D), Modified Drug vs Control (YM/ACY-H vs. D) and Treated vs. Modified Drug (Y vs. YM/ACH-Y) Cel files analyzed using the Bioconductor package of R Statistical programming. Limma analysis generated a reasonable number of changing genes between the samples.

The raw data in the .CEL files were normalized by the GCRMA method (robust multi-array analysis). It is implemented in Bioconductor (http://www.bioconductor.org/). The raw signal intensity data were normalized, background corrected and summarized based on certain statistical models, and an expression value, in log2-scale, is obtained per chip per probe set. Then the null hypothesis was tested that there's no significant changes in gene expression between the treatment pairs. This was done by LIMMA and is also implemented in Bioconductor. It uses empirical Bayes method to estimate the variance in gene expression. One comparison was made, namely, High Grade vs. Low Grade. The raw p-values were adjusted by the Benjamnin-Hochberg method for false discovery rate (FDR) control. All data sets contained a significant number of genes with a p-value less than 0.05, which is that the probability that a gene is NOT differential expressed (false positive) is 1:20.

All expression data is filtered by p-value (0.05).

The raw p-values were adjusted by the Benjamnin-Hochberg method for false discovery rate (FDR) control to yield an adjusted p-value.

Results: Please see Table 1 to 12

Inhibition of Fibronectin Secretion by Xanifolia-Y (Western Blot)

Experiment 2 (F1)

Methods:

Cells: ES2 cells were grew in T-25 flask with RPMI 1640 medium over night before drug-treatment. Drug-treatment: cells cultures were replaced with fresh RPMI medium with Xanifolia-Y (10 ug/ml final concentration) or DMSO (as control) at 0 hour. At 1, 2, 4, 8 and 24 hour, aliquot of culture medium was taken out for Fibronectin determination. Fibronectin was determined by Western blot with monoclonal antibody (SIGMA) specific to human Fibronectin only.

Results (also see FIG. 1):
1. Cells treated with DMSO (as no drug control) secret Fibronectin to medium and the amount of Fibronectin accumulated with time. There is no or only minimally secretion of Fibronectin observed in cell culture treated with Xanifolia-Y.
2. For controls, Fibronectin immunoband was not observed in RPMI medium with fetal bovine serum, or employing the normal mouse serum (NS1).

Experiment 3 (F3)

Methods:

Cells: ES2 cells were grew in RPMI 1640 medium over night before drug-treatment. Drug-treatment: cells cultures were replaced with fresh RPMI medium containing Xanifolia-Y (10 ug/ml final concentration) or DMSO (as control) at 0 hour. At 4 hours (A) or 8 hour (B), culture medium was replaced with fresh culture medium without drug. At 2, 4, 8 and 24 hour, aliquot of culture medium was taken out for Fibronectin determination. Fibronectin (FN) was determined by Western blot with monoclonal antibody (SIGMA) specific only to human Fibronectin.

Results (also see FIG. 2):
(1) Compare the control and Y-treated cells before drug removal (at 4 and 8 hours), there is a reduction of FN secretion from Y-treated cells. There is no obvious cell morphology change during these times, suggesting cells are alive.
(2) Compare the control and Y-treated cells after the removal of drug at 24 hours, it was estimated that secretion of FN from Y-treated cells was reduced to over 50%.
(3) The amount of FN secreted by Y-treated cells at 24 hours is higher than those at 8 hours (before removal of Y) indicating that cells are still alive after Y-treatment.

Experiment 4 (F4)

Methods:

Cells: ES2 cells were grew in RPMI 1640 medium over night before drug-treatment. Drug-treatment: cells cultures were replaced with fresh RPMI medium containing Xanifolia-Y (10 ug/ml final concentration) or DMSO (as control) at 0 hour. At 2, and 18 hour, aliquot of culture medium was taken out for Fibronectin determination (Western blot method). Cell viability at 18 hours was determined by MTT assay. Cultures were replaced with RPMI medium with MTT and incubated for an hour. The formation of formazan was dissolved in DMSO and OD at 570 nm was measured.

Results (also see FIG. 2):
Over 95% of cells after 18 hours of Y-treatment were viable as determined by MTT assay.
Western Blots show a reduction of FN secretion by cells into culture medium after Y-treatment. Scan of FN Western bands (average 5 sets of blots) shows that there is a 40% reduction of FN secretion after 18 hours of Y-treatment.

Experiment 5 (F5):

Methods:

Cells and Drug-treatment: same as previous experiments. After 7 or 24 hours, aliquot of culture medium was taken out for Fibronectin determination (Western blot method). Cell viability at 24 hours was determined by MTT assay.

Results:
93% and 85% of cells after 7 and 24 hours, respectively, of Y-treated cells was viable as determined by MTT assay.
Change in Fibronectin secretion during the first 7 hours of Y-treatment is not noticeable. However, after 24 hours, as compared with the control, the Fibronectin band of Y-treated samples is reduced. Based on same amount of live cells, the intensity of the immuno-bands were compared (per MTT O.D. unit). The scan of 3 pairs of blots shows a 31% reduction of Fibronectin band. Accordingly, these results indicate that Fibronectin secretion by cells reduce 31% after 24 hours of Y-treatment.

Experiment 6 (F 7)

Effects of Paclitaxel on Fibronectin secretion by ES2 cells

Methods:
Cells: ES2 cells were grew in RPMI 1640 medium over night before drug-treatment. Drug-treatment: cells cultures were replaced with fresh RPMI medium containing DMSO (as control) [D]; Xanifolia-Y (10 ug/ml) [Y]; or Paclitaxel 10 or 50 ng/ml [Ti 0, or T50]. After 24 hours, aliquot of culture medium was taken out for Fibronectin determination (Western blot method). Cell viability at 24 hours was determined by MTT assay.

Results:
Based on the MTT units (cell basis) of treated cells and compared those with the DMSO control, 87%, 94% and 91% growth of Y, T10 and T50 cells, respectively, were viable after 24 hours of treatment.

The amount of Fibronectin secreted by cells into medium was determined by Western blot assay. The amount of Fibronectin secreted per cells basis was determined by dividing the Western-band intensity with the MTT unit.

By comparing with the DMSO control, ES2 cells treated with 10 ng/ml or 50 ng/ml Taxel secret 105% or 97%, respectively, of Fibronectin into medium during 24 hours of treatment. At the same time, Y-treated ES2 cells secreted 62% of control (a reduction of 38%).

Experiment 7 (F 8)

Hey8A Cells Treated with Xanifolia-Y

Methods:
Cells: Hey8A (human ovarian carcinoma cells) were grew in RPMI 1640 medium to 90% confluent before drug-treatment. Drug-treatment: Cells cultures were replaced with fresh RPMI medium containing either DMSO (as control) [D1]; or Xanifolia-Y (10, 15, or 20 ug/ml) [Y1, Y2 and Y3]. Aliquot of medium was removed as 0 hours sample and no FN was detected at this time. After 24 hours, aliquot of culture medium was taken out for Fibronectin determination (Western blot method). Cell viability at 24 hours was determined by MTT assay. Cultures were replaced with RPMI medium (5 ml) with MTT and incubated for an hour. The formation of formazan was dissolved in DMSO and OD at 570 nm was measured.

Western Blot Spent culture medium (0.6 ml) was mixed with SDS sample buffer (0.2 ml), boiled for 3 minutes before loading to SDS gel. Samples (60 ul/lane) were applied to a 6% SDS gel and electrophoresis was conducted with 100 volts for 2 hours. Protein was transferred to a nitrocellulose paper electrophoretically (30 min at 100 volts). The Western blot was incubated with the first antibody (mouse anti-FN, specific to human FN, SIGMA F0916) and second antibody (Anti-mouse IgG AP conjugated, Promega S3721). The immunobands were developed with BCIP/NBT color development system (Promega S3771).

Results:
After 24 hours of drug-treatment, cells with 15 ug/ml and 20 ug/ml were found dead (floating) and were not further proceeded. Cells with DMSO and 10 ug/ml Y were processed.

The MTT assay showed that the growths of cells with Y-treatment (10 ug/ml) are 83% of control.

The Western blot show that the band intensity of Y-treated samples (Y1) is much reduced compare to the DMSO control (D1)

The average band intensity after corrected with the MTT unit are: 1179 and 366, for DMSO control and Y-treated samples, respectively. Accordingly, Y-treated Hey8A cells secrete 31% Fibronectin (FN) as compared with the DMSO control, or a 69% inhibition.

Experiment 8 (F 11)

Inhibition of Fibronectin Secretion by Xanifolia-Y in Human Lung Carcinoma Cells (H460)

Methods: please see Experiment 8.
Results: Lung cells (H460) are sensitive to Y in inhibition of FN secretion. Based on MTT results, cells are still viable at 20 ug/ml Y, but the inhibition of FN is over 60%.

Experiment 9 (F 12)

Inhibition of Fibronectin Secretion by Xanifolia-Y in Bladder Carcinoma Cells (HTB-9)

Methods: please see Experiment 8.
Results:
The MTT assay showed that the growth of cells treated with 10 ug/ml Y reduced to 77%-91% compared to the DMSO control.

The Western blot shows that the FN band intensity of Y-treated samples are reduced. After corrected with the MTT unit (equivalent to cell mass) there is about 50% reduction of FN band intensity per cell mass.

These results indicate that Xanifolia-Y (10 ug/ml) inhibit 50% of FN secretion.

Experiment 10 (F 13)

ES2 Cells Treated with Y and Beta-Escin

Methods: please see Experiment 8
Results:
The MTT assay showed that the growth of cells with Y, Es10 and Es20 are 89%, 90% and 82%, respectively as compared to the DMSO control.

The Western blot show that the FN band intensity of Es10 and Es20 samples are 93% and 52%, respectively, of DMSO control. The band intensity of Y10 sample is 51% of control.

These results show that 10 and 20 ug/ml of beta-escin inhibit 7% and 48%, respectively, of FN secretion. But 10 ug/ml of Y inhibits 49% FN secretion.

Results indicate that beta-escin also inhibits FN secretion but with half potency as Xanifolia-Y.

Experiment 11 (F 14)

ES2 Cells Treated with Different Xanifolia-Ys

Methods: please see Experiment 8
Two experiments were done (FN14B and FN14C). Five gels per each experiment were run.

Results:
Except for AKOH-Y (the Y3 without diangeloyl group), all samples have some degrees of inhibition of FN secretion from ES2 cells. 80 ug/ml of AKOH-Y which is 4 times higher concentration used in others saponins (10 ug/ml), still have no effect on inhibition of FN secretion on ES2 cells.

| ES2 cells | | | | | |
|---|---|---|---|---|---|
| β-ES-10 | X-10 | Y1-10 | Y3-10 | Y7-10 | AKOH-80 |
| % inhibition 19 | 39 | 41 | 47 | 34 | No effect |

Conclusion

It seems that saponins in general have effects in inhibition of Fibronectin secretion from ES2 cells. However, this experiment found that acylation of C21, 22 positions is important for the inhibition activity.

Experiment 12 (F 23)

ES2 Cells Treated with O54

Methods: Please see Experiment 8.

Results: Based on these results, there is no inhibition of FN secretion in ES2 cells with O54 treatment at 40 ug/ml.

Experiment 13 (F 24)

ES2 Treated with Y0 and Y5

Methods: please see Experiment 8.

Results: By comparing the immuno band's intensities of these samples the results of this experiment indicate that: (1) Y5 has same activity as Y3 for inhibition of FN secretion (both inhibit 68% at 10 ug/ml);
(2) Y0 is weaker as compare to Y3 for inhibition of FN secretion. (inhibit 34% at 10 ug/ml);
(3) Conclusion, both Y0 and Y5 have inhibition activity for FN secretion from ES2 cells.

Experiment 14 (F 25, 26)

HepG2 Cells Treated with Ys

Methods: Please see Experiment 8.

Results: By comparing the immuno band's intensities of these samples (see table), it was found that at concentration of 10 ug/ml. X, ES, Y0, Y1, Y3, and Y5 have inhibition effect on Fibronectin secretion from HepG2 cells. Minimum or No effect was observed with Y7, Ach (10 ug/ml) and AKOH (80 ug/ml).

| HepG2 | | | | | | |
|---|---|---|---|---|---|---|
| β-ES-10 | X-10 | Y0-10 | Y1-10 | Y3-10 | Y7-10 | ACH-Y-30 |
| % inhibition 44 | 42 | 40 | 33 | 48 | 10 | 21 |

Experiment 15 (F 27, 29)

NCI-H460 Cells (Lung) Treated with Ys

Methods: please see Experiment 8

| H460 | | | | | | |
|---|---|---|---|---|---|---|
| β-ES-20 | X-20 | Y0-10 | Y1-10 | Y3-10 | Y7-10 | ACH-Y-20 |
| % inhibition No effect | 37 | 22 | 13 | 19 | 18 | 28 |

Experiment 16 (F 28, 30)

HTB-9 Cells (Bladder) Treated with Ys

Methods: please see Experiment 8

| HTB-9 | | | | | | |
|---|---|---|---|---|---|---|
| β-ES-10 | X-10 | Y0-10 | Y1-10 | Y3-10 | Y7-10 | ACH-Y-30 |
| % inhibition 47 | 38 | 32 | 50 | 51 | 60 | No effect |

Experiment 17 (F31, 32)

T98G (Brain) Treated with Y2

Methods: please see Experiment 8

| TG98G | | | | | | |
|---|---|---|---|---|---|---|
| Y0-10 | Y1-10 | Y3-10 | Y7-10 | X-20 | ES-20 | ACH-20 |
| % inhibition 22 | 40 | 26 | 24 | 52 | 66 | 30 |

Experiment 18(F 33)

SK-MEL-5 Cells Treated with Ys

Methods: please see Experiment 8

| SK-MEL-5 | | | | | | |
|---|---|---|---|---|---|---|
| β-ES-20 | X-20 | Y0-10 | Y1-10 | Y3-10 | Y7-10 | ACH-Y-30 |
| % inhibition 17 | 15 | 27 | 10 | 11 | No effect | 21 |

Experiment 19(F 20)

Determination of Cellular Contents and Secretion of FN after Y3-Treatment

Methods:

Cells: ES2 (human ovarian carcinoma cells) were grew in RPMI 1640 medium. 1.5 million cells were seeded in a T25 flask and grown for 24 hours before drug-treatment. Drug-treatment: Cells cultures were replaced with fresh RPMI medium containing either 2.5 ul of DMSO (as control) [D]; or 10 ug/ml (final concentration) of Xanifolia-Y3 [Y]. After 24 hours, aliquot of culture medium was taken out for Fibronectin determination (Western blot method). The attached cells were suspended in 1 ml of SDS sample buffer (cell-extract).

Western Blot Spent culture medium (0.6 ml) was mixed with SDS sample buffer (0.2 ml), and the cell-extract was boiled for 3 minutes before loading to SDS gel. Samples (80 ul/lane) were applied to a 6%-10% SDS gel and electrophoresis was conducted with 100 volts for 2 hours. Protein was transferred to a nitrocellulose membrane electrophoretically (30 min at 100 volts). The nitrocellulose blot was blocked with 5% non-fat dry milk in PBS (1-2 hours). The blot was then incubated with the first antibodies (mouse anti-FN, specific to human FN, SIGMA F0916 and mouse anti-beta actin, SIGMA A5316) and second antibody (Anti-mouse IgG AP conjugated, Promega S3721). The immuno-bands were developed with BCIP/NBT color development system (Promega S3771). Determination of Western band intensity: The band-images of Western blot were captured with a digital camera (3-5 pictures were taken per gel) and the intensity of bands was determined using "Image J" software.

FN concentrations were normalized with the cellular beta-Actin concentrations. Fibronectin secreted into medium and inside Y-treated cells were determined and compare to controls (DMSO-treated cells).

Results: This experiment shows that (1) there is a 46% reduction (54% of control) of FN secretion after Y-treatment and (2) the FN cellular content decrease 70% (30% of control) after the Y-treatment; (3) there is no change of cellular beta-aecin concentration after the Y-treatment.

Experiment 20

Animal Study

Athymic Nu/Nu mice (2-3 months old) were transplanted sc with ES2 (human ovarian cancer) cells.
Five days after the transplant (day one), mice were divided into two groups (H and J) with two animals in each group.
Group H: On days 1-5, and 8-10 mice received daily drug administration of Xanifolia-Y, by i.p. route at dose of 2.5 mg/kg.
Group J mice received no drug-treatment.
Result:
Group H: Mice received drug-treatment, tumor size is 10 mm in 10 days
Group J: Mice received no drug-treatment, tumor size is 18 mm in 10 days
The tumor size is 45% smaller in mice with drug than the mice with no drug in 10 days period.

Experiment 21

Aminal Study

Methods
Athymic Nu/Nu mice (5-6 weeks old) are divided into three groups (O, P and Q) with 5-6 animals in each group.
On day 0, all mice were transplanted intra-peritoneally with ES2 (human ovarian cancer) cells.
Group O: animals received no drug-treatment.
Group P: On days 4-8, 11-15, 18-22, 25-29, 32-36, 39-43, animals received daily drug administration of Xanifolia-Y, by i.p. route at dosage of 2.5 mg/kg
Group Q: On days 10-15, 18-22, 25-29, 32-36, 39-43, animals received daily drug administration of Xanifolia-Y, by i.p. route at dosage of 2.5 mg/kg.
Result:
The median survival time of tumor bearing mice without drug-treatment is 24 days. The median survival time of tumor bearing mice with drug-treatment starting on day 4 after tumor inoculation is 58 days (extension of life span of 141%); and The median survival time of tumor bearing mice with drug-treatment started on day 10 after tumor inoculation is 31 days (extension of life span of 29%).

Experiment 22

Inhibition of Cell Adhesion by Xanifolia-Y.

Methods and Results: ES2 or Hey8A cells were plated in T25 flasks with medium containing 5 ug/ml of Xanifolia-Y.

Cultures were incubated for 5 hours. Attached cells were removed from flasks by trypsinization and the amounts were counted. Compare to no drug controls, 86±4% of ES2 cells and 67±8% of Hey8A cells were found attached to flasks under this condition. At 5 ug/ml Xanifolia-Y, over 90% of unattached cells are alive as determined by the trypan Blue exclusion assay and by their ability to re-attach to flasks when plating in medium without Xanifolia-Y. However, with 10 ug/ml Xanifolia-Y, less than 40% of cells attached to flasks and many of them are dead cells. This experiment shows that Xanifolia-Y inhibits cells adhesion process.

Experiment 23

Increase Synthesis of Angiopoietin-2 in ES2 Cells by Xanifolia-Y

Methods: ES2 (human ovarian carcinoma cells) were grew in RPMI 1640 medium. 4.5 million cells were seeded in a T75 flask and grown for 24 hours before drug-treatment.

Drug-treatment: Cells cultures were treated with 5, 10 and 15 ug/ml (final concentration) of Xanifolia-Y3 [Y3-5, Y3-10, Y3-15]. or DMSO control [D-10]. After 24 hours, cells were suspended in 1 ml of SDS sample buffer (cell-extract). Samples (80 ul/lane) were applied to a 10% SDS gel and electrophoresis was conducted with 100 volts for 2 hours. Protein was transferred to a nitrocellulose membrane electrophoretically. The nitrocellulose blot was blocked with 5% non-fat dry milk in PBS. The blot was then incubated with the first antibodies (goat anti-Ang2, SIGMA A0851) and second antibody (donkey anti-goat AP conjugated, Promega V115A). The immuno-bands were developed with BCIP/NBT color development system (Promega S3771).

Results: As shown in this Western Blot, a Angiopoietin-2 immuno-band was observed in extract from cells treated with 15 ug/ml Xanifolia-Y. No or minimal immuno-band of Angiopoietin-2 was observed in control and low concentration of xanifolia-Y. This result indicates that treatment of Xanifolia-Y in ES2 cells increase the cellular content (or synthesis) of Angiopoietin-2. These results corroborate the results of Microarray studies.

What is claimed is:
1. A method for modulating the secretion, expression or synthesis of adhesion proteins or angiopoietin in cells, comprising contacting said cells with an effective amount of an isolated, purified or synthesized compound, or its salt or ester thereof, selected from the formula:

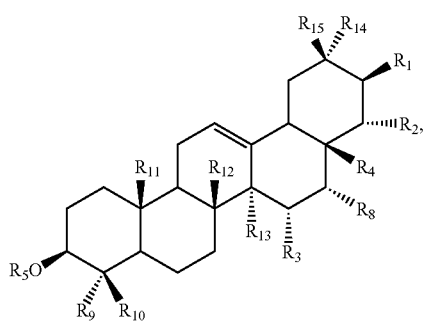

wherein $R_1$ is selected from hydrogen, hydroxyl, O-alkanoyl, O-alkenoyl and O-sugar moiety, wherein the sugar moiety is attached with two groups selected from alkanoyl and alkenoyl;

$R_2$ is selected from hydrogen, hydroxyl, alkanoyl, O-alkenoyl and O-acyl;

$R_4$ is selected from $CH_2R_6$, wherein $R_6$ is a group selected from hydroxyl, O-angeloyl, O-tigloyl, O-senecioyl, O-alkanoyl, O-alkenoyl and O-acyl;

wherein at least two of $R_1$, $R_2$ and $R_6$ are a group having an alkanoyl, alkenoyl, acyl, or any of $R_1$, $R_2$ and $R_6$ has a sugar moiety having two alkanoyl, alkenoyl, acyl; wherein the acyl groups are selected from angeloyl, tigloyl, senecioyl, methylpropanoyl, methylbutanoyl and acetyl; wherein the alkanoyl is methylpropanoyl, acetyl or methylbutanoyl; wherein the alkenoyl is angeloyl, tigloyl or senecioyl;

$R_3$ is H or OH; $R_8$ is H or OH;

$R_5$ is a hydrogen or sugar moiety(ies), wherein the sugar moiety(ies) is/are selected from a group consisting of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combination thereof; wherein $R_9$, $R_{10}$, $R_{11}$, $R_{12}$, $R_{13}$, $R_{14}$, $R_{15}$ of the compound is independently attached with a group selected from $CH_3$, $CH_2OH$, CHO, COOH, COO-alkyl, COO-aryl, COO-heterocyclic, COO-heteroaryl, $CH_2Oaryl$, $CH_2O$-heterocyclic, $CH_2O$-heteroaryl, alkyls, hydroxyl and acetyl group; wherein drug concentration is not over 10 ug/ml;

wherein the secretion of adhesion proteins is determined by a method comprising the following steps:

1. Growing cells in RPMI 1640 medium over night before drug-treatment;
2. Replacing cells cultures with fresh RPMI medium containing selected compound (1, 5, or 10 ug/ml concentration) or DMSO (as control) at 0 hour;
3. Replacing with fresh culture medium without drug at 4 hours (A) or 8 hours (B);
4. Determining adhesion proteins in aliquot of culture medium at 2, 4, 8 and 24 hour;
5. Determining adhesion proteins by Western blot with monoclonal antibody specific only to human adhesion proteins;
6. Comparing the adhesion proteins in control and drug-treated cells before drug removal at 4 and 8 hours;
7. Checking cells morphology at all times to make sure cells are alive;
8. Comparing the reduction of adhesion proteins in treated cells (compare to control cells) at 4, 8 and 24 hours; and
9. Comparing the amount of adhesion proteins secreted by treated cells at 24 hours (including those have 4 and 8 hours of drug-treatments), wherein the secretion continues after removal of drug, indicating that the cells are alive after drug treatment and capable of secreting adhesion proteins.

2. A method for modulating the secretion, expression or synthesis of adhesion proteins or angiopoietin in cells, comprising contacting said cells with an effective amount of an isolated, purified or synthesized compound, or its salt or ester thereof, selected from the formula:

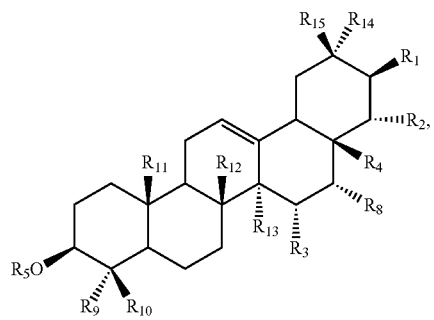

wherein $R_1$ is selected from hydrogen, hydroxyl, O-alkanoyl, O-alkenoyl, and O-sugar moiety, wherein the sugar moiety is attached with two groups selected from alkanoyl and alkenoyl;

$R_2$ is selected from hydrogen, hydroxyl, alkanoyl, O-alkenoyl and O-acyl;

$R_4$ is selected from $CH_2R_6$, wherein $R_6$ is a group selected from hydroxyl, O-angeloyl, O-tigloyl, O-senecioyl, O-alkanoyl, O-alkenoyl and O-acyl;

wherein at least two of $R_1$, $R_2$ and $R_6$ are a group having an alkanoyl, alkenoyl, acyl, or any of $R_1$, $R_2$ and $R_6$ has a sugar moiety having two alkanoyl, alkenoyl, acyl; wherein the acyl groups are selected from angeloyl, tigloyl, senecioyl, methylpropanoyl, methylbutanoyl and acetyl; wherein the alkanoyl is methylpropanoyl, acetyl or methylbutanoyl; wherein the alkenoyl is angeloyl, tigloyl or senecioyl;

$R_3$ is H or OH; $R_8$ is H or OH;

$R_5$ is a hydrogen or sugar moiety(ies), wherein the sugar moiety(ies) is/are selected from a group consisting of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combination thereof; wherein $R_9$, $R_{10}$, $R_{11}$, $R_{12}$, $R_{13}$, $R_{14}$, $R_{15}$ of the compound is independently attached with a group selected from $CH_3$, $CH_2OH$, CHO, COOH, COO-alkyl, COO-aryl, COO-heterocyclic, COO-heteroaryl, $CH_2Oaryl$, $CH_2O$-heterocyclic, $CH_2O$-heteroaryl, alkyls, hydroxyl and acetyl group; wherein drug concentration is not over 10 ug/ml;

wherein the expression or synthesis of adhesion proteins in cells is determined by a method comprising the following steps:

1. Growing cells in a T25 flask with RPMI 1640 medium for 24 hours before drug-treatment;
2. Replacing cells cultures with fresh RPMI medium containing either 2.5 ul of DMSO (as control) [D]; or 1, 5 or 10 ug/ml of tested drug;
3. Determining adhesion proteins in culture medium at 24 hours;
4. Suspending the attached cells in 1 ml of SDS sample buffer (cell-extract);
5. Mixing Spent culture medium (0.6 ml) with SDS sample buffer (0.2 ml), and boiling the cell-extract for 3 minutes before loading to SDS gel;
6. Applying samples into a 6%-10% SDS and conducting electrophoresis at 100 volts for 2 hours;
7. Transferring Protein to a nitrocellulose membrane electrophoretically (30 min at 100 volts), and blocking the nitrocellulose blot with 5% non-fat dry milk in PBS (1-2 hours);

8. Incubating the blot with the first antibodies and second antibody;
9. Developing the immuno-bands with BCIP/NBT color development system;
10. Determining Western band intensity;
11. Normalizing adhesion proteins concentration with the cellular beta-Actin concentrations; and
12. Determining the adhesion proteins secreted into medium and inside treated cells and comparing to controls.

3. A method of determining the secretion, expression or synthesis of adhesion proteins, wherein the secretion of adhesion proteins is determined by a method comprising the following steps:
1. Growing cells in RPMI 1640 medium overnight before drug-treatment;
2. Replacing cells cultures with fresh RPMI medium containing tested drug or selected compound (1, 5, or 10 ug/ml concentration) or DMSO (as control) at 0 hour;
3. Replacing with fresh culture medium without tested drug or selected compound at 4 hours (A) or 8 hours (B);
4. Determining adhesion proteins in aliquot of culture medium at 2, 4, 8 and 24 hour;
5. Determining adhesion proteins by Western blot with monoclonal antibody specific only to human adhesion proteins;
6. Comparing the adhesion proteins in control and drug-treated or compound-treated cells before drug or compound removal at 4 and 8 hours;
7. Checking cells morphology at all times to make sure cells are alive;
8. Comparing the reduction of adhesion proteins in treated cells (compare to control cells) at 4, 8 and 24 hours; and
9. Comparing the amount of adhesion proteins secreted by treated cells at 24 hours (including those having 4 and hours of drug-treatments), wherein the secretion continues after removal of drug or compound, indicating that the cells are alive after drug treatment or compound treatment and capable of secreting adhesion proteins;
wherein the expression or synthesis of adhesion proteins is determined by a method comprising the following steps:
1. Growing cells in a T25 flask with RPMI 1640 medium for 24 hours before drug-treatment;
2. Replacing cells cultures with fresh RPMI medium containing either 2.5 ul of DMSO (as control) [D]; or 1, 5 or 10 ug/ml of tested drug or selected compound;
3. Determining adhesion proteins in culture medium at 24 hours;
4. Suspending the attached cells in 1 ml of SDS sample buffer (cell-extract);
5. Mixing Spent culture medium (0.6 ml) with SDS sample buffer (0.2 ml), and boiling the cell-extract for 3 minutes before loading to SDS gel;
6. Applying samples into a 6%-10% SDS and conducting electrophoresis at 100 volts for 2 hours;
7. Transferring Protein to a nitrocellulose membrane electrophoretically (30 min at 100 volts), and blocking the nitrocellulose blot with 5% non-fat dry milk in PBS (1-2 hours);
8. Incubating the blot with the first antibodies and second antibody;
9. Developing the immuno-bands with BCIP/NBT color development system;
10. Determining Western band intensity;
11. Normalizing adhesion proteins concentration with the cellular beta-Actin concentrations; and
12. Determining the adhesion proteins secreted into medium and inside treated cells and comparing to controls;
wherein the tested drug or selected compound is selected from the formula:

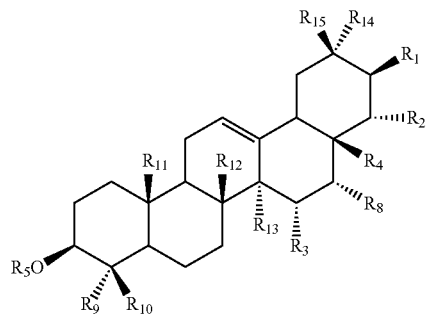

wherein $R_1$ is selected from hydrogen, hydroxyl, O-alkanoyl, O-alkenoyl, and O-sugar moiety, wherein the sugar moiety is attached with two groups selected from alkanoyl and alkenoyl;

$R_2$ is selected from hydrogen, hydroxyl, alkanoyl, O-alkenoyl and O-acyl;

$R_4$ is selected from $CH_2R_6$, wherein $R_6$ is a group selected from hydroxyl, O-angeloyl, O-tigloyl, O-senecioyl, O-alkanoyl, O-alkenoyl, O-acyl; wherein at least two of $R_1$, $R_2$ and $R_6$ are a group having an alkanoyl, alkenoyl, acyl, or any of R1, R2 and R6 has a sugar moiety having two alkanoyl, alkenoyl, acyl; wherein the acyl groups are selected from angeloyl, tigloyl, senecioyl, methylpropanoyl, methylbutanoyl and acetyl; wherein the alkanoyl is methylpropanoyl, acetyl or methylbutanoyl; wherein the alkenoyl is angeloyl, tigloyl or senecioyl;

$R_3$ is H or OH; $R_8$ is H or OH; $R_5$ is a hydrogen or sugar moiety(ies), wherein the sugar moiety(ies) is/are selected from a group consisting of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combination thereof; wherein $R_9$, $R_{10}$, $R_{11}R_{12}$, $R_{13}$, $R_{14}$, $R_{15}$ of the compound is independently attached with a group selected from $CH_3$, $CH_2OH$, CHO, COOH, COO-alkyl, COO-aryl, COO-heterocyclic, COO-heteroaryl, $CH_2Oaryl$, $CH_2O$-heterocyclic, $CH_2O$-heteroaryl, alkyls, hydroxyl and acetyl group; wherein drug concentration is not over 10 ug/ml.

4. The method of claim 1, wherein the tested drug or selected compound is in 1 ug/ml concentration.

5. The method of claim 1, wherein the tested drug or selected compound is in 5 ug/ml concentration.

6. The method of claim 1, wherein the tested drug or selected compound is in less than 10 ug/ml concentration.

7. The method of claim 2, wherein the tested drug or selected compound is in 1 ug/ml concentration.

8. The method of claim 2, wherein the tested drug or selected compound is in 5 ug/ml concentration.

9. The method of claim 2, wherein the tested drug or selected compound is in less than 10 ug/ml concentration.

10. The method of claim 3, wherein the tested drug or selected compound is in 1 ug/ml concentration.

11. The method of claim 3, wherein the tested drug or selected compound is in 5 ug/ml concentration.

12. The method of claim 3, wherein the tested drug or selected compound is in less than 10 ug/ml concentration.

13. The method of claim 1, wherein the selected compound has structure Xanifolia (Y),

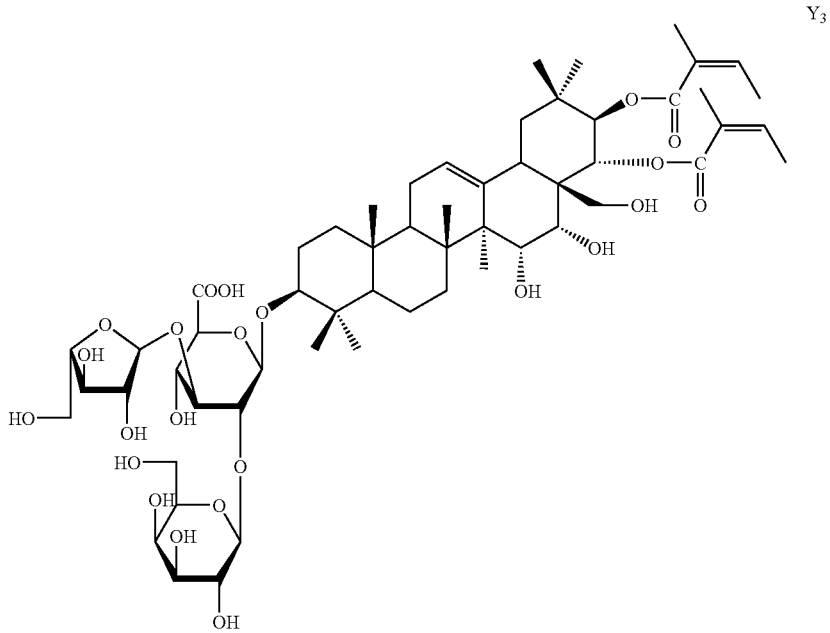

or chemical name: 3-O-[β-D-galactopyranosyl (1→2)]-α-L-arabinofuranosy (1→3)-β-D-glucuronopyranosyl-21,22-O-diangeloyl-3β,15α,16α,21β,22α, 28-hexahydroxyolean-12-ene; or wherein the selected compound has structure Xanifolia (Y1),

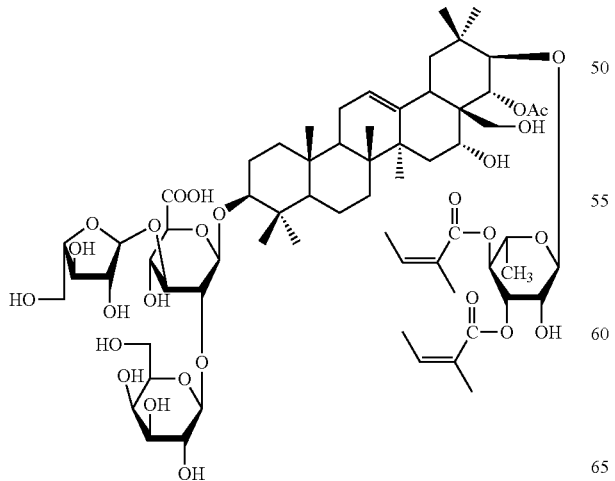

or chemical name: 3-O-[β-D-galactopyranosyl (1→2)]-α-L-arabinofuranosyl (1→3)-β-D-glucuronopyranosyl-21-O-(3,4-diangeloyl)-α-L-rhamnophyranosyl-22-O-acetyl-3β,16α,21β,22α, 28-pentahydroxyolean-12-ene; or wherein the selected compound has structure Xanifolia (Y2),

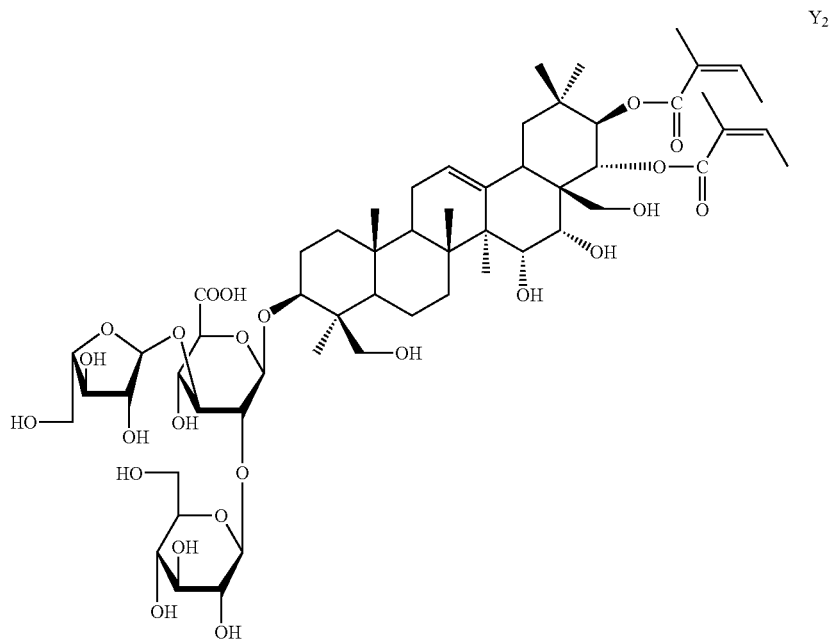

or chemical name: 3-O-[β-D-glucopyranosyl-(1→3)]-α-L-arabinofuranosy (1→3)-β-D-glucuronopyranosyl-21,22-O-diangeloyl-3β,15α,16α,21β,22α,24β, 28-heptahydroxyolean-12-ene; or wherein the selected compound has structure Xanifolia (Y8),

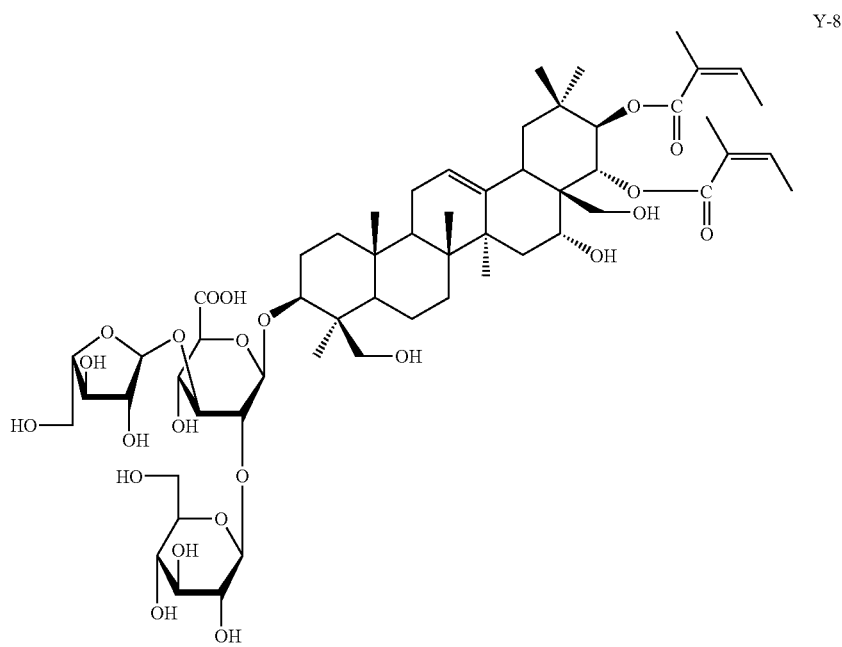

or chemical name: 3-O-[β-glucopyranosyl (1→3)]-α-arabinofuranosyl (1→3)-β-glucuronopyranosyl-21,22-O-diangeloyl-3β,16α,21β,22α,24β, 28-hexahydroxy-olean-12-ene; or wherein the selected compound has structure Xanifolia (Y9),

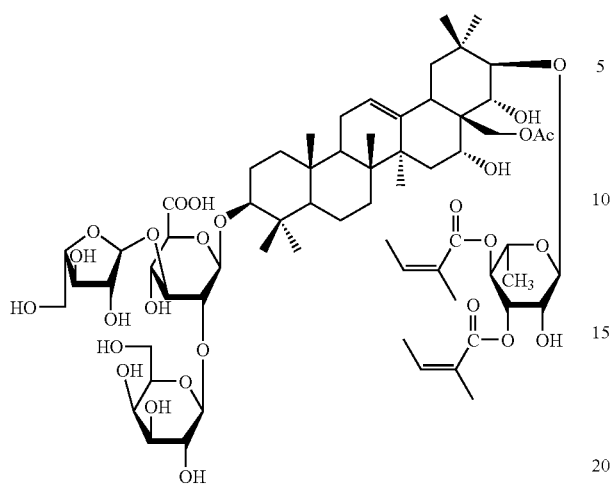

or chemical name: 3-O-[β-galactopyranosyl (1→3)]-α-arabinofuranosyl (1→3)-β-glucuronopyranosyl-21-O-(3,4-diangeloyl)-α-rhamnopyranosyl-28-O-acetyl-3β, 16α,21β,22α, 28-pentahydroxyolean-12-ene; or wherein the selected compound has structure Xanifolia (Y10),

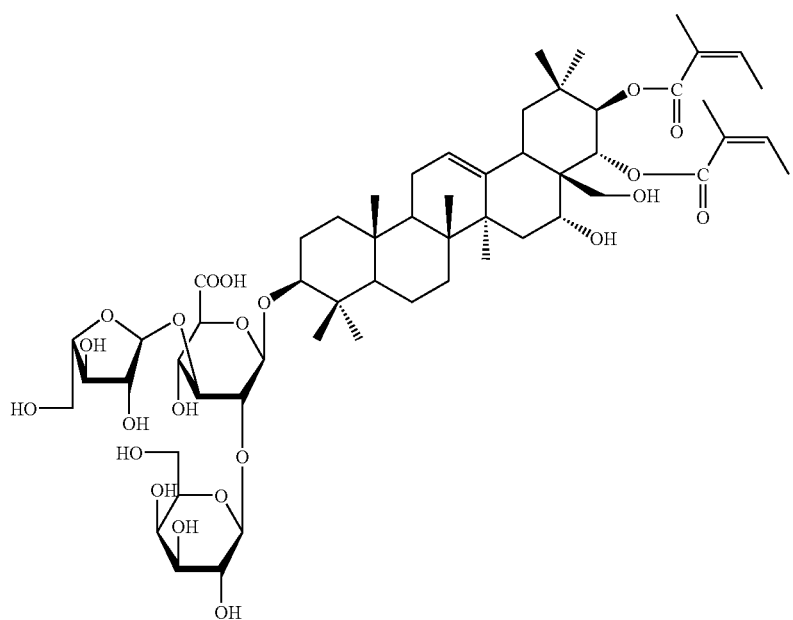

or chemical name: 3-O-[β-galactopyranosyl (1→3)]-α-arabinofuranosyl (1→3)-β-glucuronopyranosyl-21, 22-O-diangeloyl-3β,16α,21β,22α, 28-pentahydroxy-olean-12-ene; or wherein the selected compound has structure Xanifolia (Y0),

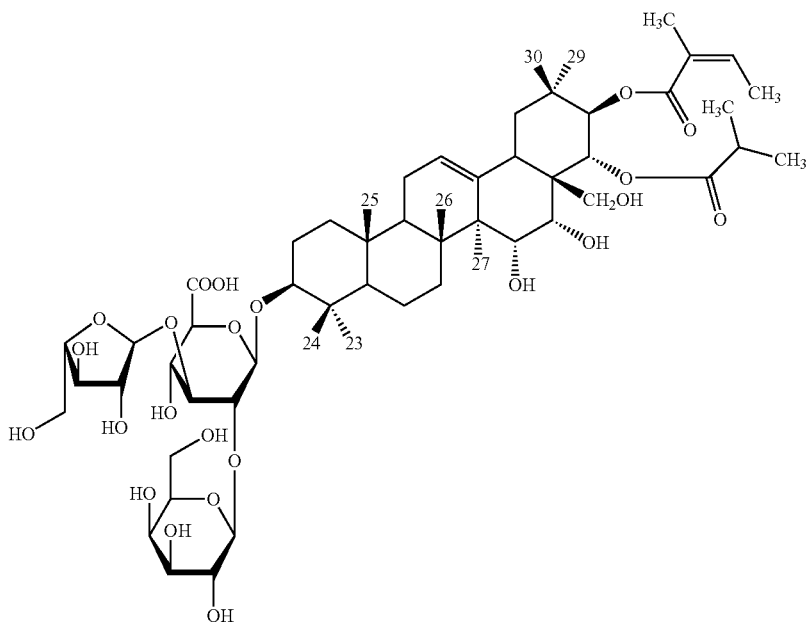

or chemical name: 3-O-[β-D-galactopyranosyl(1→3)]-α-L arabinofuranosyl(1→3)-β-D-glucuronopyranosyl-21-O-angeloyl, 22-O-(2-methylpropanoyl)-3β,15α,16α,21β,22α, 28-hexahydroxyolean-12-ene; or wherein the selected compound has structure Xanifolia (X),

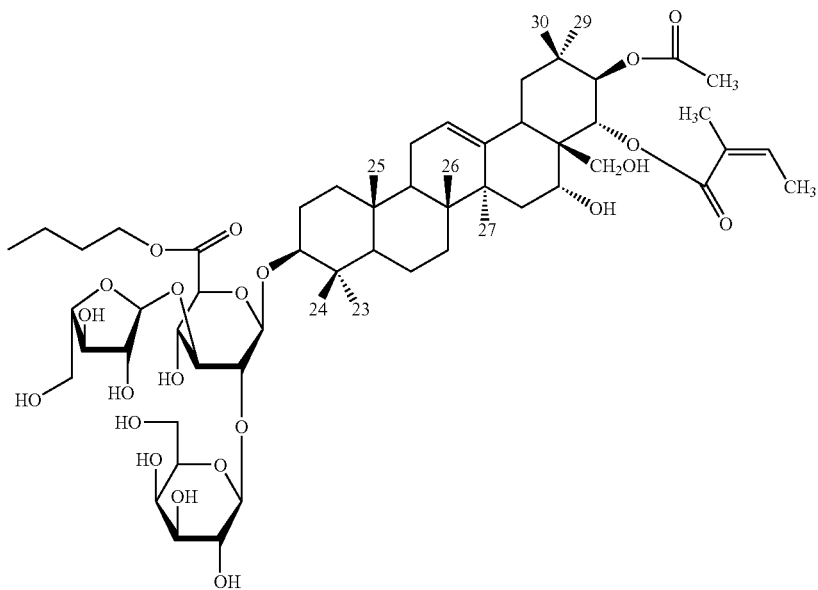

or chemical name: 3-O-{[β-D-galactopyranosyl (1→2)]-[α-L-arabinofuranosyl (1→3)]-β-D-glucuronopyranoside butyl ester}-21-O-acetyl-22-O-angeloyl-3β,16α,21β,22α, 28-pentahydroxyolean-12-ene; or wherein the selected compound has structure (Y7),

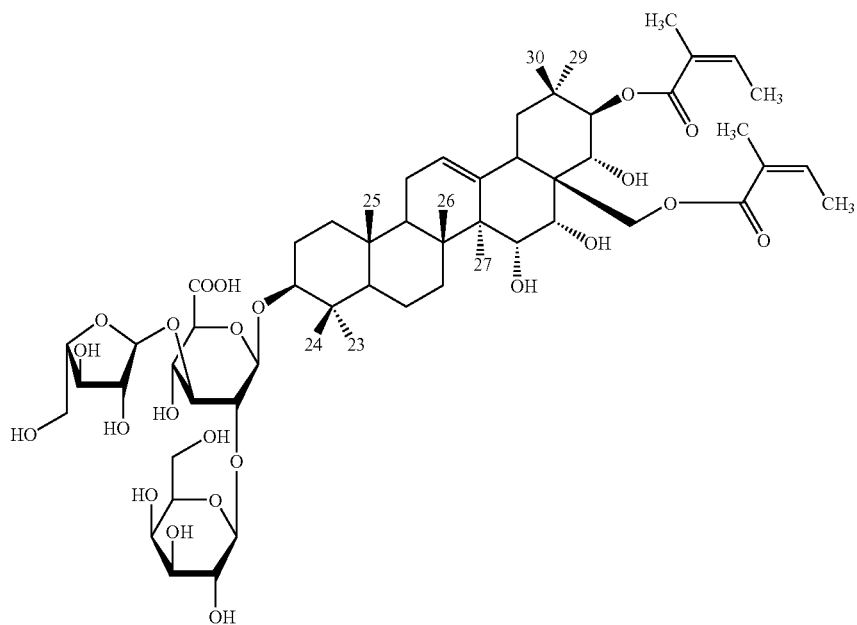

or chemical name: 3-O-[β-D-galactopyranosyl-(1→3)]-α-L-arabinofuranosyl-(1→3)-β-D-glucuronopyranosyl-21-O-angeloyl-28-O-2-methylbutanoyl-3β,15α,16α,21β,22α, 28-hexahydroxyolean-12-ene; or wherein the selected compound has structure (ACH—Y):

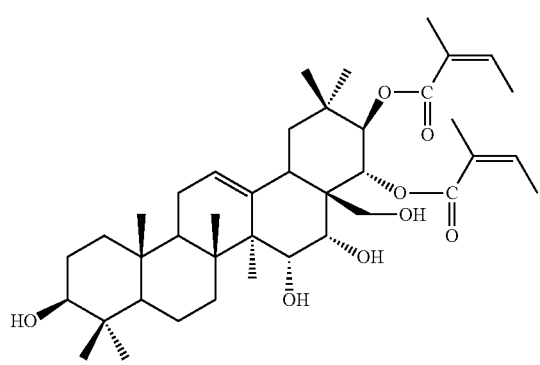

or wherein the selected compound has structure:

or chemical name: 3-O-[β-glucopyranosyl (1→2)]-β-arabinofuranosyl (1→4)-β-glucuronopyranosyl-21-O-angeloyl-22-O-acteyl-3β,16α,21β,22α,24β, 28-hexahydroxyolean-12-ene.

14. The method of claim 2, wherein the selected compound has structure Xanifolia(Y),

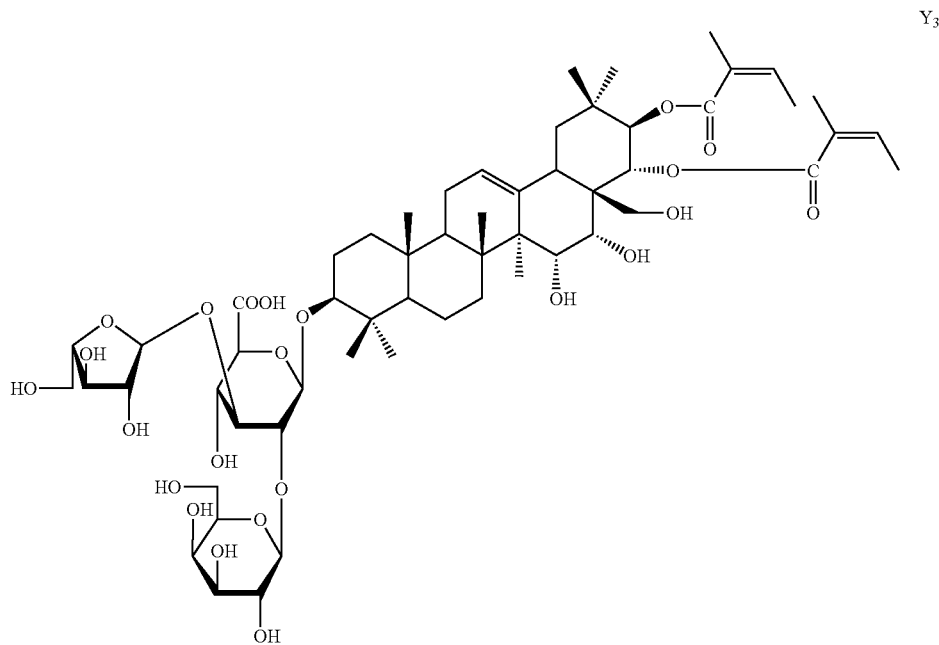

or chemical name: 3-O-[β-D-galactopyranosyl (1→2)]-α-L-arabinofuranosy (1→3)-β-D-glucuronopyranosyl-21, 22-O-diangeloyl-3β,15α,16α,21β,22α, 28-hexahydroxyolean-12-ene; or wherein the selected compound has structure Xanifolia (Y1),

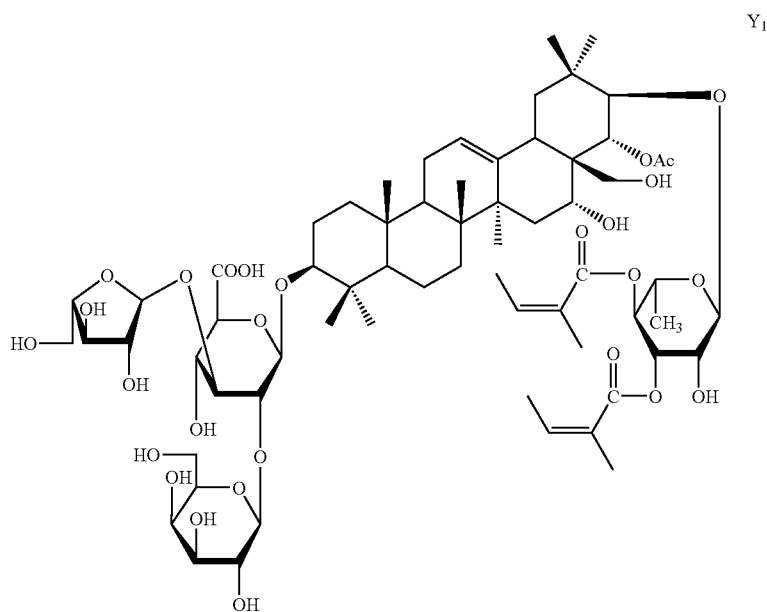

or chemical name: 3-O-[β-D-galactopyranosyl (1→3)]-α-L-arabinofuranosyl (1→3)-β-D-glucuronopyranosyl-21-O-(3,4-diangeloyl)-α-L-rhamnophyranosyl-22-O-acetyl-3β,16α,21β,22α, 28-pentahydroxyolean-12-ene; or wherein the selected compound has structure Xanifolia (Y2),

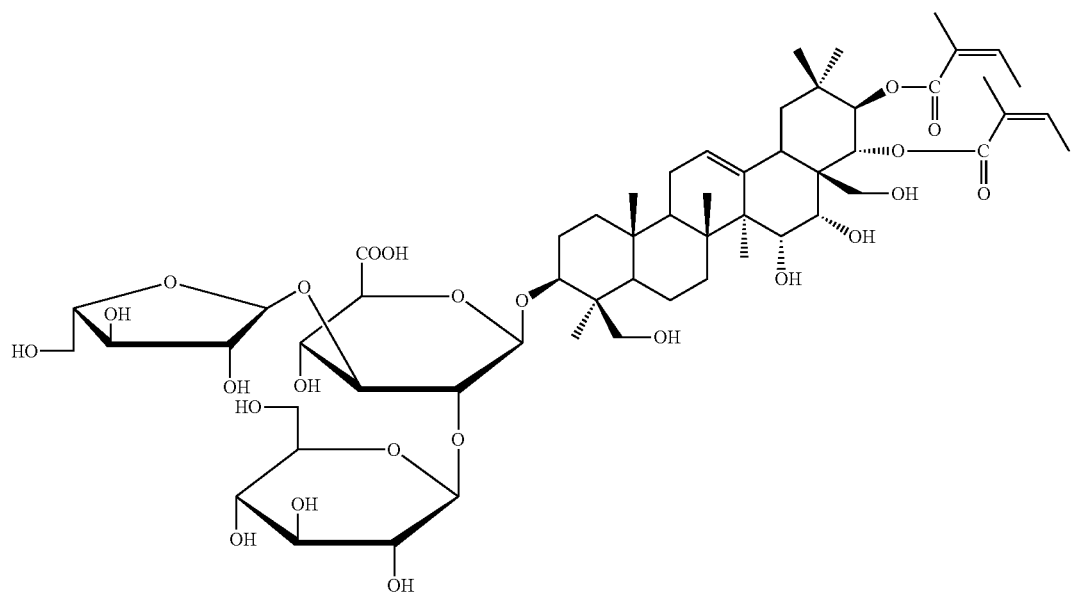

or chemical name: 3-O-[β-D-glucopyranosyl-(1→2)]-α-L-arabinofuranosy (1→3)-β-D-glucuronopyranosyl-21,22-O-diangeloyl-3β,15α,16α,21β,22α,24β, 28-heptahydroxyolean-12-ene; or wherein the selected compound has structure Xanifolia (Y8),

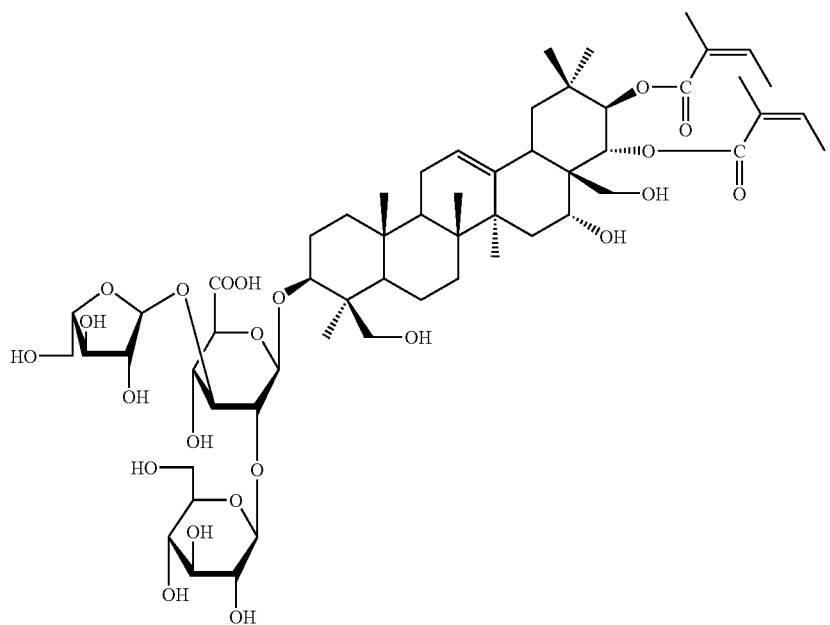

or chemical name: 3-O-[β-glucopyranosyl (1→2)]-α-arabinofuranosyl (1→3)-β-glucuronopyranosyl-21, 22-O-diangeloyl-3β,16α,21β,22α,24β, 28-hexahydroxyolean-12-ene; or wherein the selected compound has structure Xanifolia (Y9),

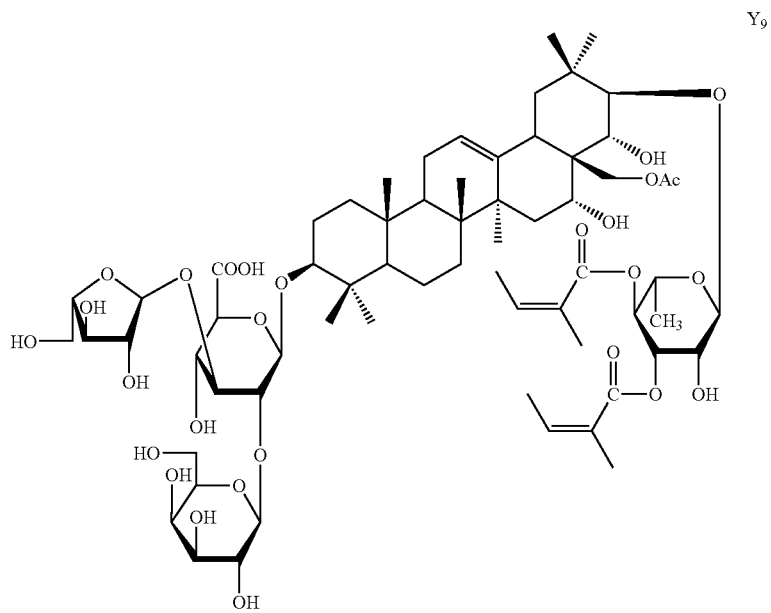

or chemical name: 3-O-[β-galactopyranosyl (1→2)]-α-arabinofuranosyl (1→3)-β-glucuronopyranosyl-21-O-(3,4-diangeloyl)-α-rhamnopyranosyl-28-O-acetyl-3β, 16α,21β,22α, 28-pentahydroxyolean-12-ene; or wherein the selected compound has structure Xanifolia (Y10),

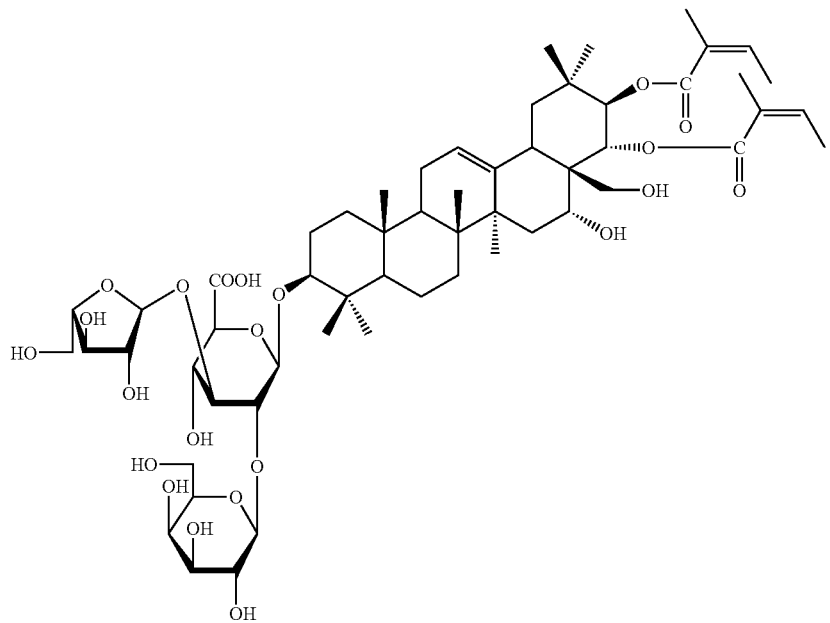

or chemical name : 3-O-[β-galactopyranosyl(1→2)]-α-arabinofuranosyl (1→3)-β-glucuronopyranosyl-21,22-O-diangeloyl-3β,16α,21β,22α, 28-pentahydroxyolean-12-ene; or wherein the selected compound has structure Xanifolia (Y0),

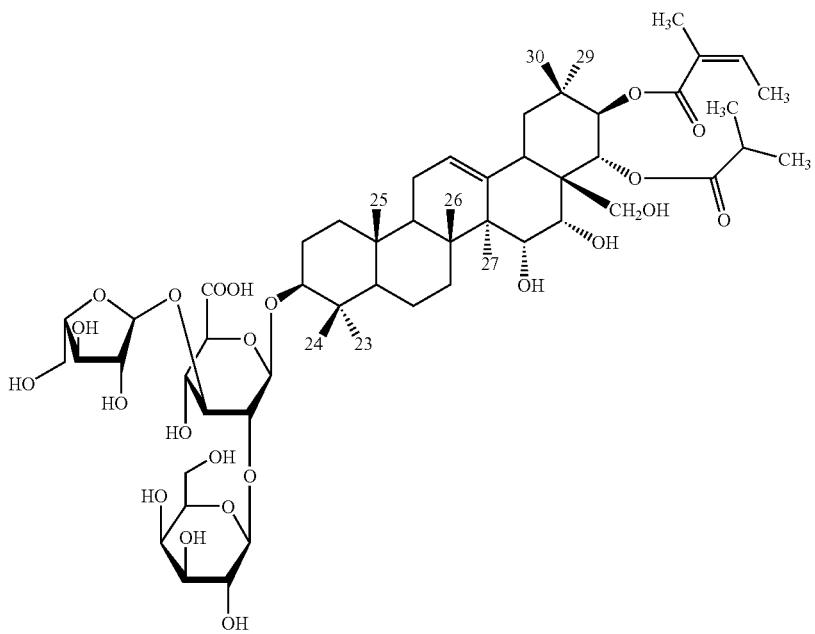

or chemical name: 3-O-[β-D-galactopyranosyl(1→2)]-α-L-arabinofuranosyl(1→3)-β-D-glucuronopyranosyl-21-O-angeloyl, 22-O-(2-methylpropanoyl)-3β,15α,16α,21β,22α, 28-hexahydroxyolean-12-ene; or wherein the selected compound has structure Xanifolia (X),

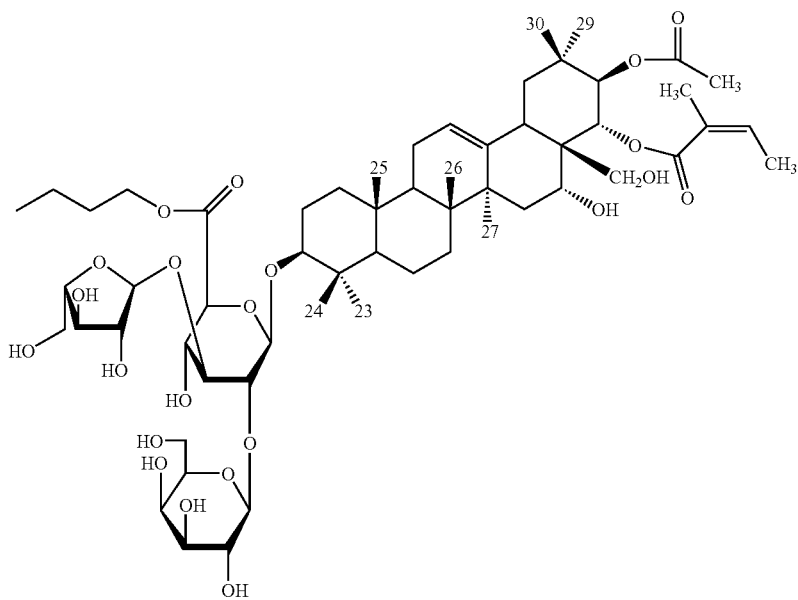

or chemical name: 3-O-{[β-galactopyranosyl (1→2)]-[α-L-arabinofuranosyl (1→3)]-β-D-glucuronopyranoside butyl ester}-21-O-acetyl-22-O-angeloyl-3β,16α,21β, 22α, 28-pentahydroxyolean-12-ene; or wherein the selected compound has structure (Y7),

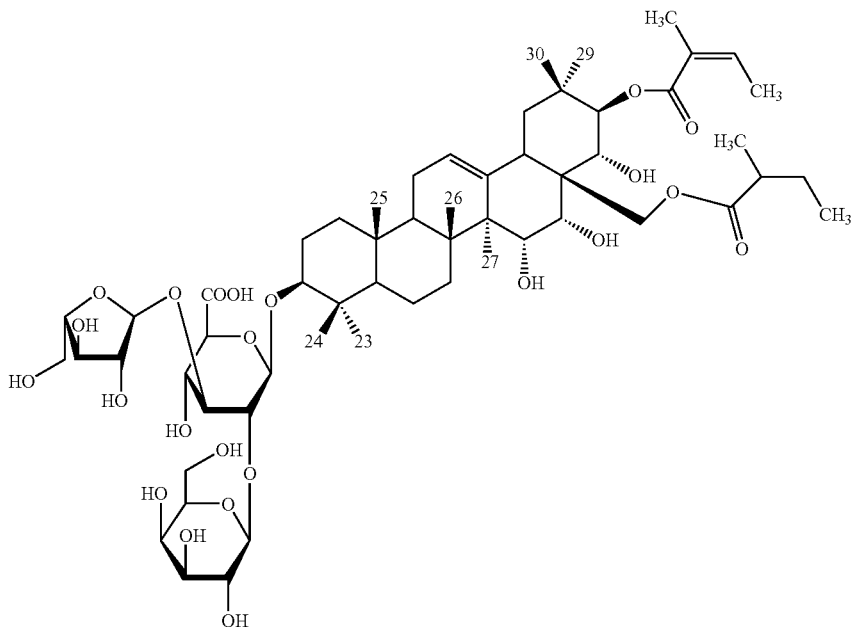

or chemical name: 3-O-[β-D-galactopyranosyl-(1→2)]-α-L-arabinofuranosyl-(1→3)-β-D-glucuronopyranosyl-21-O-angeloyl-28-O-2-methylbutanoyl-3β,15α,16α,21β,22α, 28-hexahydroxyolean-12-ene; or wherein the selected compound has structure (ACH—Y):

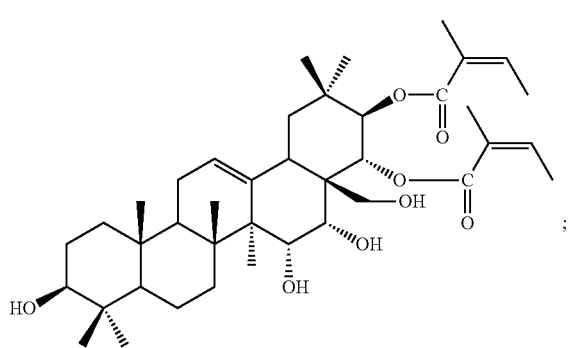

;

or wherein the selected compound has structure:

or chemical name: 3-O-[β-glucopyranosyl (1→2)]-β-arabinofuranosyl (1→4)-β-glucuronopyranosyl-21-O-angeloyl-22-O-acteyl-3β,16α,21β,22α,24β, 28-hexahydroxyolean-12-ene.

15. The method of claim 3, wherein the selected compound has structure Xanifolia(Y),

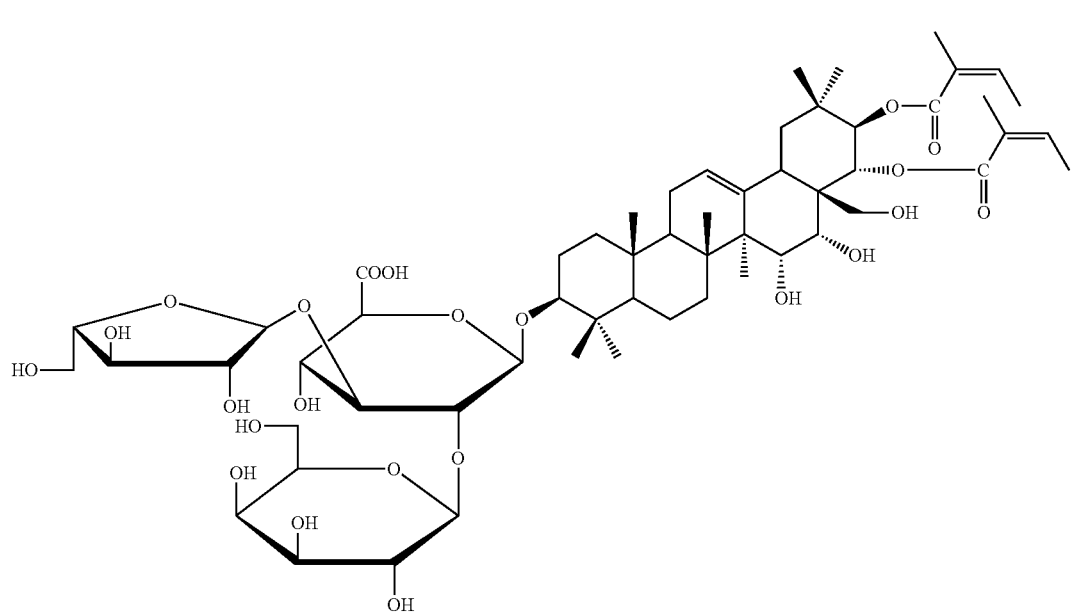

or chemical name: 3-O-[β-D-galactopyranosyl (1→2)]-α-L-arabinofuranosy (1→3)-β-D-glucuronopyranosyl-21,22-O-diangeloyl-3β,15α,16α,21β,22α, 28-hexahydroxyolean-12-ene; or wherein the selected compound has structure Xanifolia (Y1),

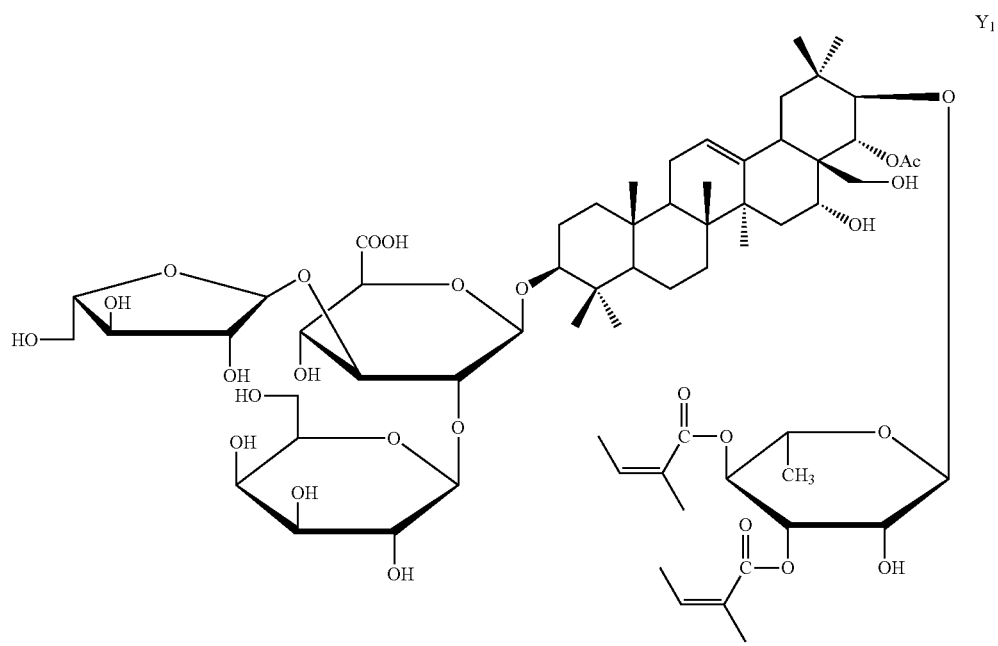

or chemical name: 3-O-[β-D-galactopyranosyl (1→2)]-α-L-arabinofuranosyl (1→3)-β-D-glucuronopyranosyl-21-O-(3,4-diangeloyl)-α-L-rhamnophyranosyl-22-O-acetyl-3β,16α,21β,22α, 28-pentahydroxyolean-12-ene; or wherein the selected compound has structure Xanifolia (Y2),

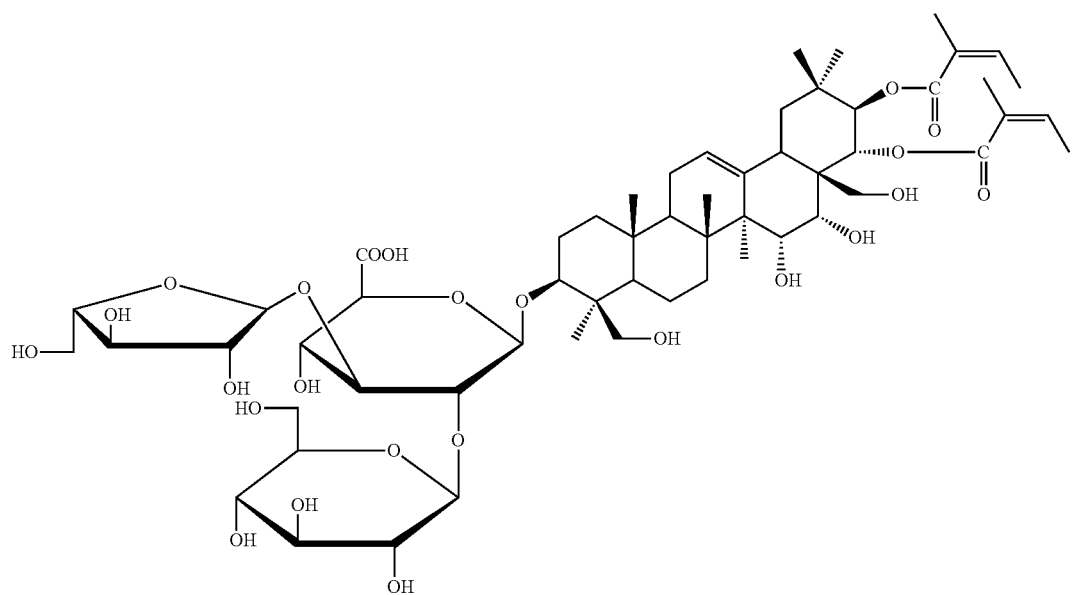

or chemical name: 3-O-[β-D-glucopyranosyl-(1→2)]-α-L-arabinofuranosy (1→3)-β-D-glucuronopyranosyl-21,22-O-diangeloyl-3β,15α,16α,21β,22α,24β, 28-heptahydroxyolean-12-ene; or wherein the selected compound has structure Xanifolia (Y8),

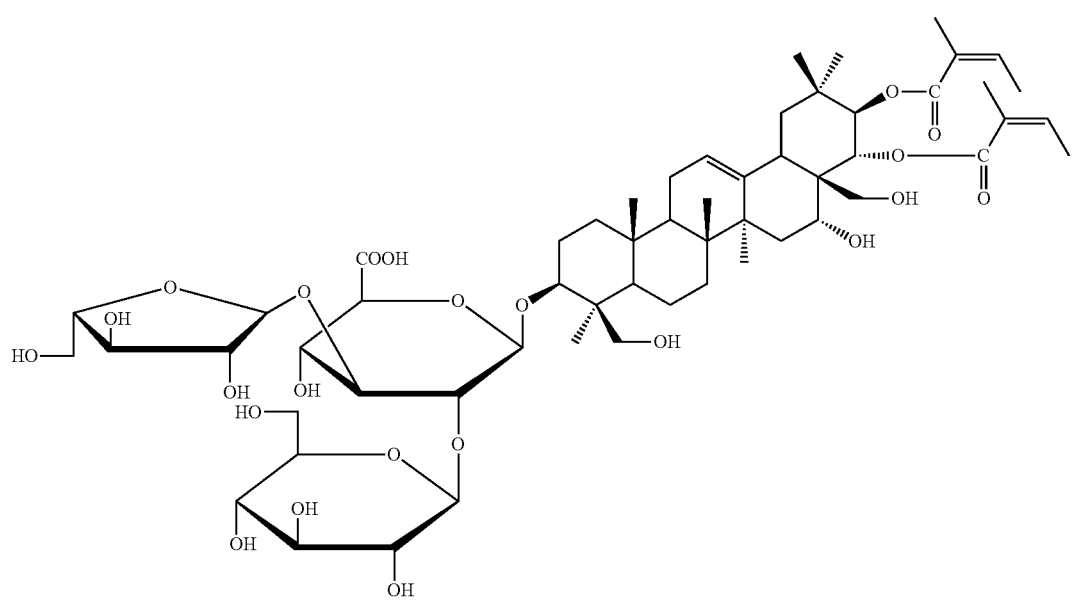

or chemical name: 3-O-[β-glucopyranosyl (1→2)]-α-arabinofuranosyl (1→3)-β-glucuronopyranosyl-21, 22-O-diangeloyl-3β,16α,21β,22α,24β, 28-hexahydroxyolean-12-ene; or wherein the selected compound has structure Xanifolia (Y9),

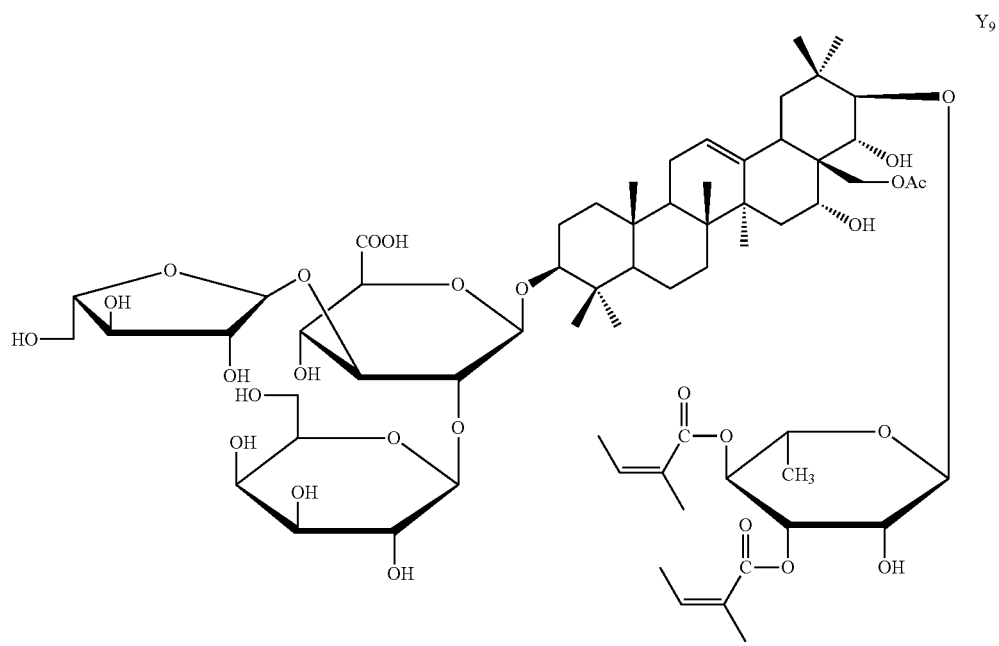

or chemical name: 3-O-[βgalactopyranosyl (1→2)]-α-arabinofuranosyl (1→3)-β-glucuronopyranosyl-21-O-(3, 4-diangeloyl)-α-rhamnopyranosyl-28-O-acetyl-3β, 16α,21β,22α, 28-pentahydroxyolean-12-ene; or wherein the selected compound has structure Xanifolia (Y10),

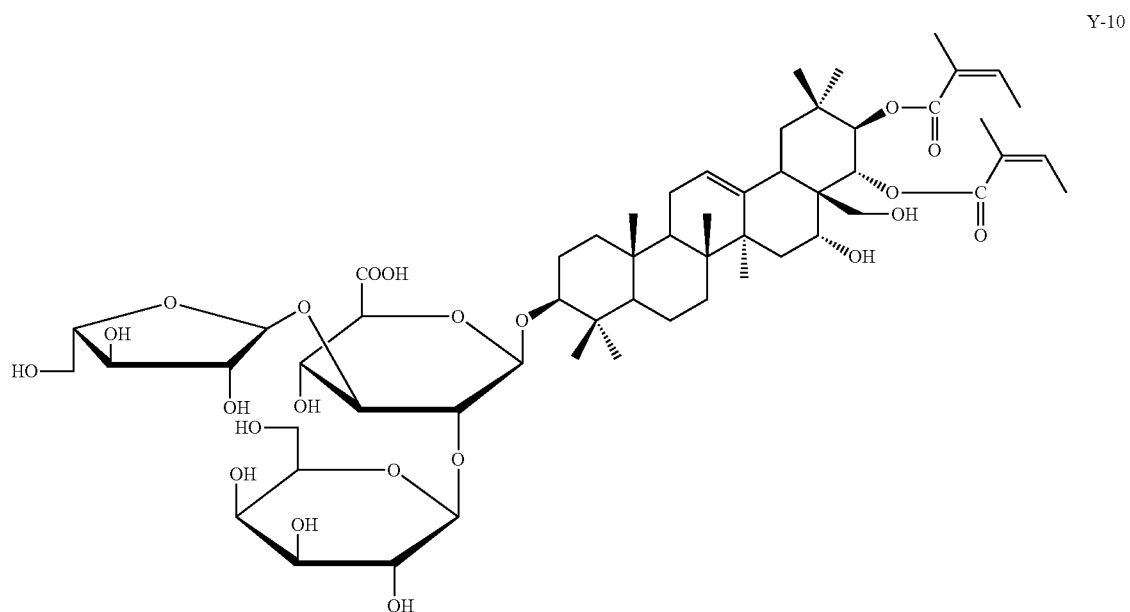

or chemical name: 3-O-[β-galactopyranosyl (1→2)]-α-arabinofuranosyl (1→3)-β-glucuronopyranosyl-21, 22-O-diangeloyl-3β,16α,21β,22α, 28-pentahydroxy-olean-12-ene; or wherein the selected compound has structure Xanifolia (Y0),

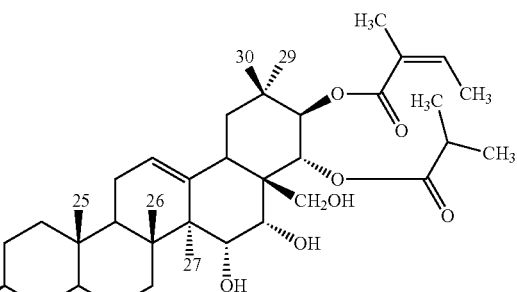
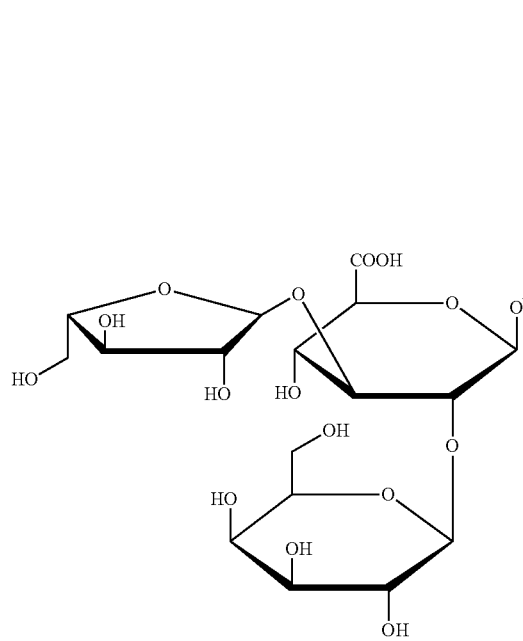
or chemical name: 3-)-[β-D-galactopyranosyl(1→2)]-α-L-arabinofuranosyl(1→3)-β-D-glucuronopyranosyl-21-O-angeloyl, 22-O-(2-methylpropanoyl)-3β,15α,16α,21β,22α, 28-hexahydroxyolean-12-ene; or
wherein the selected compound has structure Xanifolia (X),
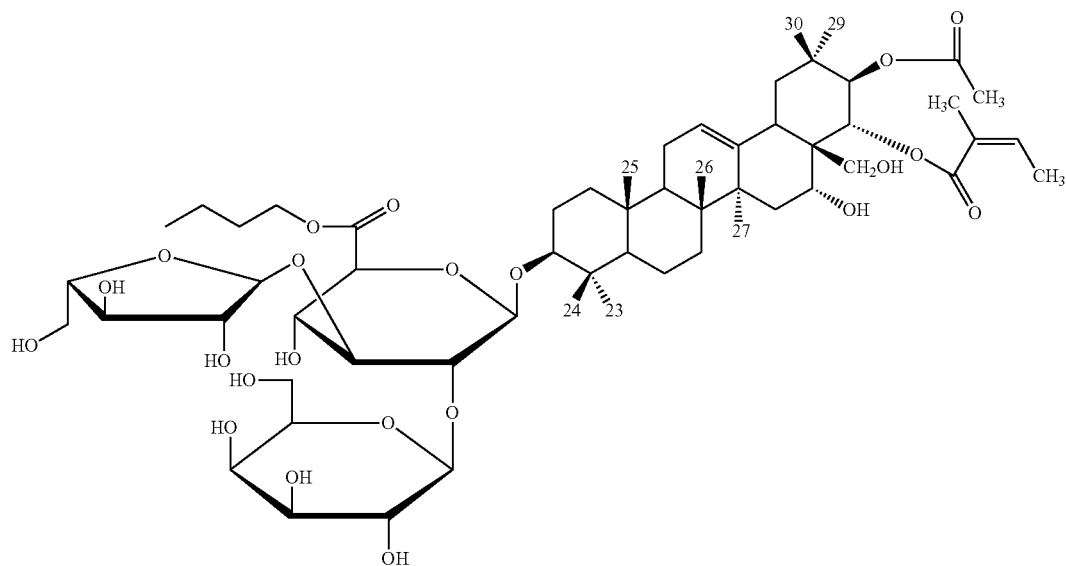

or chemical name: 3-O-{[β-D-galactopyranosyl (1→2)]-[α-L-arabinofuranosyl (1→3)]-β-D-glucuronopyranoside butyl ester}-21-O-acetyl-22-O-angeloyl-3β,16α,21β,22α, 28-pentahydroxyolean-12-ene; or wherein the selected compound has structure (Y7),

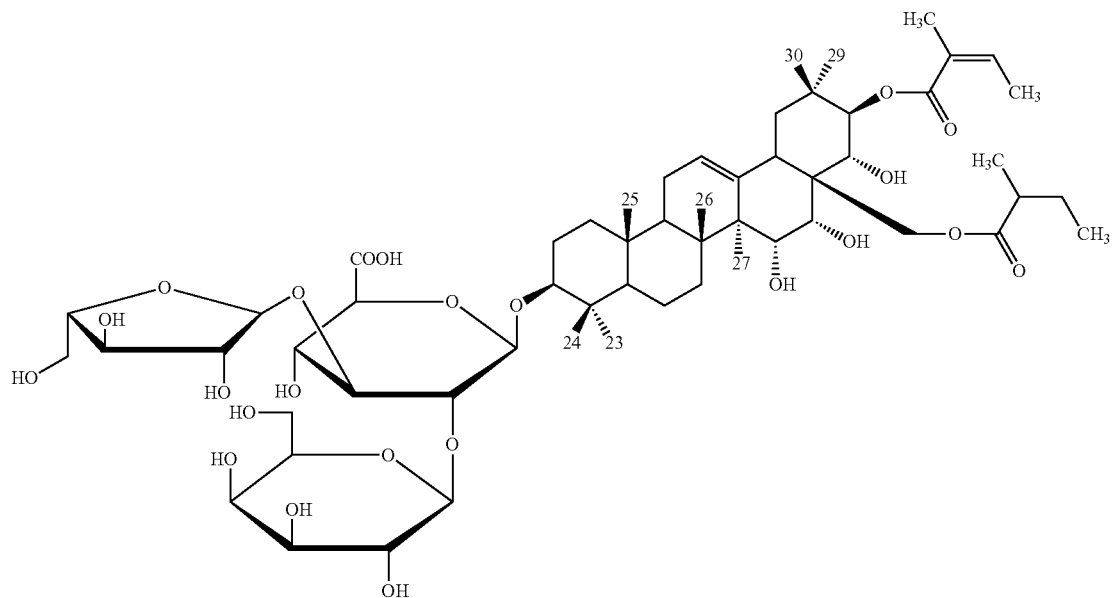

or chemical name: 3-O-[β-D-galactopyranosyl-(1→2)]-α-L-arabinofuranosyl-(1→3)-β-D-glucuronopyranosyl-21-O-angeloyl-28-O-2-methylbutanoyl-3β,15α,16α,21β,22α, 28-hexahydroxyolean-12-ene; or wherein the selected compound has structure (ACH—Y):

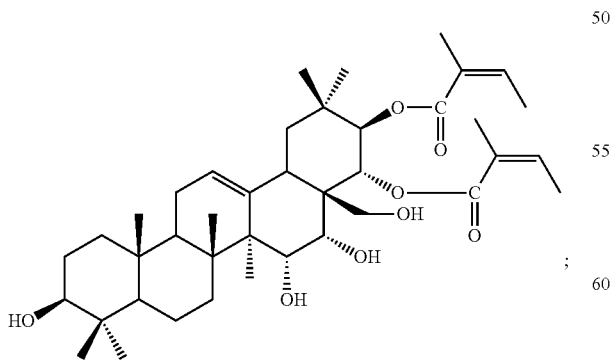

or wherein the selected compound has structure:

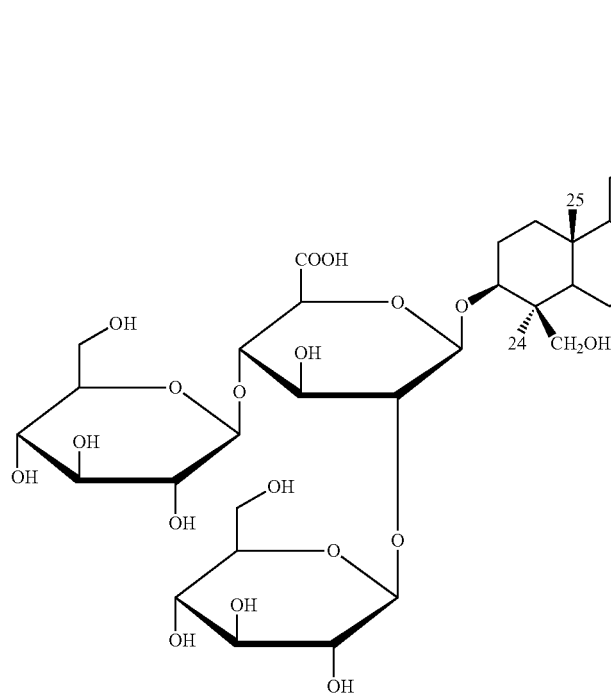
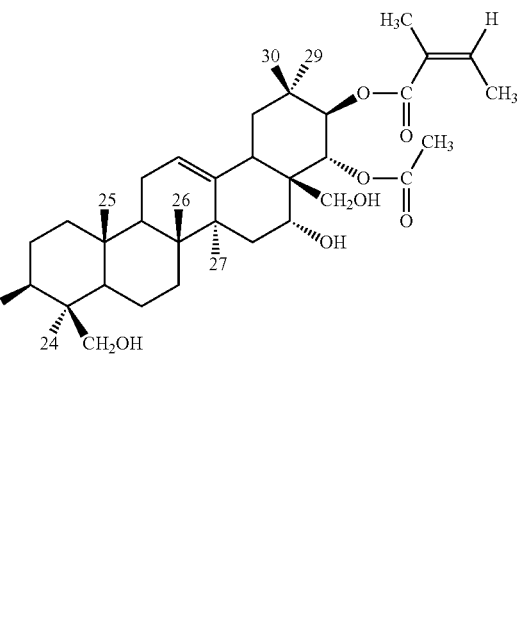

or chemical name: 3-O-[β-glucopyranosyl (1→2)]-β-arabinofuranosyl (1→4)-β-glucuronopyranosyl-21-O-angeloyl-22-O-acteyl-3β,16α,21β,22α,24β, 28-hexahydroxyolean-12-ene.

16. The method of claim 1, wherein the adhesion proteins comprise fibronectin, integrins family, Myosin, vitronectin, collagen, laminin, cadherin, heparin, tenascin, CD 54, CAM.

17. The method of claim 2, wherein the adhesion proteins comprise fibronectin, integrins family, Myosin, vitronectin, collagen, laminin, cadherin, heparin, tenascin, CD 54, CAM.

18. The method of claim 3, wherein the adhesion proteins comprise fibronectin, integrins family, Myosin, vitronectin, collagen, laminin, cadherin, heparin, tenascin, CD 54, CAM.

\* \* \* \* \*